(12) United States Patent
O'Mahony et al.

(10) Patent No.: US 6,916,789 B2
(45) Date of Patent: Jul. 12, 2005

(54) PEYER'S PATCH AND/OR M-CELL TARGETING LIGANDS

(75) Inventors: Daniel O'Mahony, Blackrock (IE); Imelda Lambkin, Sutton (IE); Lisa Higgins, Donabate (IE)

(73) Assignee: Merrion Research I Limited, Dublin (IE)

(*) Notice: Subject to any disclaimer, the term of this patent is extended or adjusted under 35 U.S.C. 154(b) by 0 days.

(21) Appl. No.: 10/185,815

(22) Filed: Jun. 28, 2002

(65) Prior Publication Data

US 2003/0096354 A1 May 22, 2003

Related U.S. Application Data

(60) Provisional application No. 60/302,591, filed on Jul. 2, 2001.

(51) Int. Cl.$^7$ ............... A61K 38/10; A61K 39/39; C07K 7/08
(52) U.S. Cl. ............... 514/14; 424/184.1; 424/192.1; 424/196.11; 424/197.11; 424/450; 514/2; 514/12; 514/13; 530/300; 530/324; 530/327; 530/350
(58) Field of Search ............... 424/450, 184.1, 424/192.1, 193.1, 196.11, 197.11; 514/2, 12, 13, 14, 15, 16, 17, 21; 530/300, 324, 327, 328, 329, 330, 350

(56) References Cited

U.S. PATENT DOCUMENTS

| | | | |
|---|---|---|---|
| 5,254,342 A | 10/1993 | Shen et al. | 424/401 |
| 5,534,496 A | 7/1996 | Lee et al. | 514/17 |
| 5,811,304 A | * 9/1998 | Huang | 435/325 |
| 6,030,613 A | 2/2000 | Blumberg et al. | 424/134.1 |
| 6,060,082 A | 5/2000 | Chen et al. | 424/450 |
| 6,086,875 A | 7/2000 | Blumberg et al. | 424/134.1 |
| 6,117,632 A | 9/2000 | O'Mahony | 435/6 |

FOREIGN PATENT DOCUMENTS

| | | |
|---|---|---|
| JP | 2001-245675 A * | 9/2001 |
| WO | WO 93/14206 A2 * | 7/1993 |
| WO | WO 93/20834 | 10/1993 |
| WO | WO 95/24419 A1 * | 9/1995 |
| WO | WO 00/053623 | 9/2000 |
| WO | WO 01/87954 A1 * | 11/2001 |

OTHER PUBLICATIONS

Monden et al. Isolation and Characterization of a Novel Ligand–dependent Thyroid Hormone Receptor–coactivation Protein. The Journal Of Biological Chemistry. vol. 272, No. 47, pp. 29834–29841 (Nov. 21, 1997).*
Bajaj–Elliot et al., J Clin Invest, 102, 1473–1480 (1998).
Bolte et al., J Biochem Biophys Methods, 34, 186–203 (1997).
Drapkin et al., J Clin Invest, 105, 589–596 (2000).
Foster et al., Vaccine, 15, 546–71 (1998).
Gibson et al., Gut, 5, 581–584 (1997).
Hardy and Garbers, J Biol Chem, 44, 26025–26028 (1995).
Itoh et al., J Cell Biol, 3, 491–502 (1993).
Jawhari et al., Gut, 5, 581–584 (1997).
Kerncis et al., Science, 277, 949–952 (1997).
Pender et al., Ann NY Acad Sci, 878, 581–582 (1999).
Traber, Biochem Biophys Res Commun, 173, 765–773 (1990).
Turner and Kinet, Nature, 402, 24–30 (1999).
Ugwu et al., Biochemistry, 2, 7231–7236 (1998).
Van Damme et al., Plant Mol Bio, 3, 579–598 (1995).
Werner, Cytokine Growth Factor Rev, 2, 156–165 (1998).
Wilson and Matrisian., Int J Biochem Cell Biol, 2, 123–136 (1996).
Wolpert et al., J Surg Res, 63, 345–348 (1996).

* cited by examiner

Primary Examiner—Jeffrey Edwin Russel
(74) Attorney, Agent, or Firm—Synnestvedt & Lechner LLP

(57) ABSTRACT

Purified synthetic polypeptide ligands comprising a 12-mer L-peptide, D-peptides being the D-form of the 12-mer L-peptides, 12-mer retro-inverted peptides being the retro-inverted form of the 12-mer L-peptide, or fragments and homologues thereof, are disclosed. These ligands are for targeting pharmaceutical agents and carriers comprising such agents to intestinal epithelial tissue, especially Peyer's patch and/or M-Cell tissue. Methods of using the ligands are also disclosed.

58 Claims, 32 Drawing Sheets

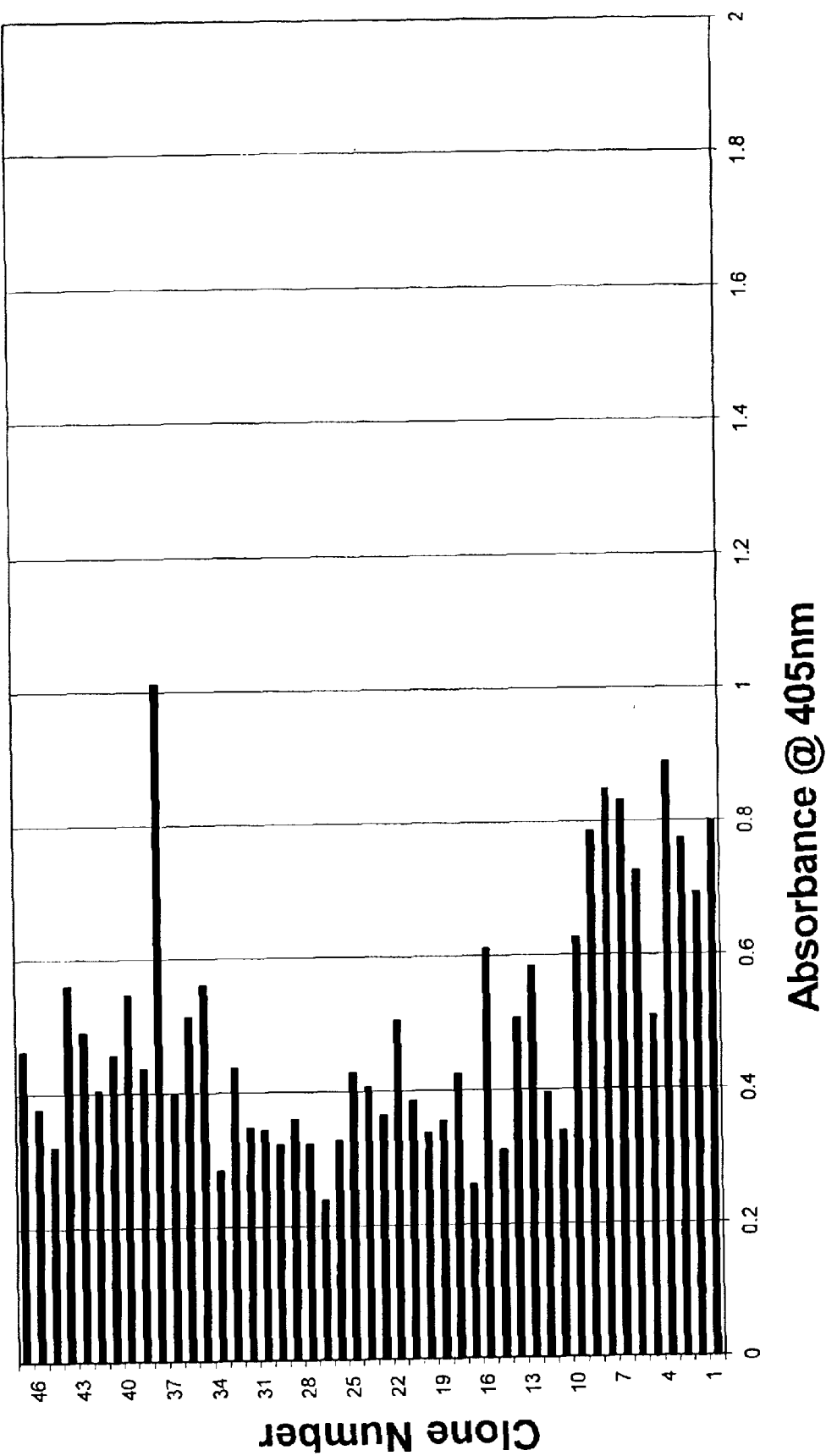

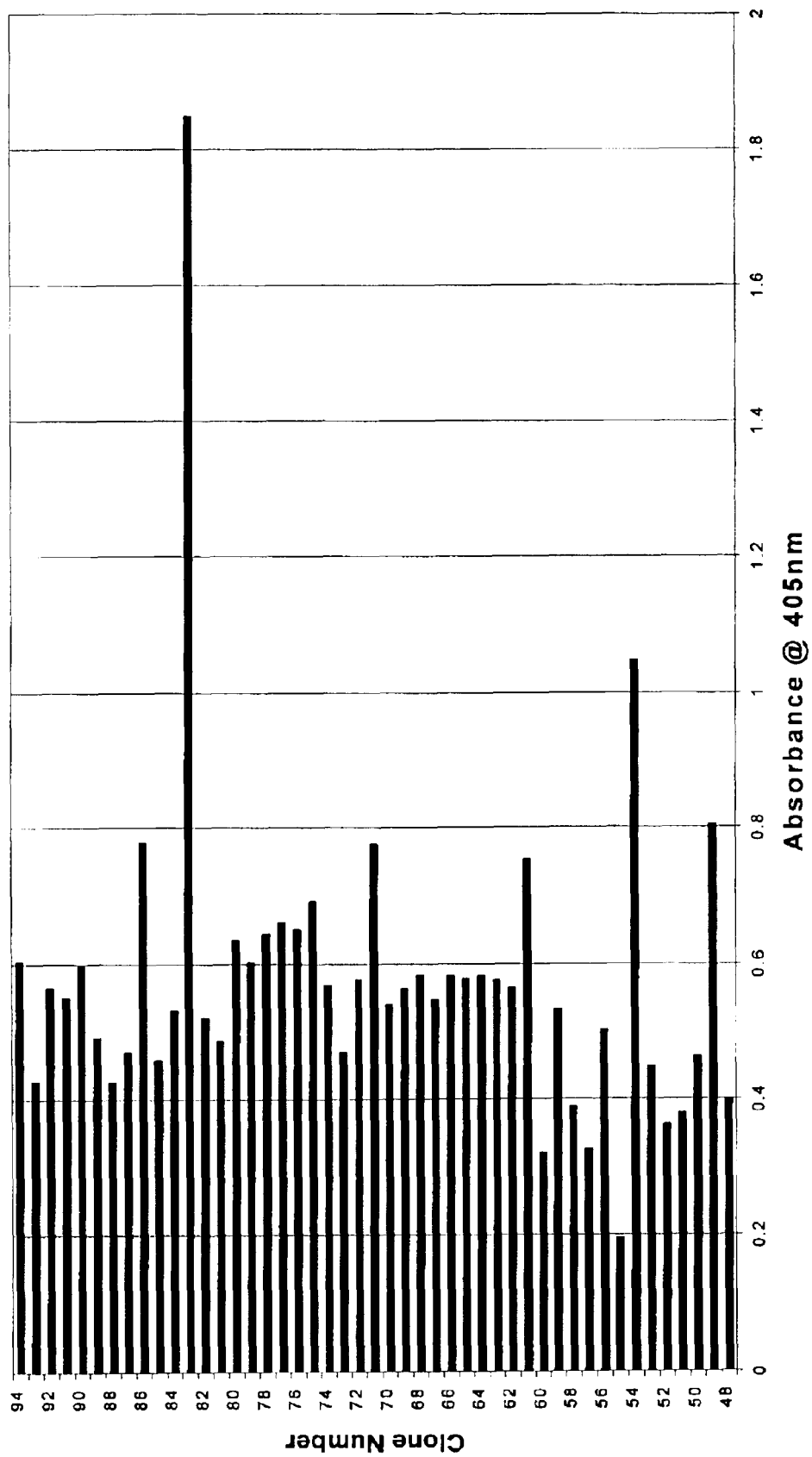

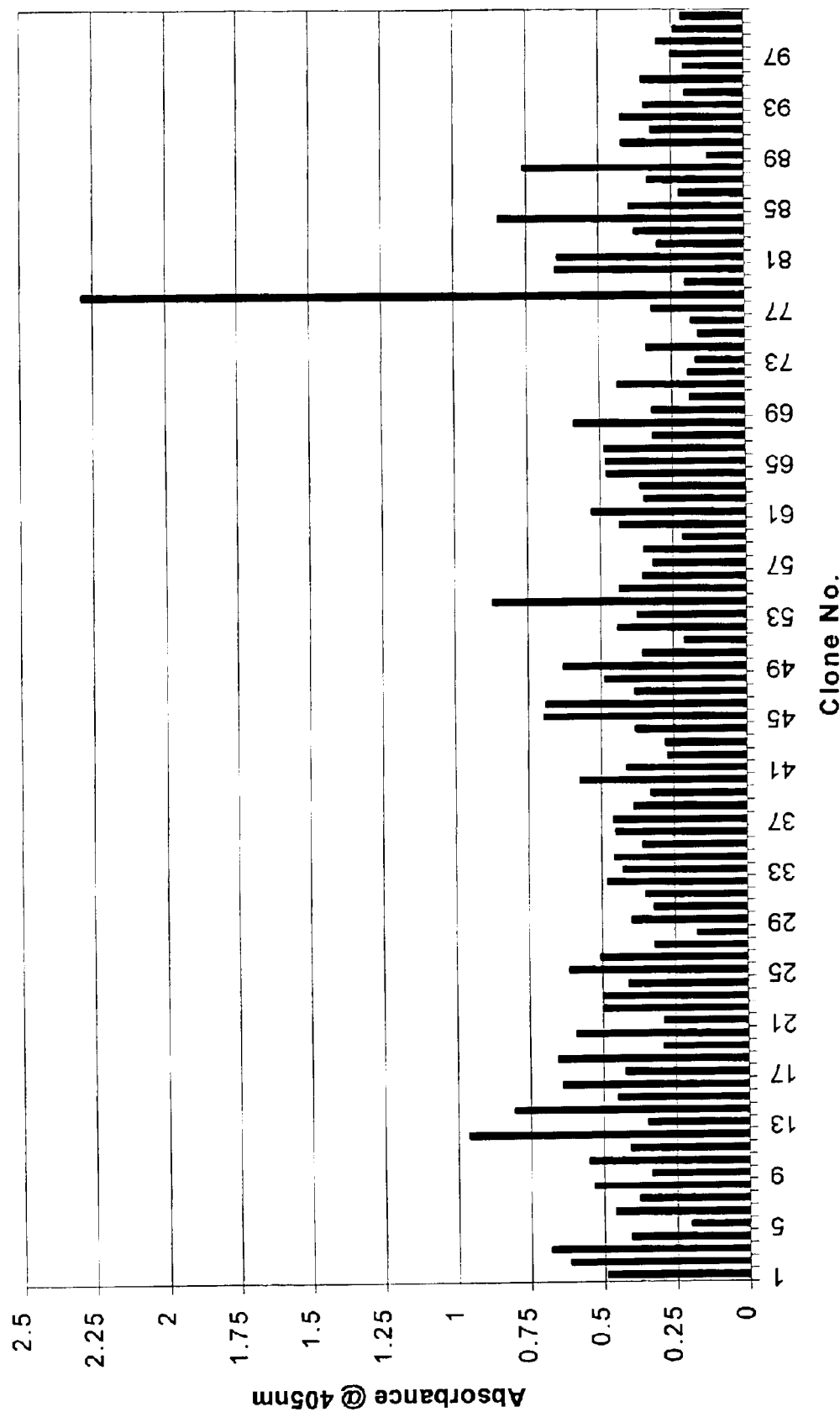

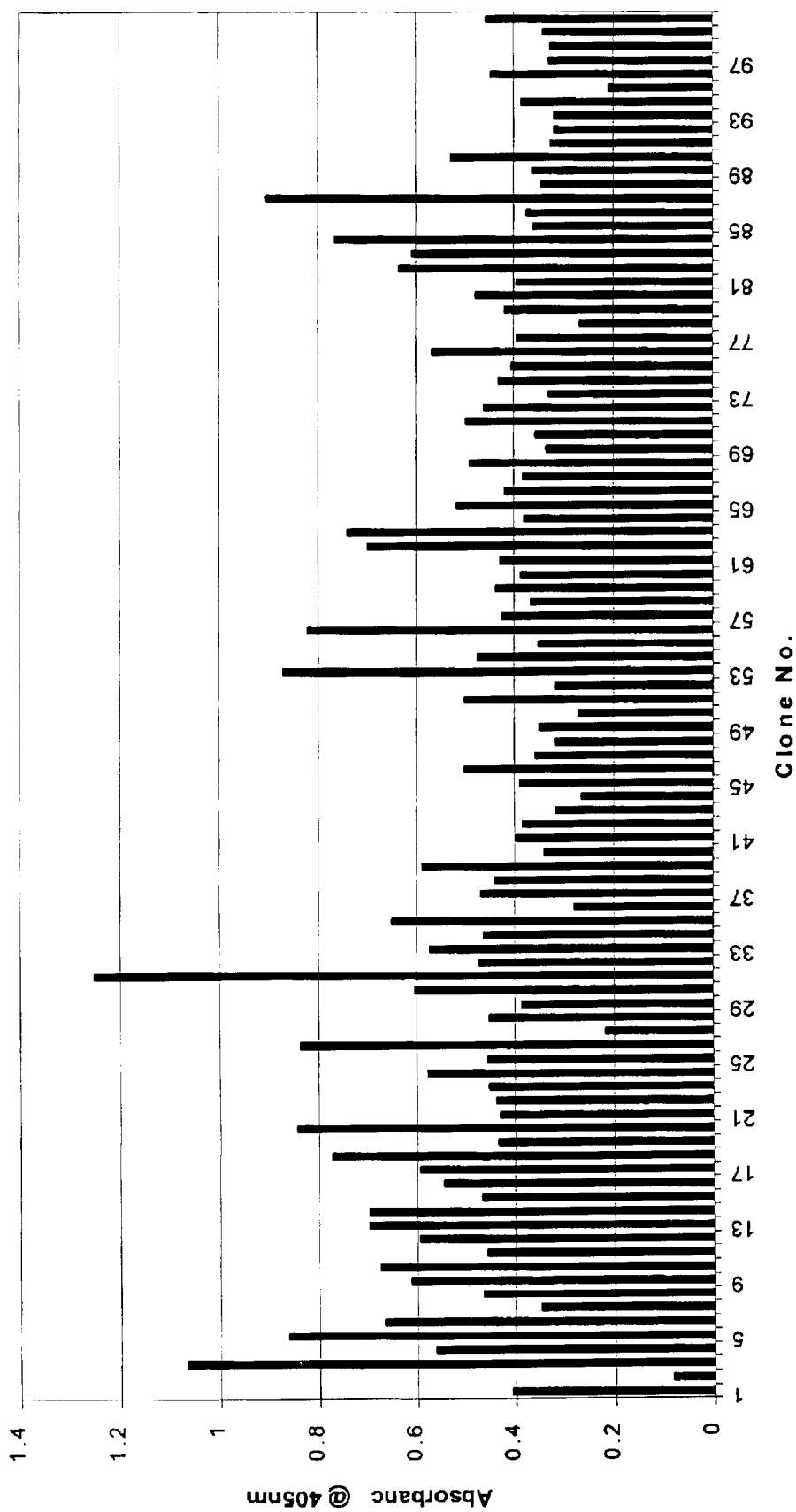
Fig. 3. Phage binding to Rat Peyer's Patch (Rat 3)

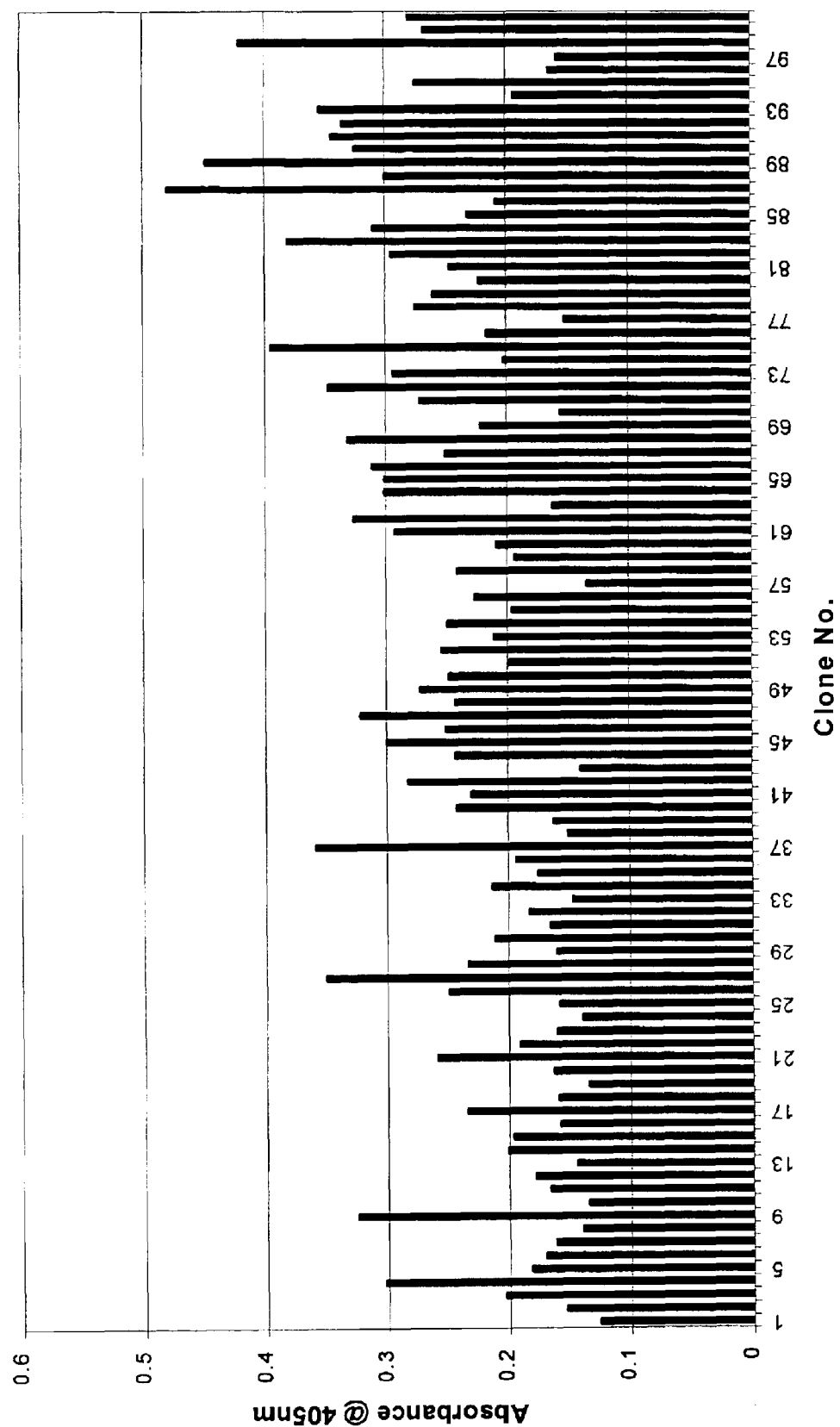
Fig. 4. Phage Binding to Rat Peyer's Patch Homogenate (Rat 4)

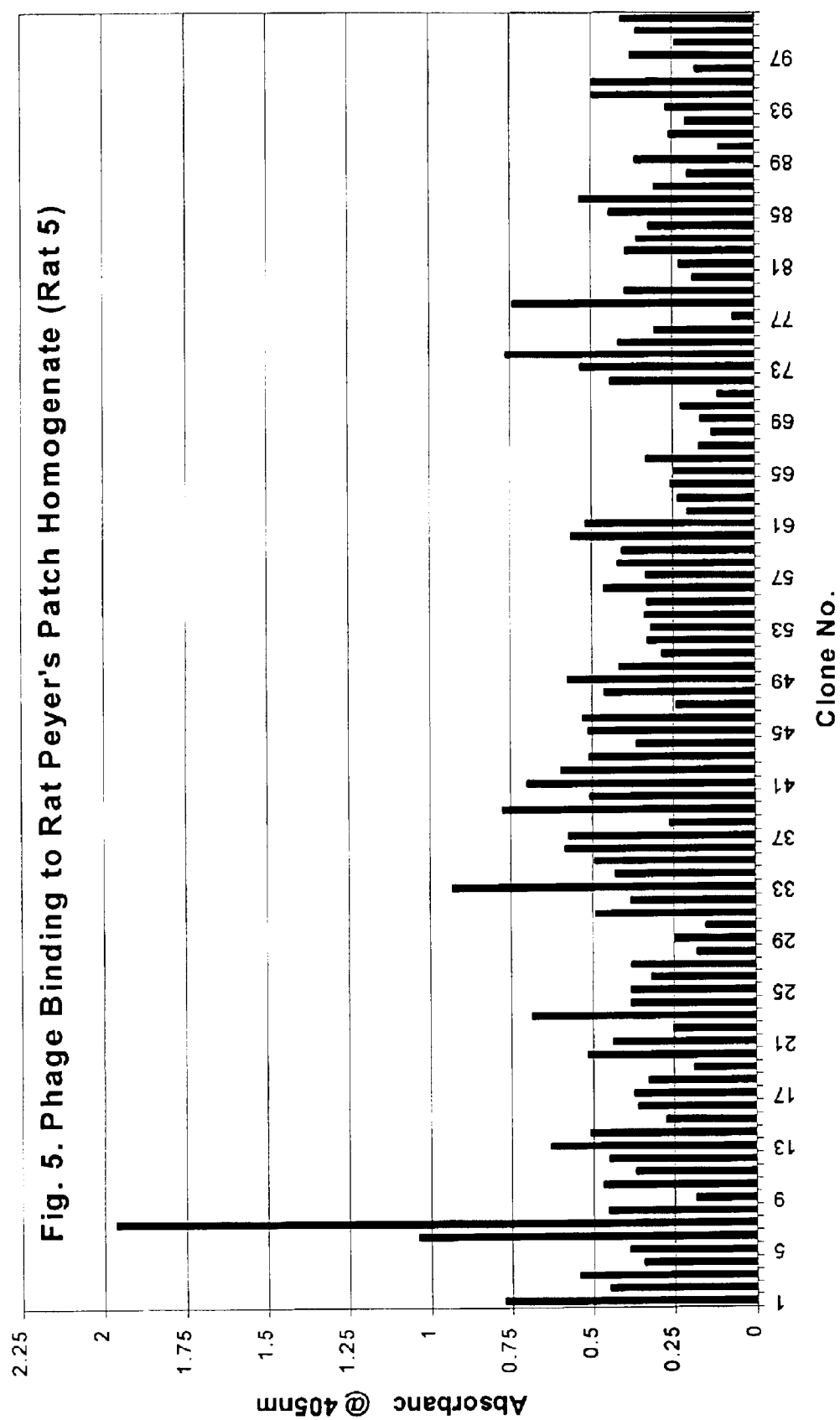

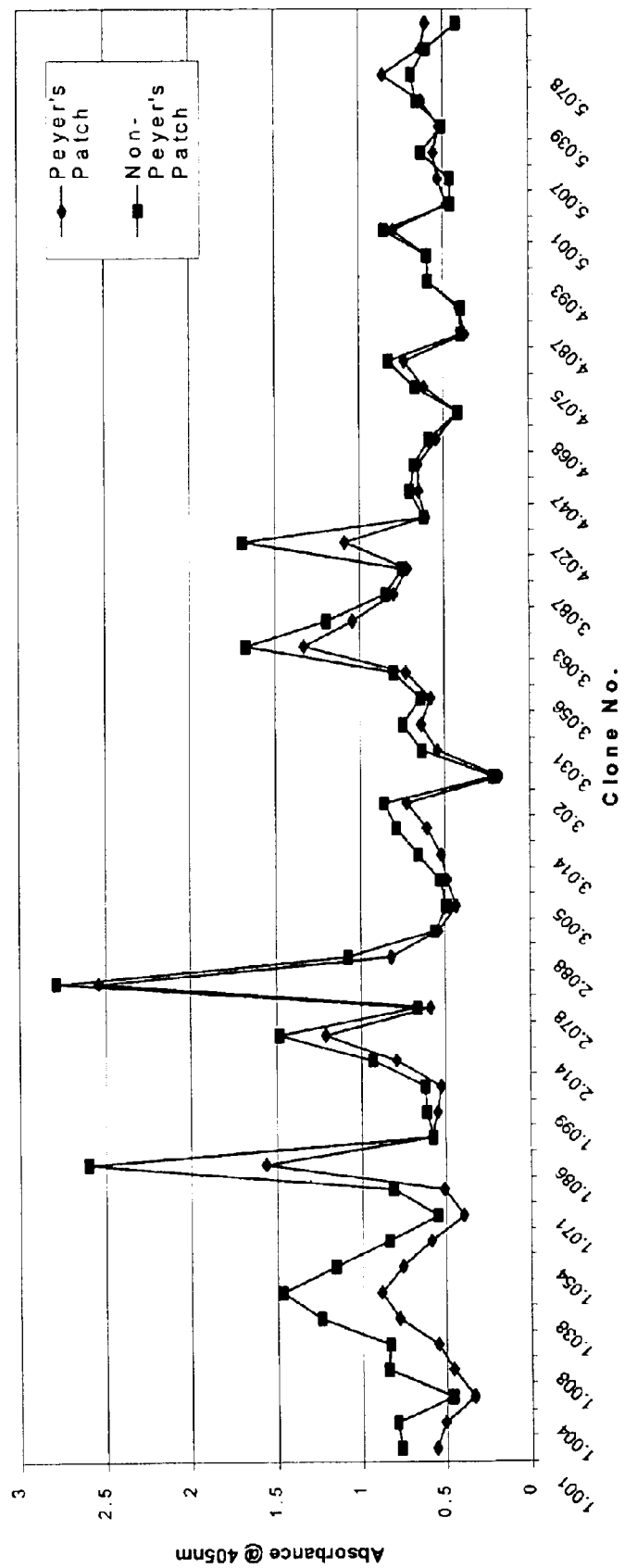

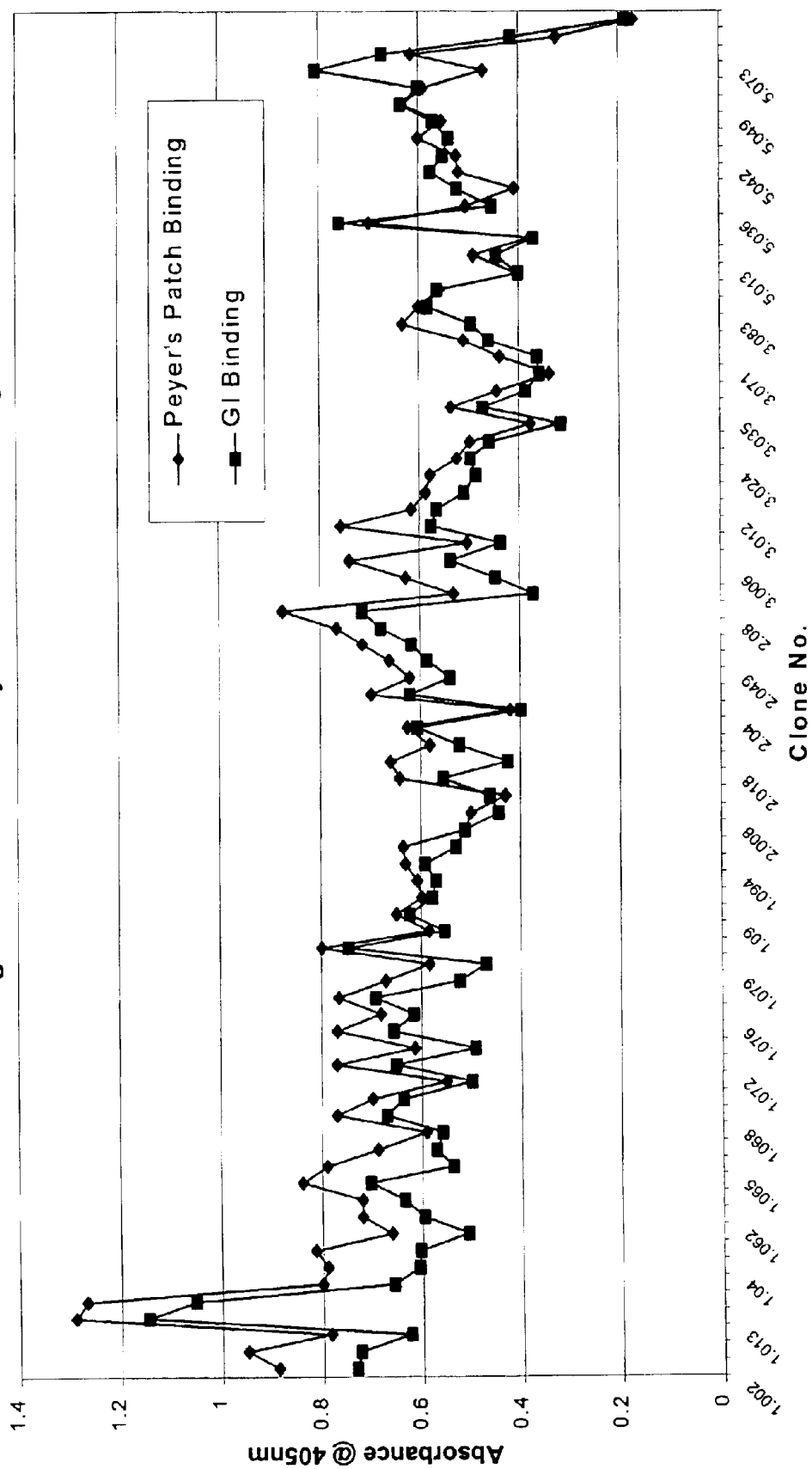

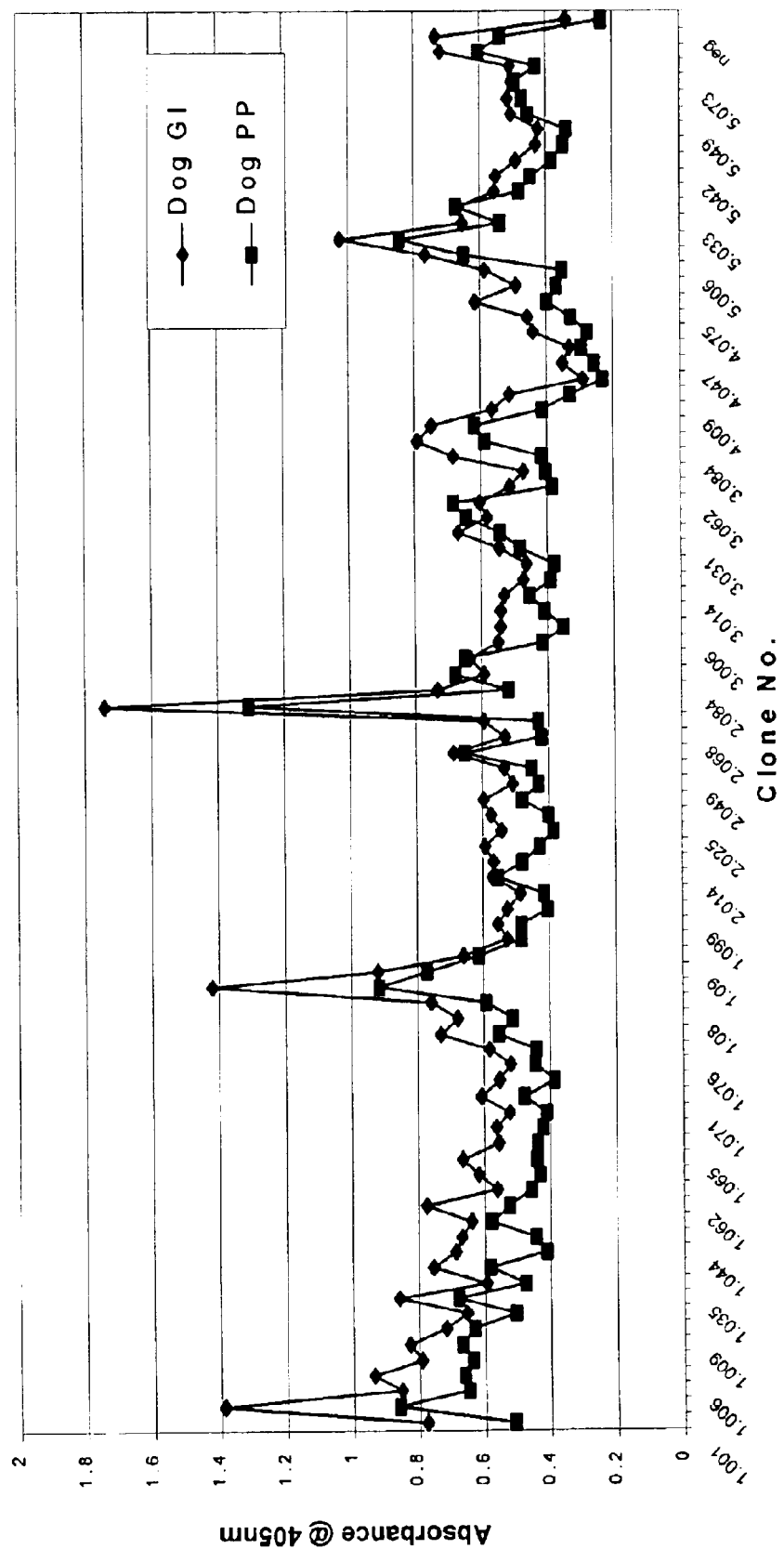
Fig. 8. Comparison of binding to Dog PP homogenates and non-PP homogenates

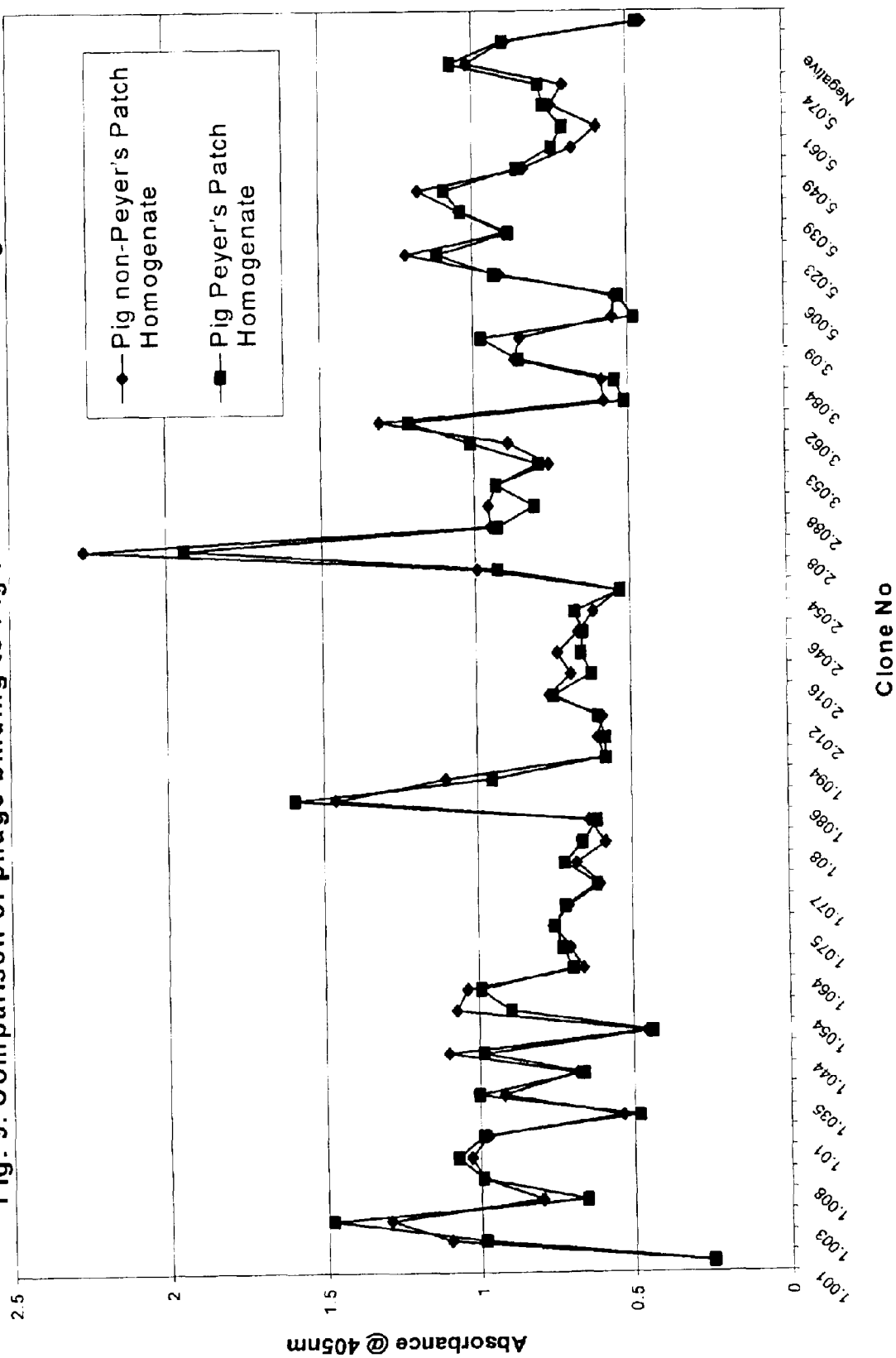
Fig. 9. Comparison of phage binding to Pig PP vs. Non-PP homogenate

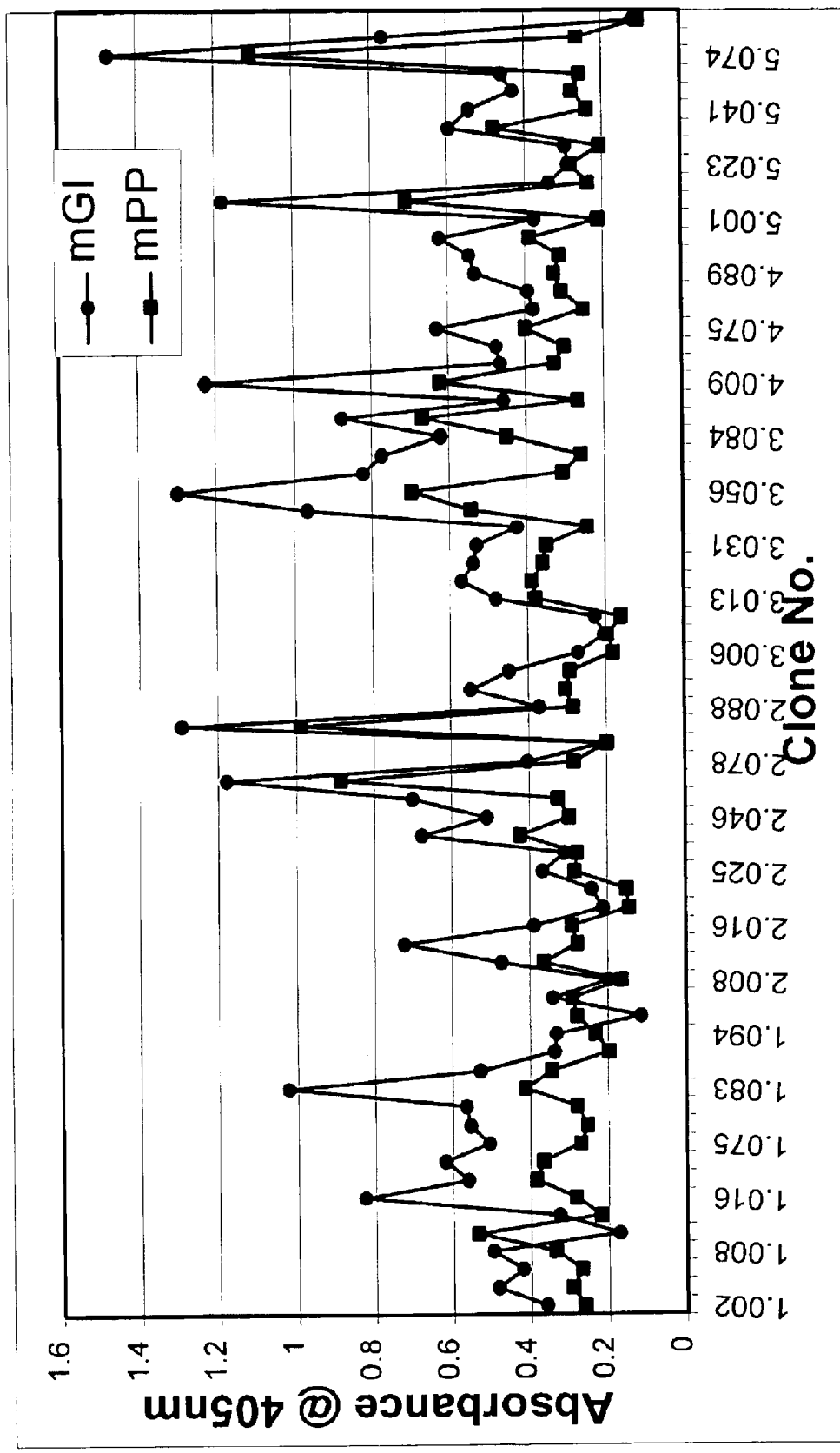
Figure 10. Binding profile of phage clones to mouse PP and non-PP (GI) tissue.

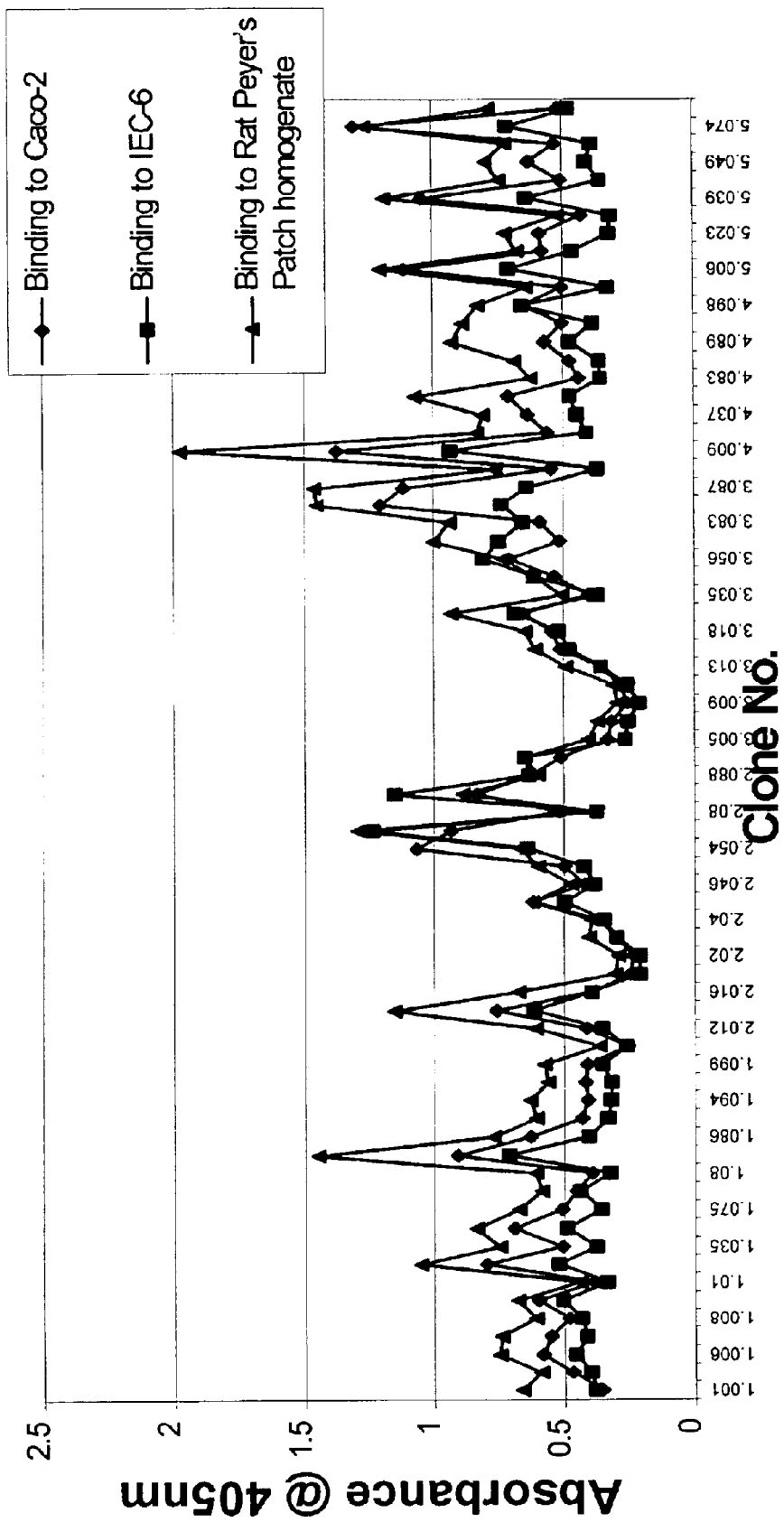
Fig. 11 Binding of Phage clones to Rat PP, Caco-2 and IEC-6

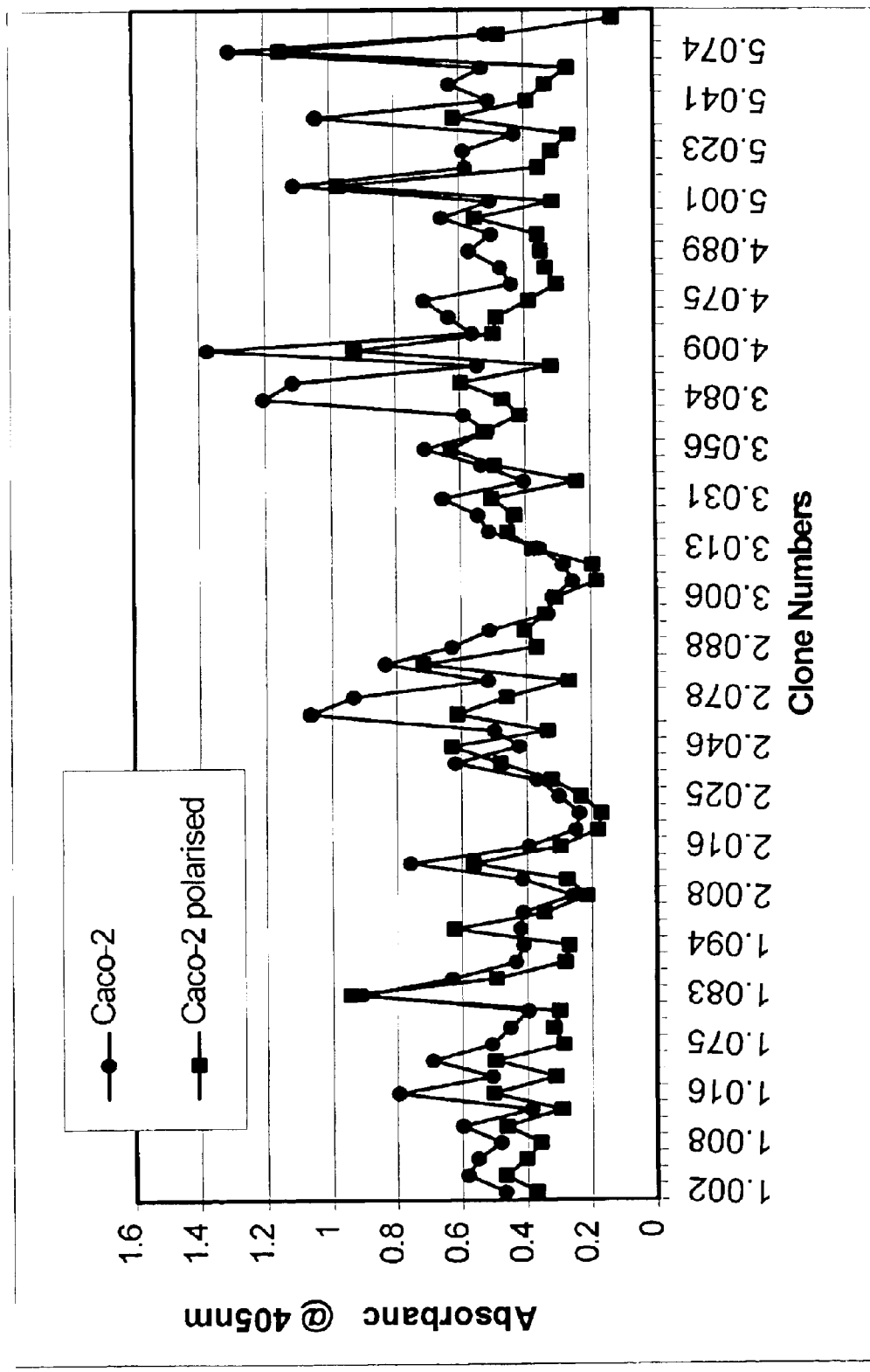
Fig 12. Binding profile of phage clones to differentiated versus non-differentiated Caco-2

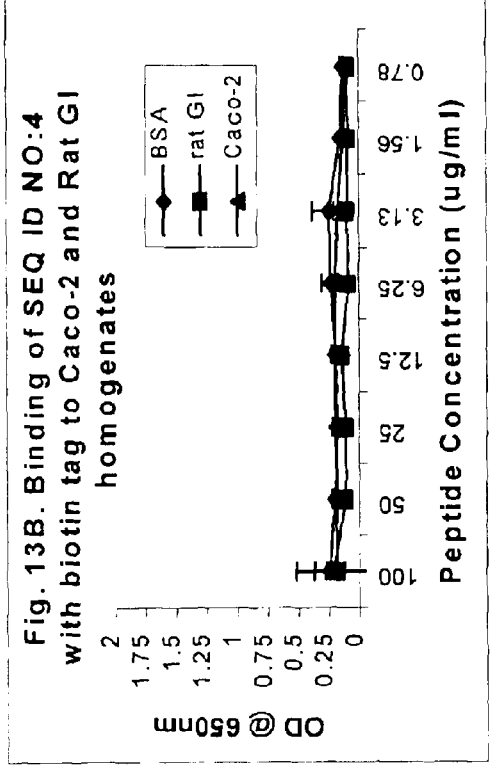
Fig. 13A. Binding of SEQ ID NO:3 with biotin tag to Caco-2 and Rat GI homogenates
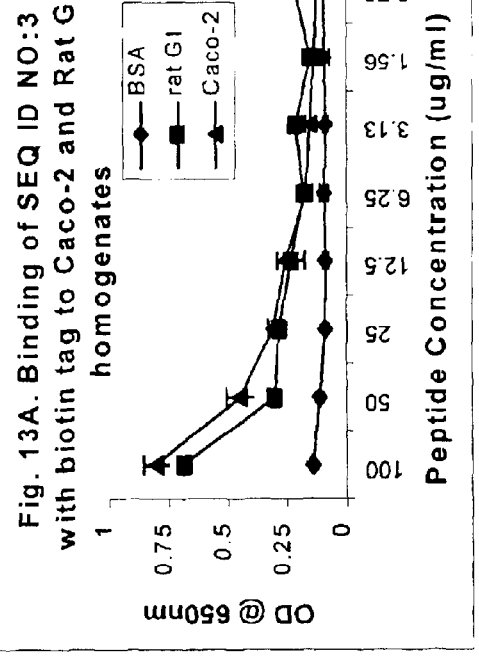
Fig. 13B. Binding of SEQ ID NO:4 with biotin tag to Caco-2 and Rat GI homogenates
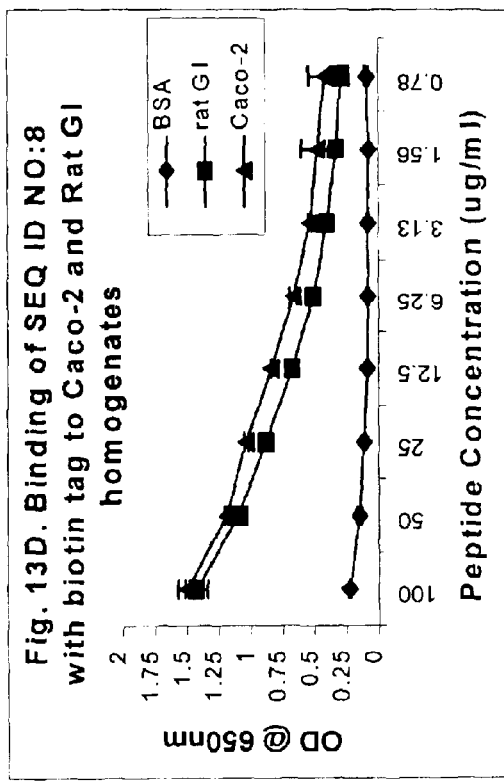
Fig. 13C. Binding of SEQ ID NO:7 with biotin tag to Caco-2 and Rat GI homogenates
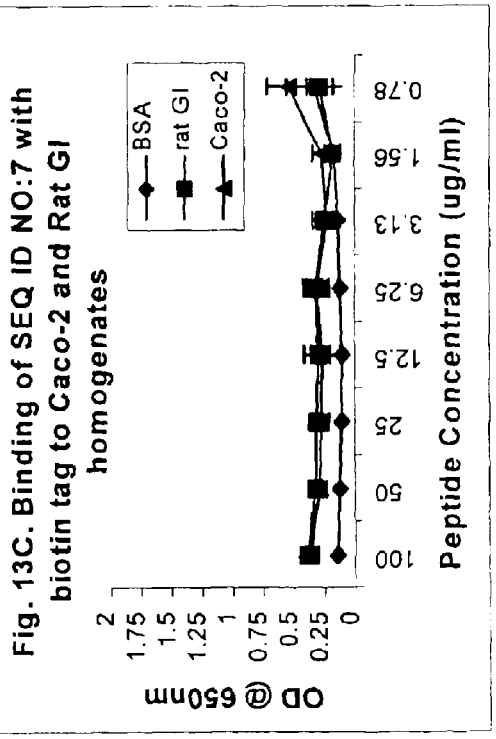
Fig. 13D. Binding of SEQ ID NO:8 with biotin tag to Caco-2 and Rat GI homogenates

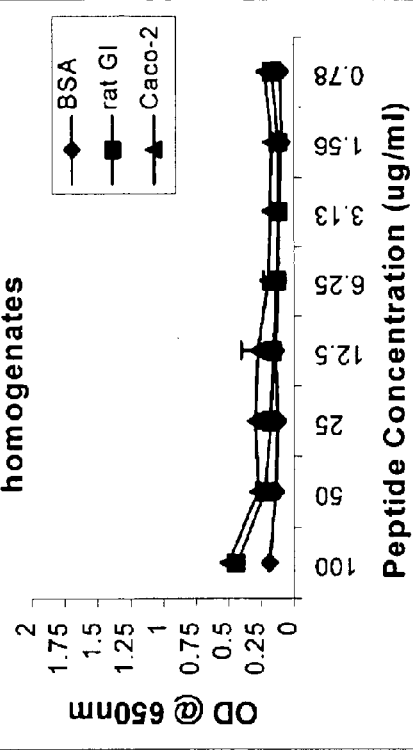
Fig. 13E. Binding of SEQ ID NO:5 with biotin tag to Caco-2 and Rat GI homogenates
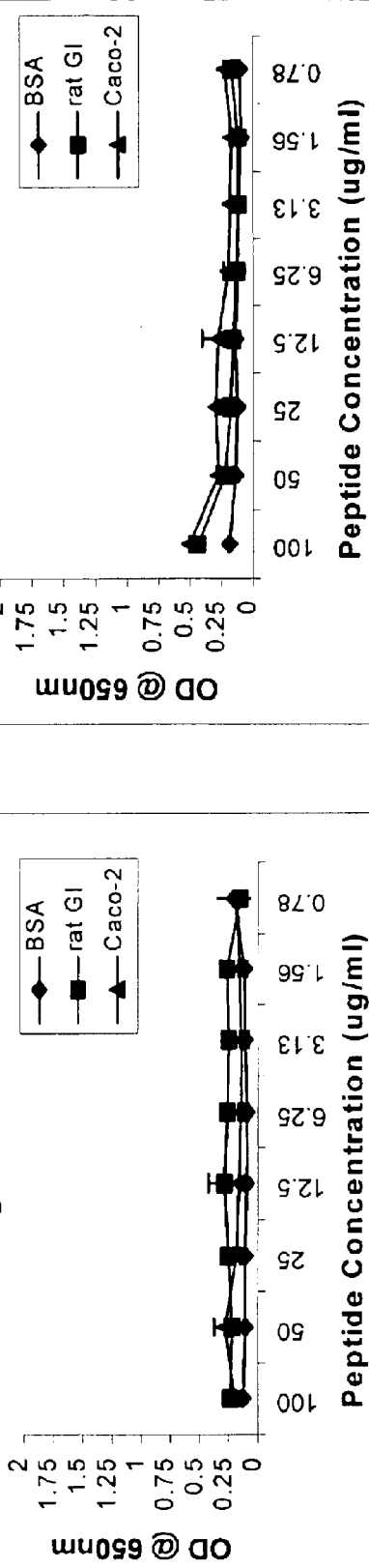
Fig. 13F. Binding of SEQ ID NO:14 with biotin tag to Caco-2 and Rat GI homogenates
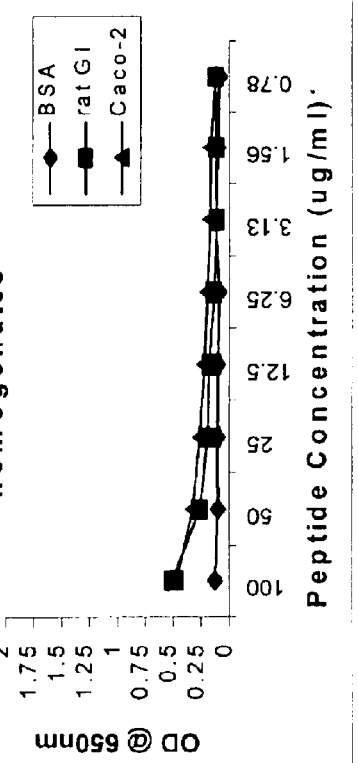
Fig. 13G. Binding of SEQ ID NO:9 with biotin tag to Caco-2 and Rat GI homogenates
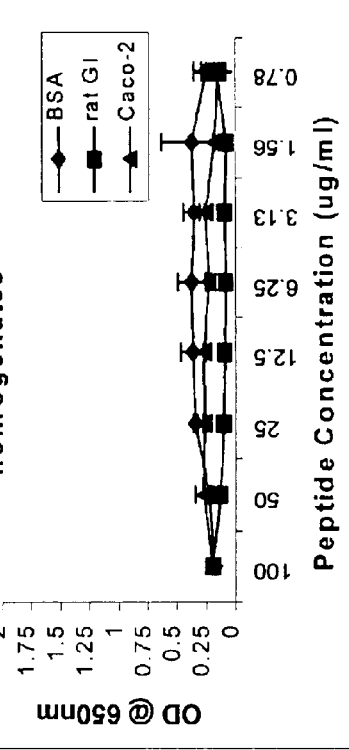
Fig. 13H. Binding of SEQ ID NO:20 with biotin tag to Caco-2 and Rat GI homogenates

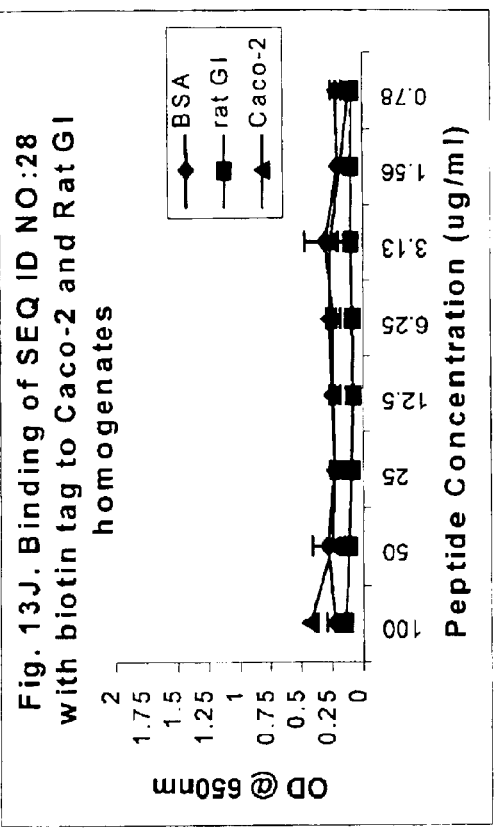
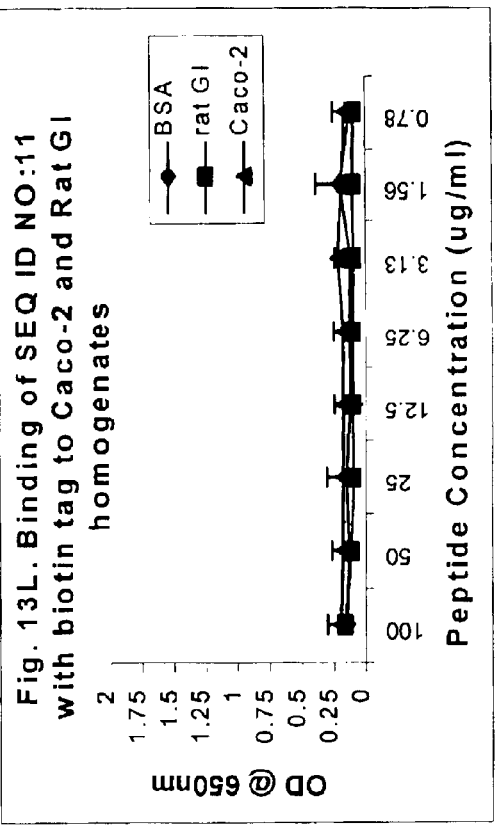
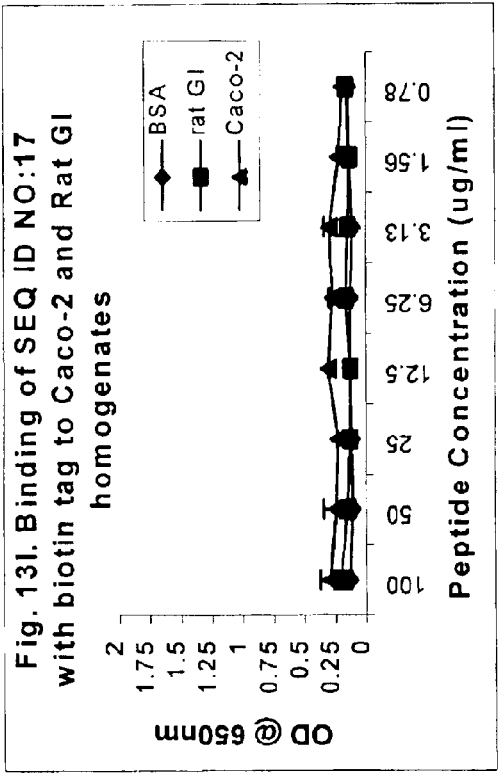
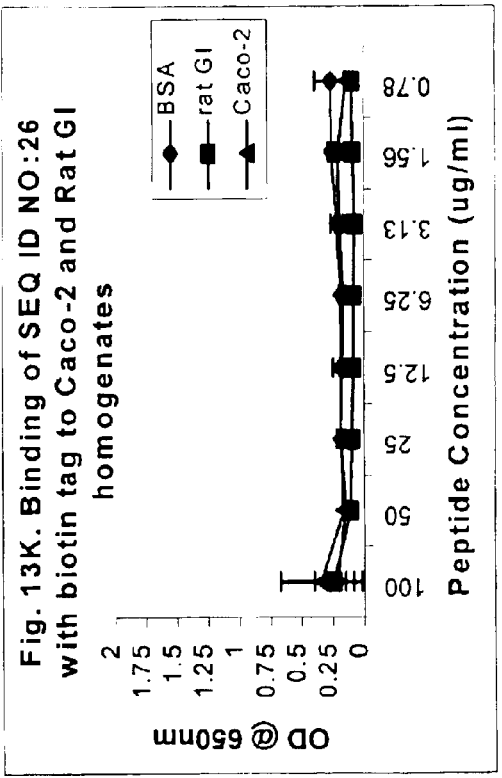

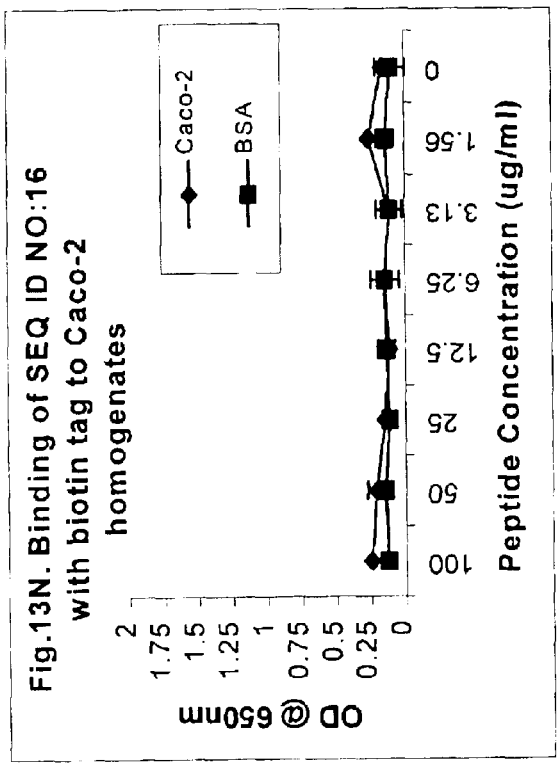
Fig.13N. Binding of SEQ ID NO:16 with biotin tag to Caco-2 homogenates
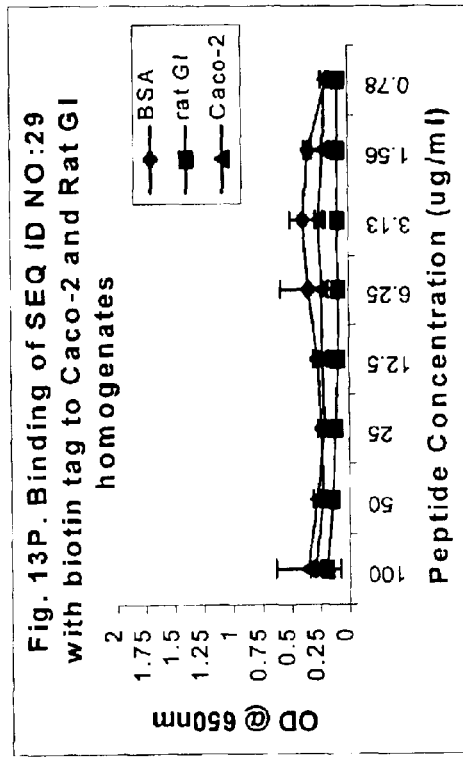
Fig. 13P. Binding of SEQ ID NO:29 with biotin tag to Caco-2 and Rat GI homogenates
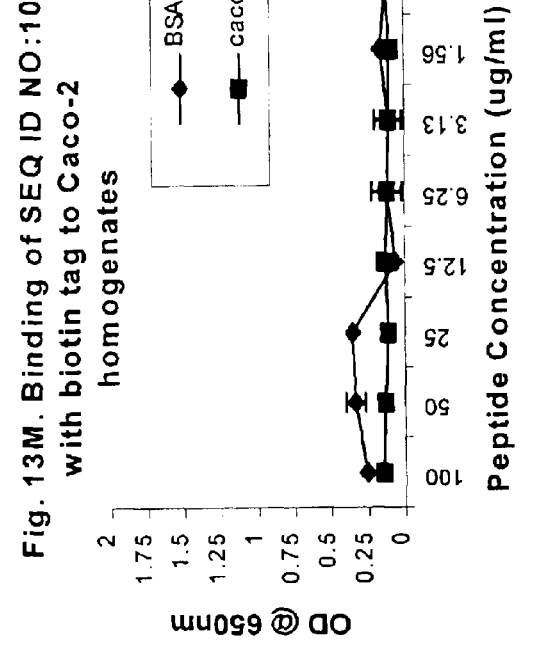
Fig. 13M. Binding of SEQ ID NO:10 with biotin tag to Caco-2 homogenates
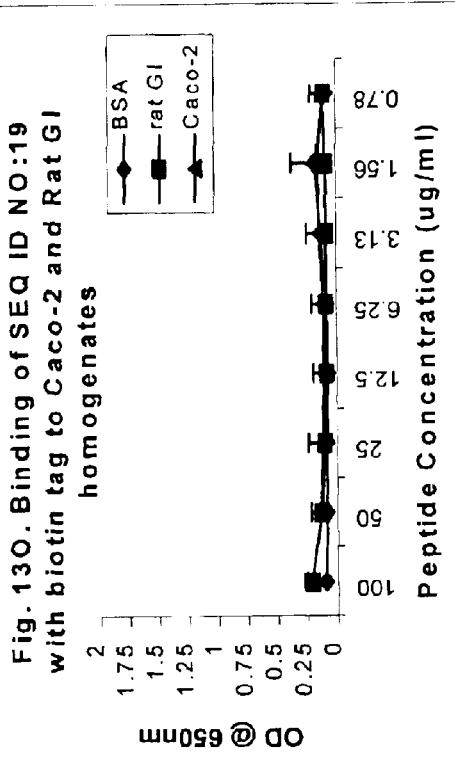
Fig. 13O. Binding of SEQ ID NO:19 with biotin tag to Caco-2 and Rat GI homogenates

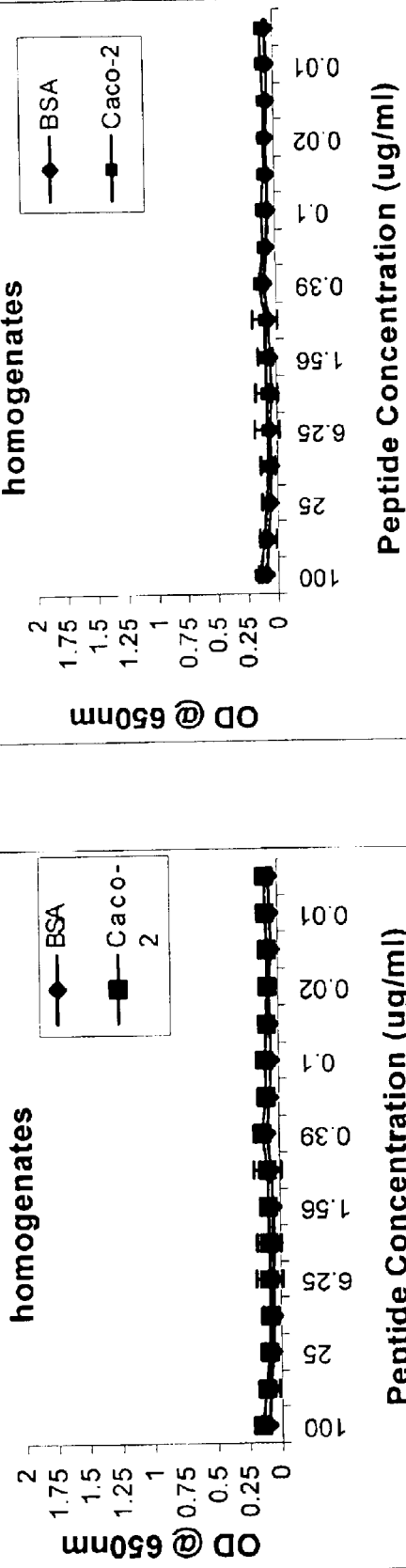
Fig. 13R. Binding of SEQ ID NO:15 with biotin tag to Caco-2 homogenates
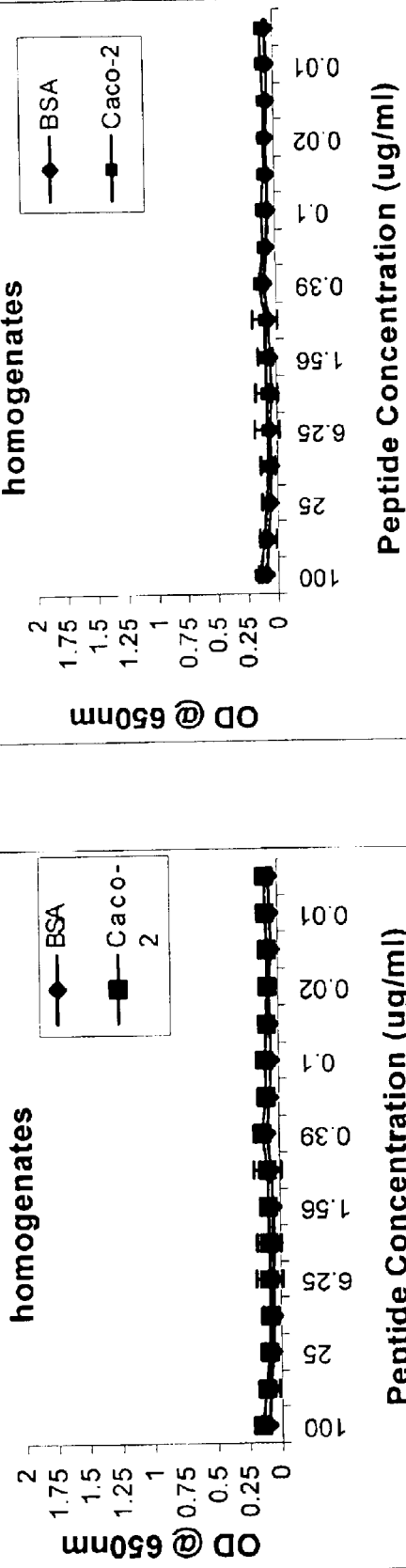
Fig. 13Q. Binding of SEQ ID NO:30 with biotin tag to Caco-2 homogenates

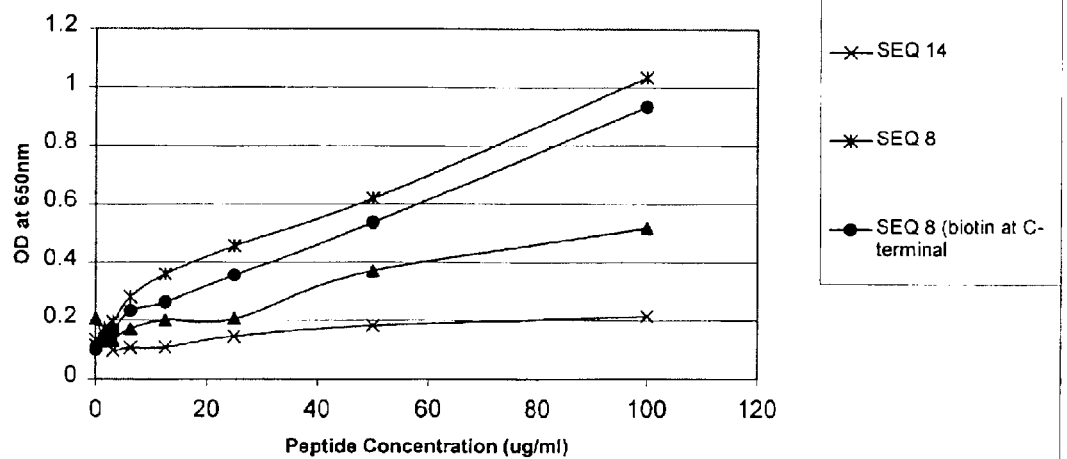
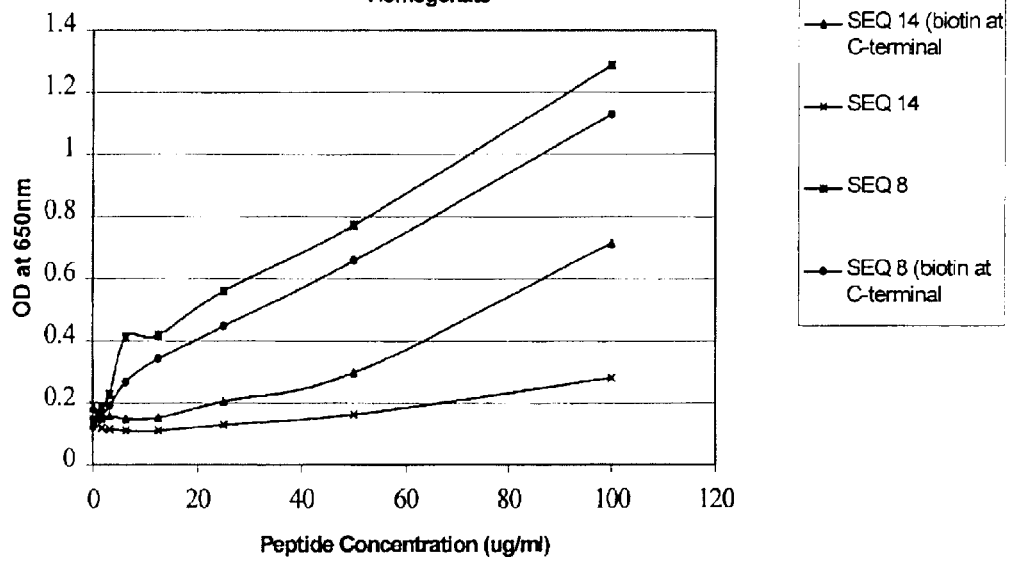

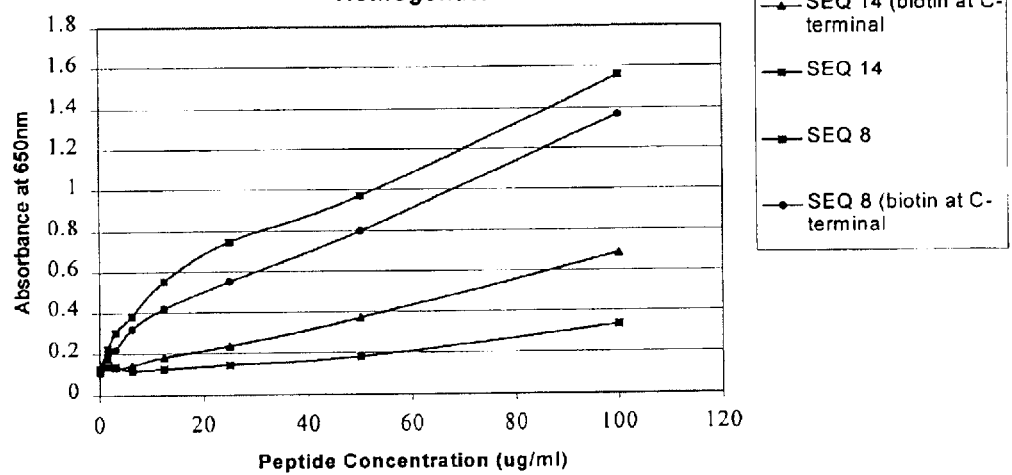
Fig. 14C. Binding of SEQ ID Nos: 8 and 14 with biotin tags to Rat GI Homogenate
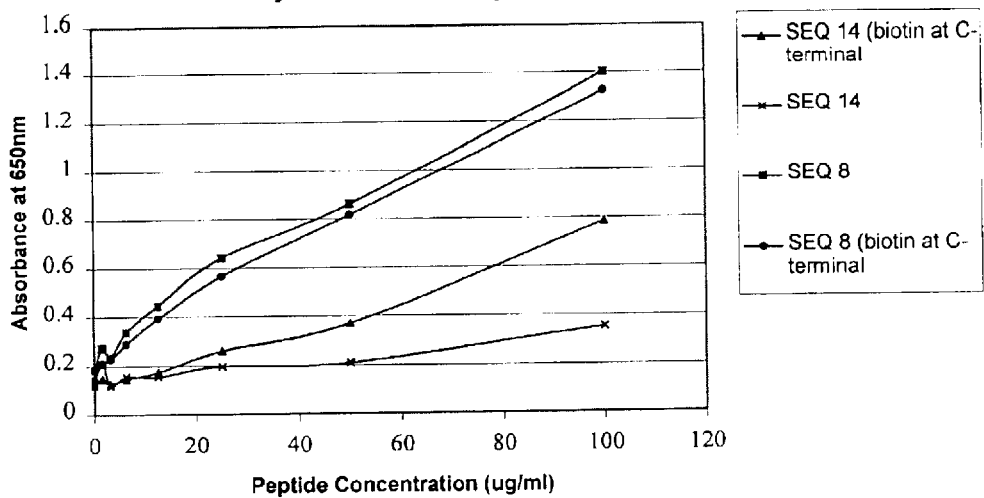
Fig. 14D. Binding of SEQ ID Nos: 8 and 14 with biotin tags to Rat Peyer's Patch Homogenate

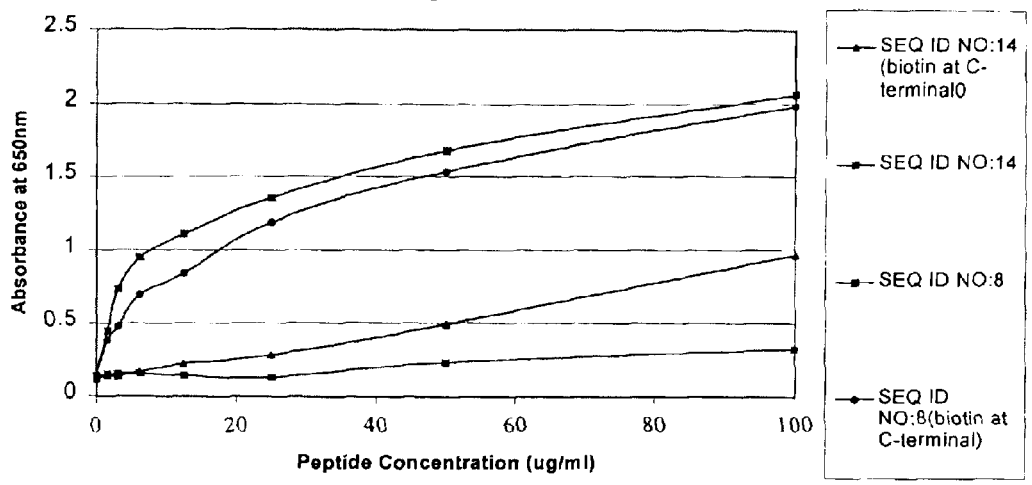
Fig. 14E. Binding of SEQ ID Nos: 8 and 14 with biotin tags to Dog GI Homogenate
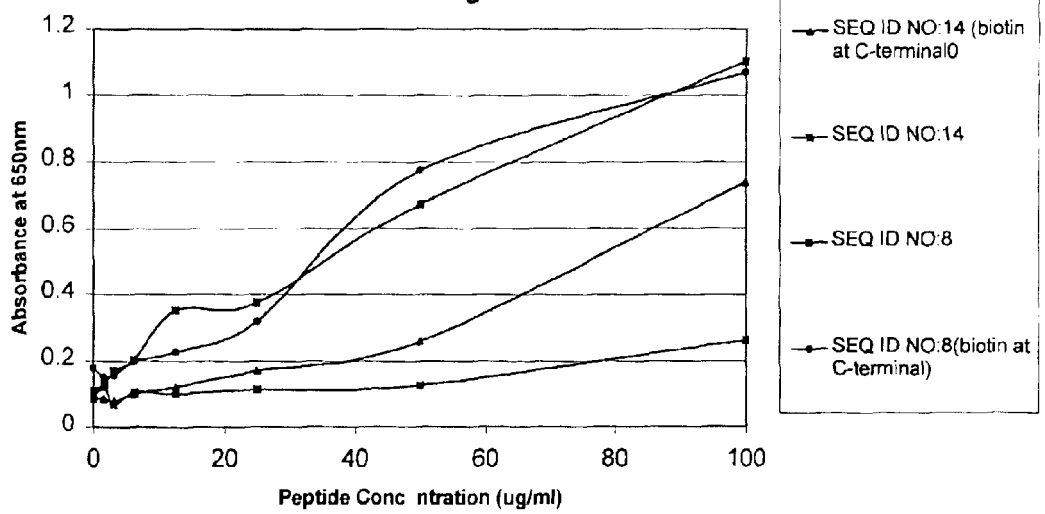
Fig. 14 F. Binding of SEQ ID NOs: 8 and 14 with biotin tags to Dog Peyers's Patch Homogenate

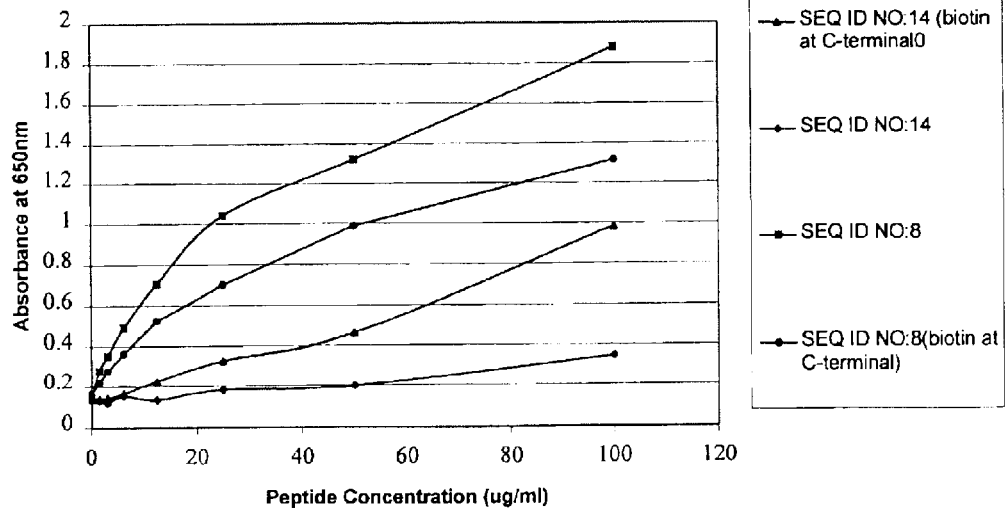
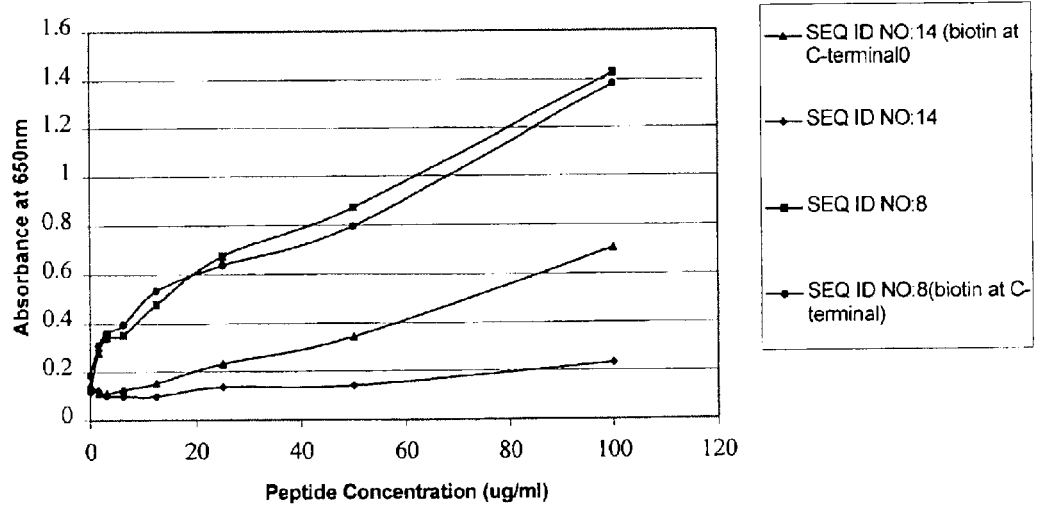

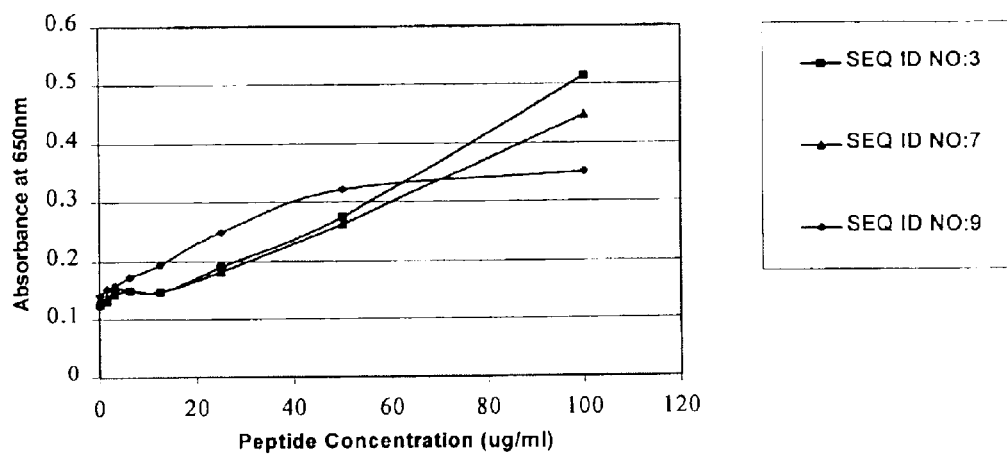
Fig. 14I. Binding of SEQ ID NOs: 3, 7 and 9 to Dog GI Homogenate
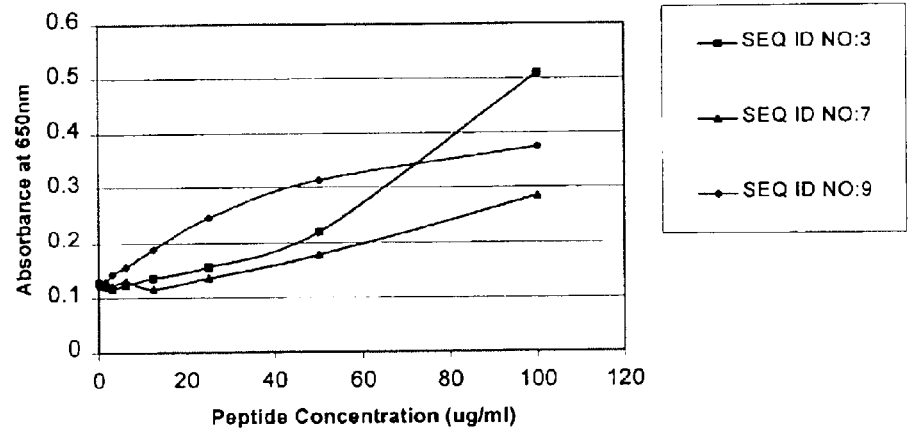
Fig. 14J. Binding of SEQ ID Nos: 3, 7 and 9 with bioin tag to Dog Peyer's Patch Homogenate

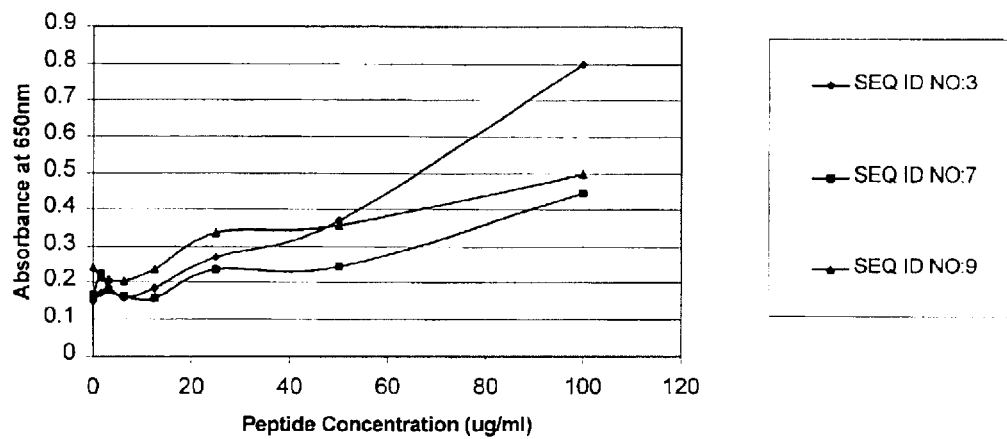
Fig. 14K. Binding of SEQ ID Nos: 3, 7 and 9 with biotin tag to Mouse GI Homogenate
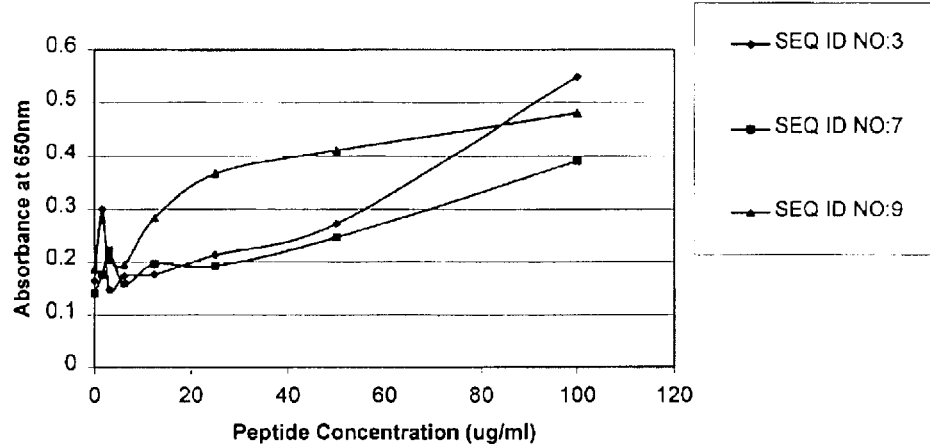
Fig. 14L. Binding of SEQ ID NOs: 3, 7 and 9 with biotin tags to Mouse Peyer's Patch Homogenate

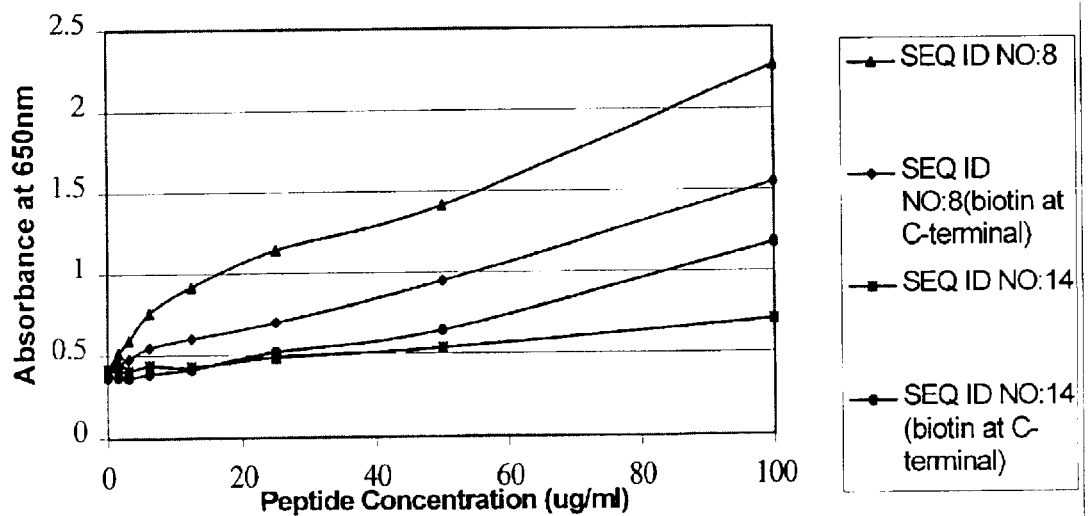
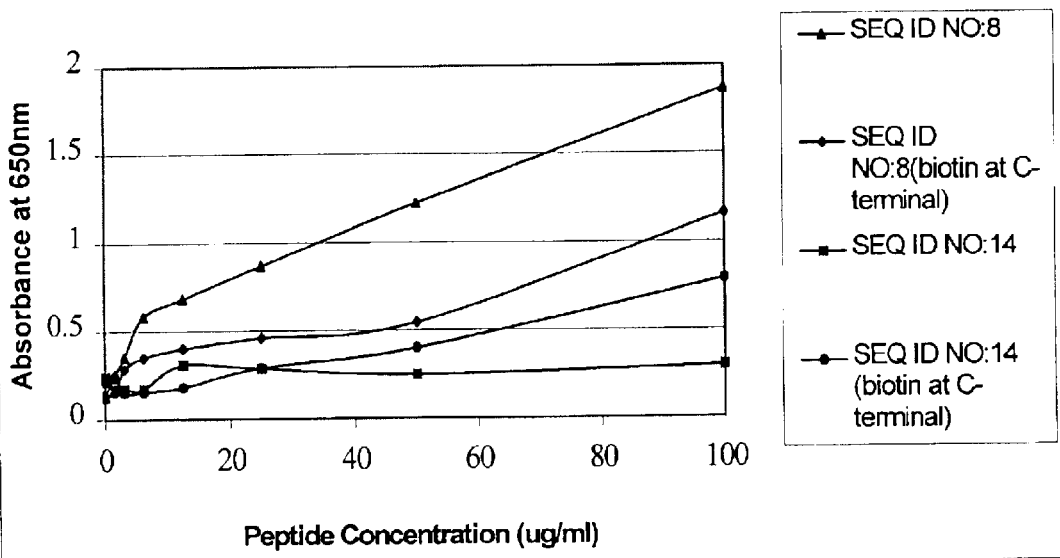

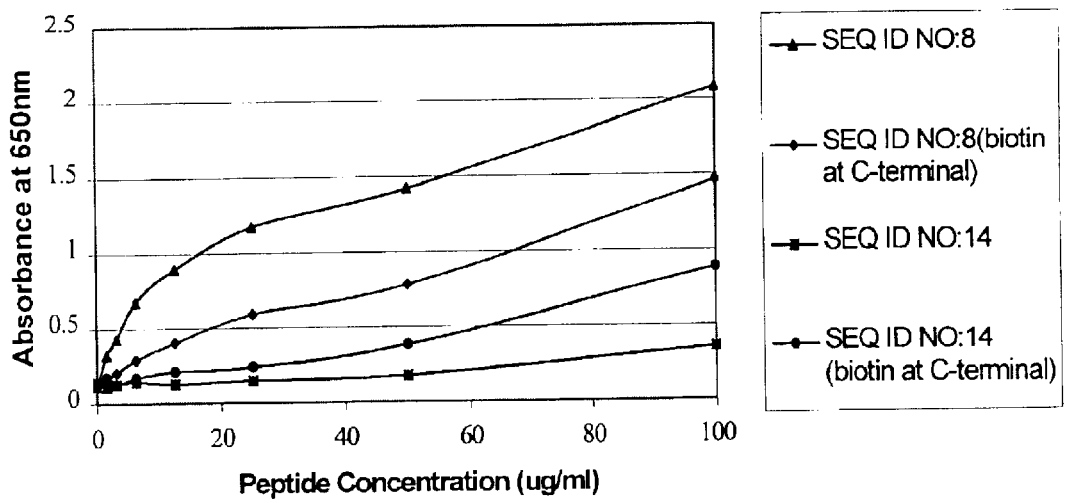
Fig. 15C. Binding of Various Biotinylated Peptides to Rat Lung Tissue Homogenate
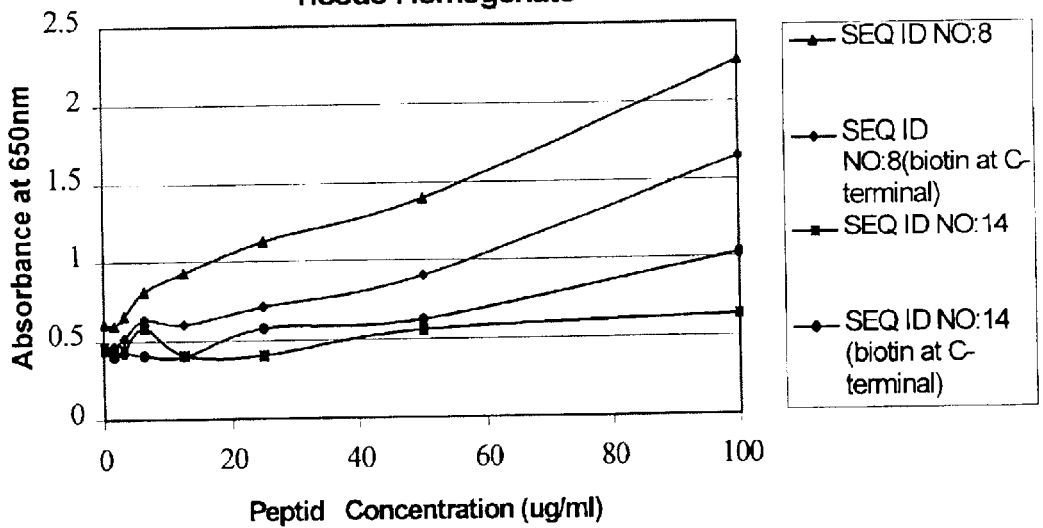
Fig. 15D. Binding of Biotinylated Peptides to Rat Kidney Tissue Homogenate

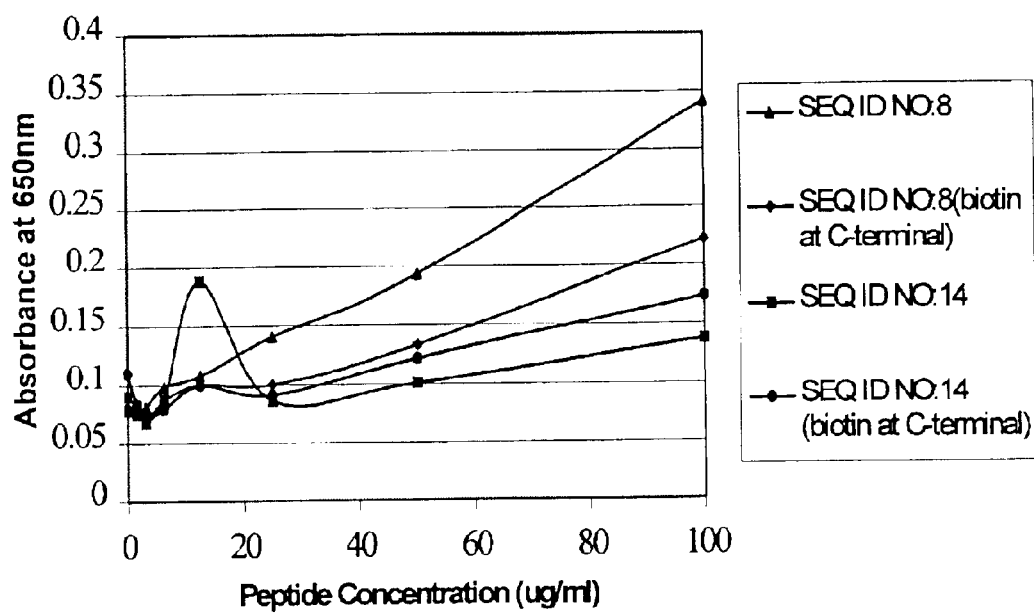

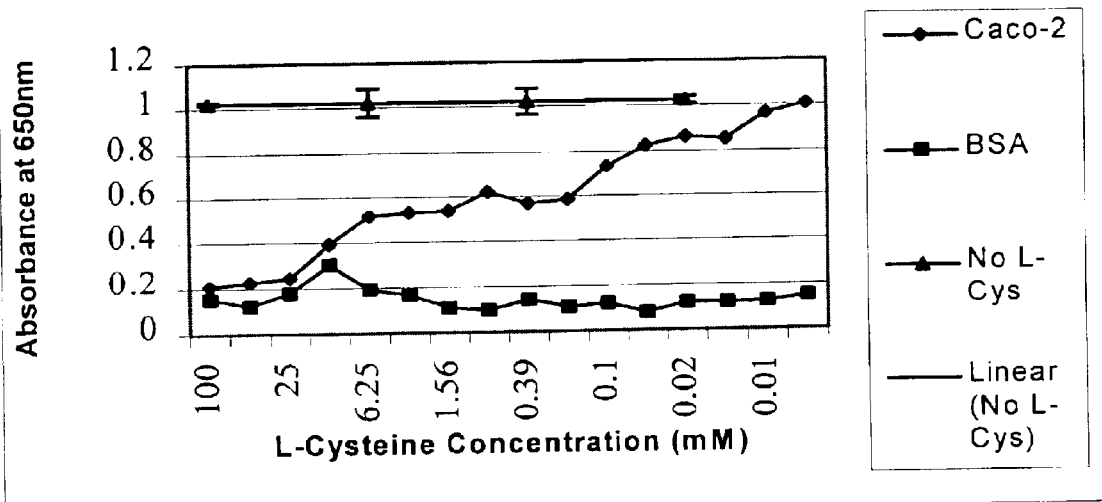
Fig. 16A. Binding of SEQ ID NO:8 (25ug/ml) in the Presence of Free L-Cysteine
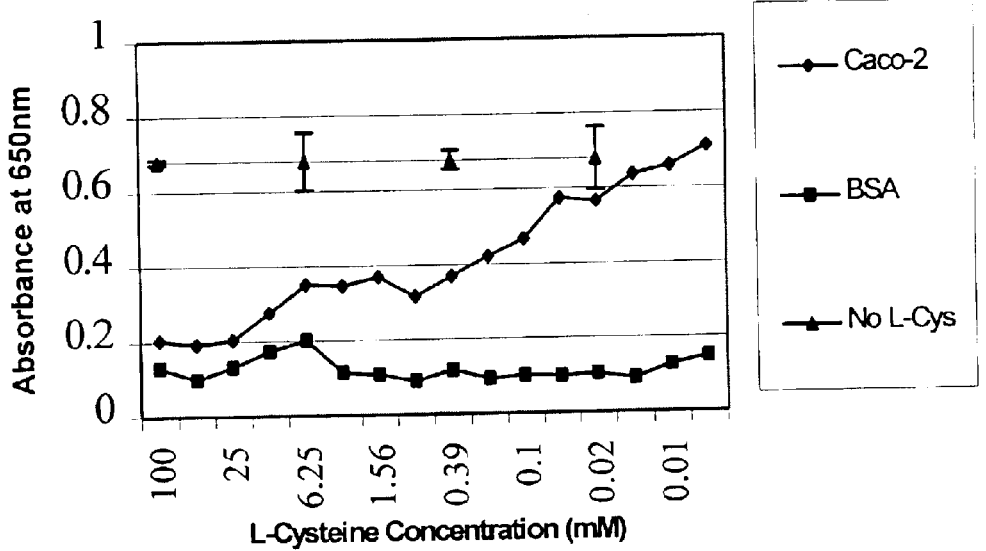
Fig. 16B. Binding of SEQ ID NO:8 (12.5ug/ml) in the Presence of Free L-Cysteine

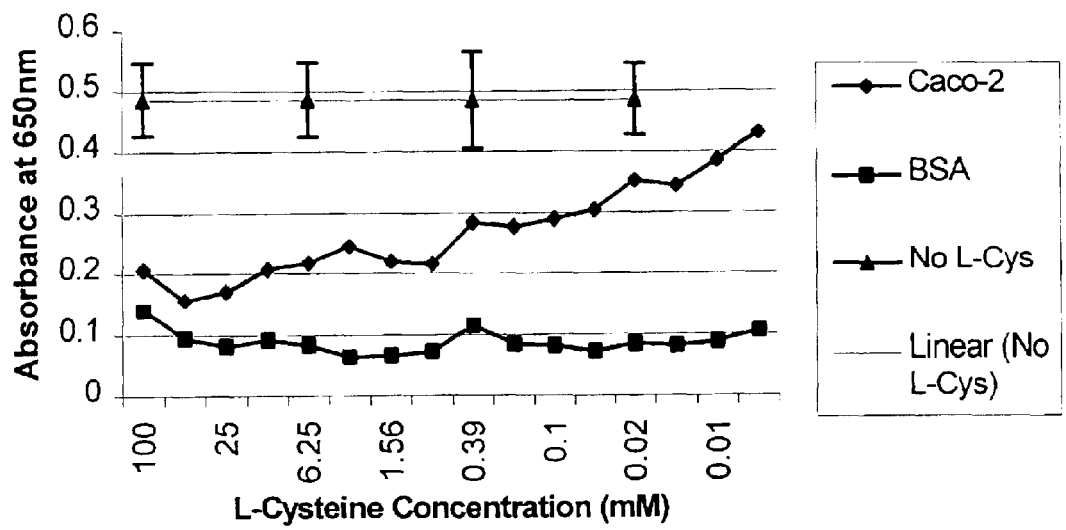
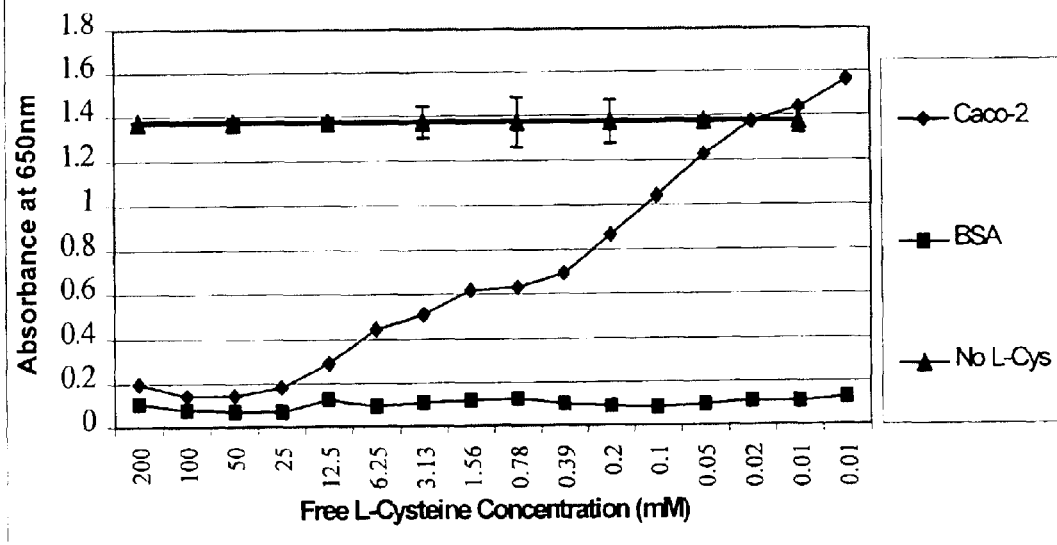

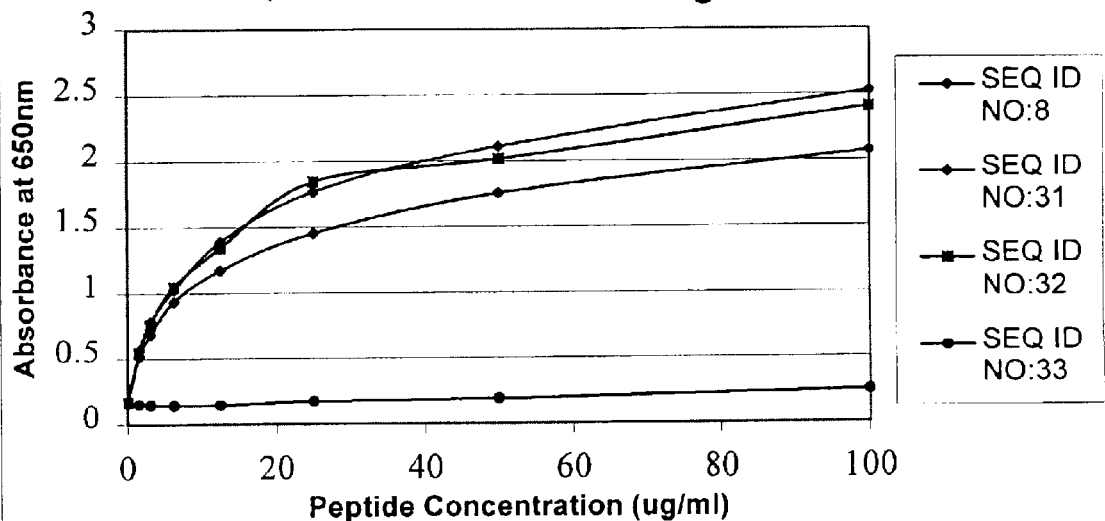
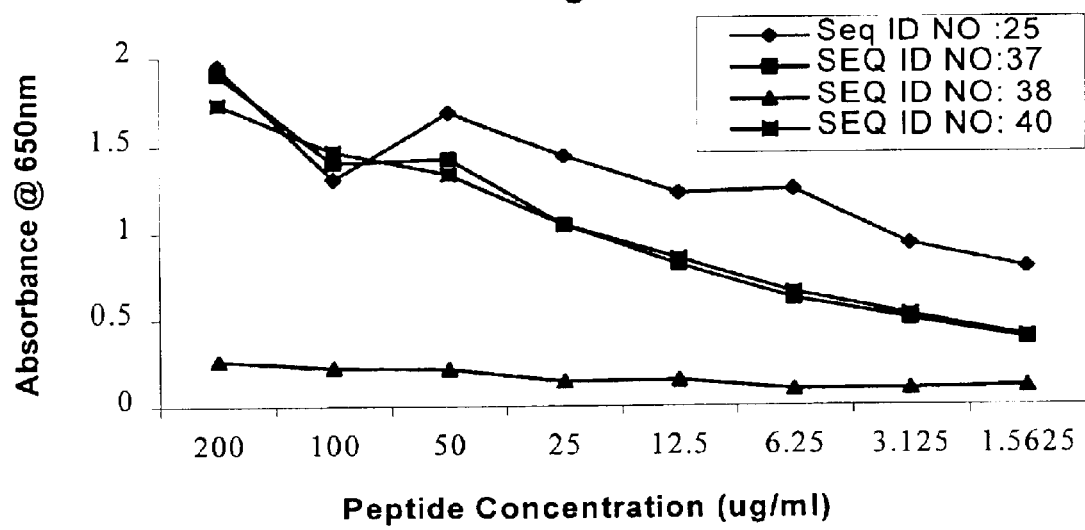

Fig. 18. Binding of zinc-binding derivative of SEQ ID NO:3 to Caco-2 homogenates
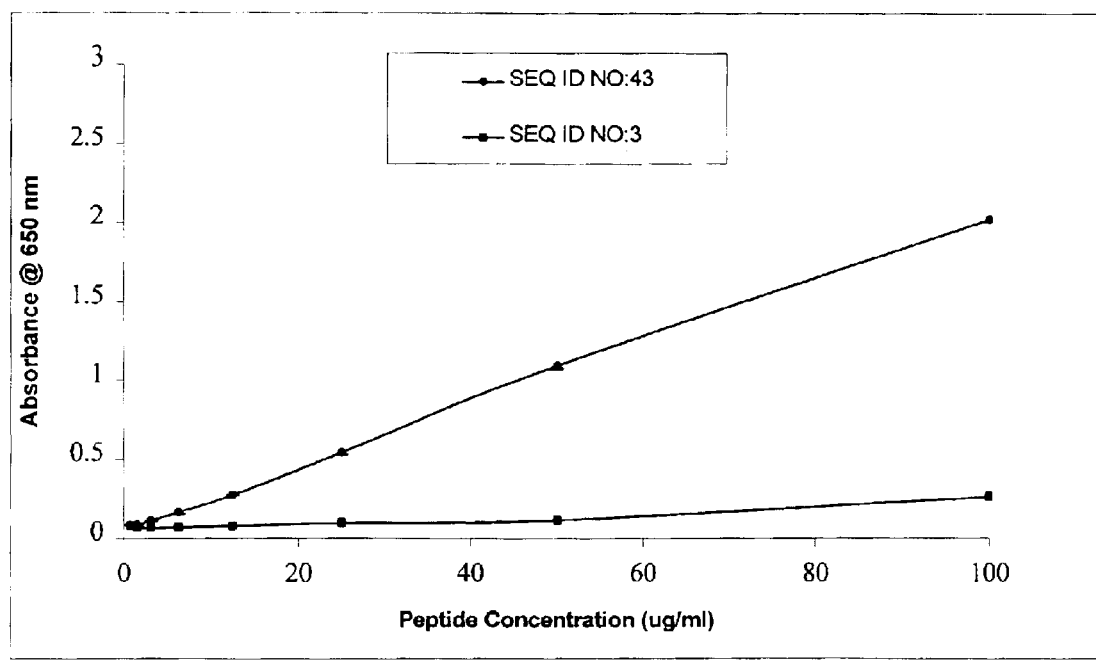

Fig.19A. Binding of peptide-coated particles to Caco-2 homogenates
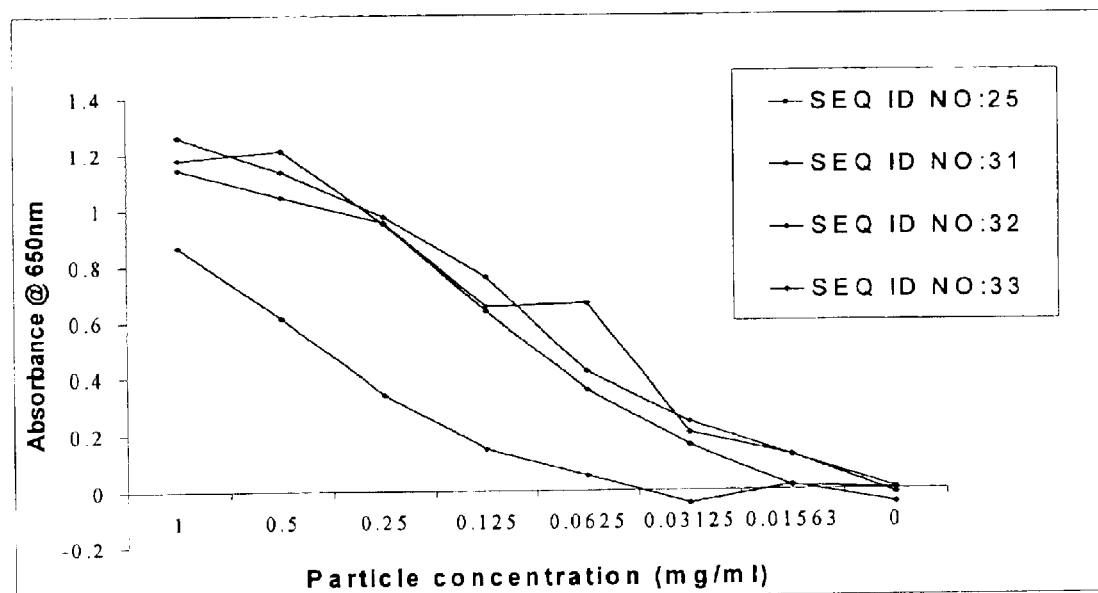
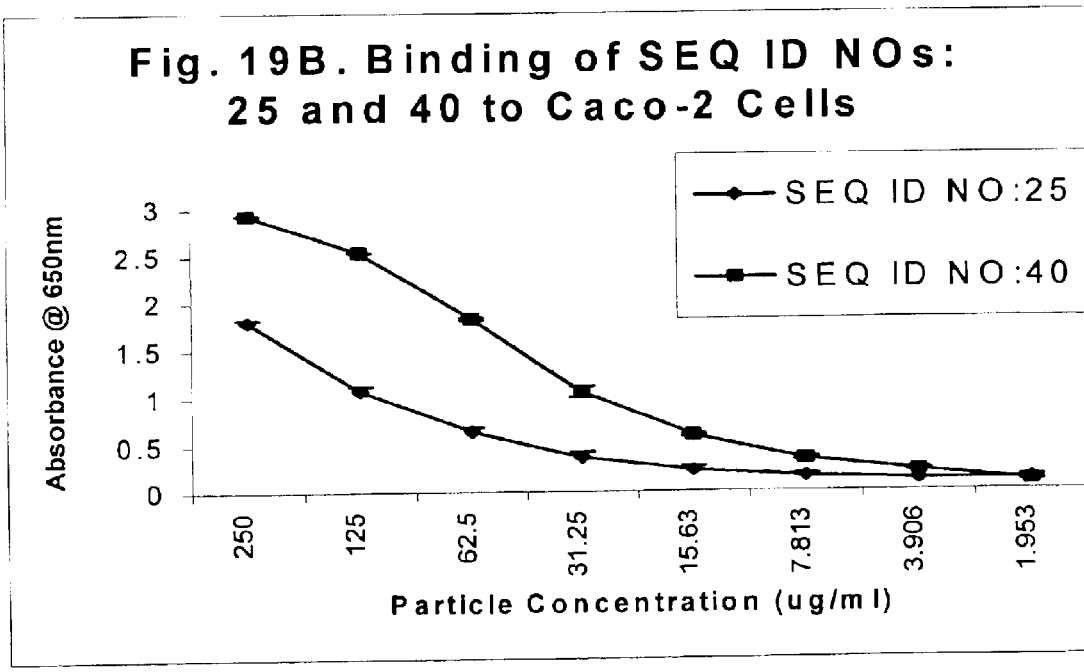

SEQUENCE LISTING

<160> NUMBER OF SEQ ID NOS: 100

<210> SEQ ID NO 1
<211> LENGTH: 12
<212> TYPE: PRT
<213> ORGANISM: Artificial Sequence
<220> FEATURE:
<223> OTHER INFORMATION: polypeptide ligand

<400> SEQUENCE: 1

Ala Thr Pro Pro Pro Trp Leu Leu Arg Thr Ala Pro
1               5                   10

<210> SEQ ID NO 2
<211> LENGTH: 12
<212> TYPE: PRT
<213> ORGANISM: Artificial Sequence
<220> FEATURE:
<223> OTHER INFORMATION: polypeptide ligand

<400> SEQUENCE: 2

Asp Gly Ser Ile His Lys Arg Asn Ile Met Pro Leu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: polypeptide ligand

<400> SEQUENCE: 3

Asp Tyr Asp Ser Leu Ser Trp Arg Ser Thr Leu His
1               5                   10

<210> SEQ ID NO 4
<211> LENGTH: 12
<212> TYPE: PRT
<213> ORGANISM: Artificial Sequence
<220> FEATURE:
<223> OTHER INFORMATION: polypeptide ligand

<400> SEQUENCE: 4

Gly Glu Pro Thr Thr Asp Met Arg Trp Arg Asn Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: polypeptide ligand

<400> SEQUENCE: 5

Gly Leu Trp Pro Trp Asn Pro Val Thr Val Leu Pro
1               5                   10

<210> SEQ ID NO 6
<211> LENGTH: 12
<212> TYPE: PRT
<213> ORGANISM: Artificial Sequence
<220> FEATURE:
<223> OTHER INFORMATION: polypeptide ligand

<400> SEQUENCE: 6

```
His Met Leu Asn Asp Pro Thr Pro Pro Tyr Trp
1               5                   10

<210> SEQ ID NO 7
<211> LENGTH: 12
<212> TYPE: PRT
<213> ORGANISM: Artificial Sequence
<220> FEATURE:
<223> OTHER INFORMATION: polypeptide ligand

<400> SEQUENCE: 7

Lys Pro Ala Tyr Thr His Glu Tyr Arg Trp Leu Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: polypeptide ligand

<400> SEQUENCE: 8

Leu Glu Thr Thr Cys Ala Ser Leu Cys Tyr Pro Ser
1               5                   10

<210> SEQ ID NO 9
<211> LENGTH: 12
<212> TYPE: PRT
<213> ORGANISM: Artificial Sequence
<220> FEATURE:
<223> OTHER INFORMATION: polypeptide ligand

<400> SEQUENCE: 9

Leu Gly Thr Asp Trp His Ser Val Ser Tyr Thr Leu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: polypeptide ligand

<400> SEQUENCE: 10

Leu Gly Thr Leu Asn Ala Gly Val Pro Gly Phe Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: polypeptide ligand

<400> SEQUENCE: 11

Leu Thr His Ser Lys Asn Pro Val Phe Leu Ser Thr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: polypeptide ligand

<400> SEQUENCE: 12

Leu Val Pro Thr Thr His Arg His Trp Pro Val Thr
```

```
<210> SEQ ID NO 13
<211> LENGTH: 12
<212> TYPE: PRT
<213> ORGANISM: Artificial Sequence
<220> FEATURE:
<223> OTHER INFORMATION: polypeptide ligand

<400> SEQUENCE: 13

Leu Val Ser Asn Ala Arg Gly Phe Asn Asn Leu Ser
1               5                   10

<210> SEQ ID NO 14
<211> LENGTH: 12
<212> TYPE: PRT
<213> ORGANISM: Artificial Sequence
<220> FEATURE:
<223> OTHER INFORMATION: polypeptide ligand

<400> SEQUENCE: 14

Asn Thr Arg Ile Pro Glu Pro Ile Arg Phe Tyr Met
1               5                   10

<210> SEQ ID NO 15
<211> LENGTH: 12
<212> TYPE: PRT
<213> ORGANISM: Artificial Sequence
<220> FEATURE:
<223> OTHER INFORMATION: polypeptide ligand

<400> SEQUENCE: 15

Asn Val Tyr Thr Phe His Ser Met Ser Pro Met Pro
1               5                   10

<210> SEQ ID NO 16
<211> LENGTH: 12
<212> TYPE: PRT
<213> ORGANISM: Artificial Sequence
<220> FEATURE:
<223> OTHER INFORMATION: polypeptide ligand

<400> SEQUENCE: 16

Gln His Thr Thr Leu Thr Ser His Pro Arg Gln Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: polypeptide ligand

<400> SEQUENCE: 17

Ser Asp Phe Ser Asp Thr Met Pro His Arg Pro Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: polypeptide ligand

<400> SEQUENCE: 18

Ser Ile Asp Thr Ile Gln Ile Leu Ser Leu Arg Ser
1               5                   10
```

<210> SEQ ID NO 19
<211> LENGTH: 12
<212> TYPE: PRT
<213> ORGANISM: Artificial Sequence
<220> FEATURE:
<223> OTHER INFORMATION: polypeptide ligand

<400> SEQUENCE: 19

Ser Ile Ser Trp Ala Ser Gln Pro Pro Tyr Ser Leu
1               5                   10

<210> SEQ ID NO 20
<211> LENGTH: 12
<212> TYPE: PRT
<213> ORGANISM: Artificial Sequence
<220> FEATURE:
<223> OTHER INFORMATION: polypeptide ligand

<400> SEQUENCE: 20

Ser Met Val Lys Phe Pro Arg Pro Leu Asp Ser Arg
1               5                   10

<210> SEQ ID NO 21
<211> LENGTH: 11
<212> TYPE: PRT
<213> ORGANISM: Artificial Sequence
<220> FEATURE:
<223> OTHER INFORMATION: polypeptide ligand

<400> SEQUENCE: 21

Leu Arg Arg Trp Val Arg Val Trp Leu Arg Leu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: polypeptide ligand

<400> SEQUENCE: 22

Thr Met Ser Pro Asn Val Tyr Tyr Thr Ala Phe Gly
1               5                   10

<210> SEQ ID NO 23
<211> LENGTH: 12
<212> TYPE: PRT
<213> ORGANISM: Artificial Sequence
<220> FEATURE:
<223> OTHER INFORMATION: polypeptide ligand

<400> SEQUENCE: 23

Thr Gln Ile Pro Ser Arg Pro Gln Thr Pro Ser Gln
1               5                   10

<210> SEQ ID NO 24
<211> LENGTH: 12
<212> TYPE: PRT
<213> ORGANISM: Artificial Sequence
<220> FEATURE:
<223> OTHER INFORMATION: polypeptide ligand

<400> SEQUENCE: 24

Val Cys Ser Asn Met Tyr Phe Ser Cys Arg Leu Ser
1               5                   10

```
<210> SEQ ID NO 25
<211> LENGTH: 12
<212> TYPE: PRT
<213> ORGANISM: Artificial Sequence
<220> FEATURE:
<223> OTHER INFORMATION: polypeptide ligand

<400> SEQUENCE: 25

Val Pro Pro His Pro Met Thr Tyr Ser Cys Gln Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: polypeptide ligand

<400> SEQUENCE: 26

Val Pro Arg Leu Glu Ala Thr Met Val Pro Asp Ile
1               5                   10

<210> SEQ ID NO 27
<211> LENGTH: 12
<212> TYPE: PRT
<213> ORGANISM: Artificial Sequence
<220> FEATURE:
<223> OTHER INFORMATION: polypeptide ligand

<400> SEQUENCE: 27

Val Pro Thr Lys Pro Glu Leu Pro Val Asn Phe Thr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: polypeptide ligand

<400> SEQUENCE: 28

Trp Ser Ser Asp Leu Pro Gln Pro Ala Ser Thr Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: polypeptide ligand

<400> SEQUENCE: 29

Tyr Ile Thr Pro Tyr Ala His Leu Arg Gly Gly Asn
1               5                   10

<210> SEQ ID NO 30
<211> LENGTH: 12
<212> TYPE: PRT
<213> ORGANISM: Artificial Sequence
<220> FEATURE:
<223> OTHER INFORMATION: polypeptide ligand

<400> SEQUENCE: 30

Asn Val Tyr Thr Asp Asn Thr Leu Ser Pro Thr Pro
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: polypeptide ligand

<400> SEQUENCE: 31

Leu Glu Thr Thr Ala Ala Ser Leu Cys Tyr Pro Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: polypeptide ligand

<400> SEQUENCE: 32

Leu Glu Thr Thr Cys Ala Ser Leu Ala Tyr Pro Ser
1               5                   10

<210> SEQ ID NO 33
<211> LENGTH: 12
<212> TYPE: PRT
<213> ORGANISM: Artificial Sequence
<220> FEATURE:
<223> OTHER INFORMATION: polypeptide ligand

<400> SEQUENCE: 33

Leu Glu Thr Thr Ala Ala Ser Leu Ala Tyr Pro Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: polypeptide ligand

<400> SEQUENCE: 34

Leu Glu Thr Thr Ser Ala Ser Leu Ser Tyr Pro Ser
1               5                   10

<210> SEQ ID NO 35
<211> LENGTH: 12
<212> TYPE: PRT
<213> ORGANISM: Artificial Sequence
<220> FEATURE:
<223> OTHER INFORMATION: D form retroinversion peptide

<400> SEQUENCE: 35

Ser Pro Tyr Cys Leu Ser Ala Cys Thr Thr Glu Leu
1               5                   10

<210> SEQ ID NO 36
<211> LENGTH: 12
<212> TYPE: PRT
<213> ORGANISM: Artificial Sequence
<220> FEATURE:
<223> OTHER INFORMATION: D form peptide

<400> SEQUENCE: 36

Leu Glu Thr Thr Cys Ala Ser Leu Cys Tyr Pro Ser
1               5                   10

<210> SEQ ID NO 37

```
<211> LENGTH: 12
<212> TYPE: PRT
<213> ORGANISM: Artificial Sequence
<220> FEATURE:
<223> OTHER INFORMATION: D form peptide

<400> SEQUENCE: 37

Val Pro Pro His Pro Met Thr Tyr Ser Cys Gln Tyr
1               5                   10

<210> SEQ ID NO 38
<211> LENGTH: 12
<212> TYPE: PRT
<213> ORGANISM: Artificial Sequence
<220> FEATURE:
<223> OTHER INFORMATION: polypeptide ligand

<400> SEQUENCE: 38

Val Pro Pro His Pro Met Thr Tyr Ser Ala Gln Tyr
1               5                   10

<210> SEQ ID NO 39
<211> LENGTH: 12
<212> TYPE: PRT
<213> ORGANISM: Artificial Sequence
<220> FEATURE:
<223> OTHER INFORMATION: polypeptide ligand

<400> SEQUENCE: 39

Val Pro Pro His Pro Met Thr Tyr Ser Ser Gln Tyr
1               5                   10

<210> SEQ ID NO 40
<211> LENGTH: 12
<212> TYPE: PRT
<213> ORGANISM: Artificial Sequence
<220> FEATURE:
<223> OTHER INFORMATION: D form retroinversion peptide

<400> SEQUENCE: 40

Tyr Gln Cys Ser Tyr Thr Met Pro His Pro Pro Val
1               5                   10

<210> SEQ ID NO 41
<211> LENGTH: 12
<212> TYPE: PRT
<213> ORGANISM: Artificial Sequence
<220> FEATURE:
<223> OTHER INFORMATION: D form peptide

<400> SEQUENCE: 41

Val Cys Ser Asn Met Tyr Phe Ser Cys Arg Leu Ser
1               5                   10

<210> SEQ ID NO 42
<211> LENGTH: 12
<212> TYPE: PRT
<213> ORGANISM: Artificial Sequence
<220> FEATURE:
<223> OTHER INFORMATION: polypeptide ligand

<400> SEQUENCE: 42

Val Ser Ser Asn Met Tyr Phe Ser Ser Arg Leu Ser
1               5                   10

<210> SEQ ID NO 43
<211> LENGTH: 19
```

```
<212> TYPE: PRT
<213> ORGANISM: Artificial Sequence
<220> FEATURE:
<223> OTHER INFORMATION: polypeptide ligand

<400> SEQUENCE: 43

Asp Tyr Asp Ser Leu Ser Trp Arg Ser Thr Leu His Gly Gly His Glu
1               5                   10                  15

Ser Ser His

<210> SEQ ID NO 44
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 44
atactgccta ggatgagaag tcaacgtagt atgctg                              36

<210> SEQ ID NO 45
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 45
attagtctaa gccacactcg cacccaacgt cggaga                              36

<210> SEQ ID NO 46
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 46
cctcgaatca agcggacgag gaaacttcac cataga                              36

<210> SEQ ID NO 47
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 47
aggattccgc cacctcatat ccgtagtcgg ctcacc                              36

<210> SEQ ID NO 48
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 48
aagcggcata atattccgct tatgaatcga accatc                              36

<210> SEQ ID NO 49
<211> LENGTH: 36
<212> TYPE: DNA
<213> ORGANISM: Artificial Sequence
<220> FEATURE:
<223> OTHER INFORMATION: encodes polypeptide ligand
```

```
<400> SEQUENCE: 49
atgaagagta gaacgccaag aaagcgaatc ataatc                                36

<210> SEQ ID NO 50
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 50
atacgtcgaa gccggctgcg gcagatcaga cgacca                                36

<210> SEQ ID NO 51
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 51
agtagaaaga aacacaggat tcttagaatg cgtaag                                36

<210> SEQ ID NO 52
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 52
agacagacga caagaaaaat acatattcga acaaac                                36

<210> SEQ ID NO 53
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 53
ctgagaagga gtctgcggcc tagacggaat ctgagt                                36

<210> SEQ ID NO 54
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 54
attcccccca cgcaaatgag cataaggagt aatata                                36

<210> SEQ ID NO 55
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 55
catataaaac ctaatcggct caggaatcct cgtatt                                36

<210> SEQ ID NO 56
```

```
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 56
agaacgaagc gaaagaatct aaatcgtatc aatact                      36

<210> SEQ ID NO 57
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 57
agcaagccaa cgatactcat gcgtatacgc cggctt                      36

<210> SEQ ID NO 58
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 58
cggcatagga gacatagaat gaaacgtata cacatt                      36

<210> SEQ ID NO 59
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 59
cgtaaaatta accggaagct ccggcttagt cggcac                      36

<210> SEQ ID NO 60
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 60
aggaagaacc gtaacaggat tccaaggcca cagacc                      36

<210> SEQ ID NO 61
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 61
ccaataagga ggaggcgtag gatcattcag catatg                      36

<210> SEQ ID NO 62
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 62
```
cgacggataa cacaaactag cacaagtcgt ctcaag          36

<210> SEQ ID NO 63
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 63
cgacagatta ttaaacccac gagcattaga aacaag          36

<210> SEQ ID NO 64
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 64
cgaaggccga tgaggcatag tatccgaaaa atcaga          36

<210> SEQ ID NO 65
<211> LENGTH: 37
<212> TYPE: DNA
<213> ORGANISM: Artificial Sequence
<220> FEATURE:
<223> OTHER INFORMATION: encodes polypeptide ligand

<400> SEQUENCE: 65
catatcagca agaatacgtc ataggatgag gaggcac         37

<210> SEQ ID NO 66
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 66
cggcgtagga gacagagtat tatccgtata cacatt          36

<210> SEQ ID NO 67
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 67
aggcgcagtc cgcagaagcc aaggcggagg agtagc          36

<210> SEQ ID NO 68
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 68
accaaaagcc gtataataca cattcggaga catagt          36

<210> SEQ ID NO 69
<211> LENGTH: 36
<212> TYPE: DNA

-continued

<213> ORGANISM: Artificial Sequence
<220> FEATURE:
<223> OTHER INFORMATION: encodes polypeptide ligand

<400> SEQUENCE: 69
aagagtatac gacacagaat gccaatccgt ccccaa       36

<210> SEQ ID NO 70
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 70
aatatccgga accatcgtcg cctcaagacg aggcac       36

<210> SEQ ID NO 71
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 71
cggaaaaccc ggcacaccag cattcaacgt cccaag       36

<210> SEQ ID NO 72
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 72
cgtcacaggc caatgacgat gagtcgtcgg cacaag       36

<210> SEQ ID NO 73
<211> LENGTH: 36
<212> TYPE: DNA
<213> ORGANISM: Artificial Sequence
<220> FEATURE:
<223> OTHER INFORMATION: encodes polypeptide ligand

<400> SEQUENCE: 73
caaagaataa ggaggctgcg acgcccaaga aataga       36

<210> SEQ ID NO 74
<211> LENGTH: 9
<212> TYPE: PRT
<213> ORGANISM: Artificial Sequence
<220> FEATURE:
<223> OTHER INFORMATION: Segment of mouse keratinocyte growth factor
      receptor

<400> SEQUENCE: 74

Gly Asn Pro Thr Ser Thr Met Arg Trp
1               5

<210> SEQ ID NO 75
<211> LENGTH: 8
<212> TYPE: PRT
<213> ORGANISM: Artificial Sequence
<220> FEATURE:
<223> OTHER INFORMATION: Segment of human urokinase-type plasminogen
      activator precursor (u-PA)

-continued

```
<400> SEQUENCE: 75

Pro Trp Asn Ser Ala Thr Val Leu
1               5

<210> SEQ ID NO 76
<211> LENGTH: 8
<212> TYPE: PRT
<213> ORGANISM: Artificial Sequence
<220> FEATURE:
<223> OTHER INFORMATION: Segment of xenla epithelial-cadherin precursor
      (e-cadherin)

<400> SEQUENCE: 76

Asn Asp Pro Thr Ala Pro Pro Tyr
1               5

<210> SEQ ID NO 77
<211> LENGTH: 8
<212> TYPE: PRT
<213> ORGANISM: Artificial Sequence
<220> FEATURE:
<223> OTHER INFORMATION: Segment of precursor (FCeRI) (IGE FC receptor,
      alpha-subunit) (FC-epsilon RIalpha)

<400> SEQUENCE: 77

Tyr Thr Ile Glu Tyr Arg Trp Leu
1               5

<210> SEQ ID NO 78
<211> LENGTH: 11
<212> TYPE: PRT
<213> ORGANISM: Artificial Sequence
<220> FEATURE:
<223> OTHER INFORMATION: Segment of CLALU lectin-related protein
      precursor (CLLRP) (LRPCL) CAVPO casein a precursor

<400> SEQUENCE: 78

Glu Thr Leu Ile Ala Ser Leu Thr Tyr Pro Ser
1               5                   10

<210> SEQ ID NO 79
<211> LENGTH: 8
<212> TYPE: PRT
<213> ORGANISM: Artificial Sequence
<220> FEATURE:
<223> OTHER INFORMATION: Segment of CAVPO casein A precursor

<400> SEQUENCE: 79

Glu Thr Ile Cys Ala Ser Leu Cys
1               5

<210> SEQ ID NO 80
<211> LENGTH: 11
<212> TYPE: PRT
<213> ORGANISM: Artificial Sequence
<220> FEATURE:
<223> OTHER INFORMATION: Segment of pig zonadhesin precursor

<400> SEQUENCE: 80

Leu Gly Thr Asp Trp Phe Ser Pro Asn Cys Thr
1               5                   10

<210> SEQ ID NO 81
<211> LENGTH: 8
<212> TYPE: PRT
<213> ORGANISM: Artificial Sequence
<220> FEATURE:
```

```
<223> OTHER INFORMATION: Segment of mouse elastin precursor
      (tropoelastin)

<400> SEQUENCE: 81

Leu Gly Ala Gly Val Pro Gly Phe
1               5

<210> SEQ ID NO 82
<211> LENGTH: 6
<212> TYPE: PRT
<213> ORGANISM: Artificial Sequence
<220> FEATURE:
<223> OTHER INFORMATION: Segment of mouse elastin precursor
      (tropoelastin)

<400> SEQUENCE: 82

Ala Gly Val Pro Gly Phe
1               5

<210> SEQ ID NO 83
<211> LENGTH: 6
<212> TYPE: PRT
<213> ORGANISM: Artificial Sequence
<220> FEATURE:
<223> OTHER INFORMATION: Segment of mouse elastin precursor
      (tropoelastin)

<400> SEQUENCE: 83

Ala Gly Val Pro Gly Phe
1               5

<210> SEQ ID NO 84
<211> LENGTH: 6
<212> TYPE: PRT
<213> ORGANISM: Artificial Sequence
<220> FEATURE:
<223> OTHER INFORMATION: Segment of mouse elastin precursor
      (tropoelastin)

<400> SEQUENCE: 84

Ala Gly Val Pro Gly Phe
1               5

<210> SEQ ID NO 85
<211> LENGTH: 6
<212> TYPE: PRT
<213> ORGANISM: Artificial Sequence
<220> FEATURE:
<223> OTHER INFORMATION: Segment of mouse elastin precursor
      (tropoelastin)

<400> SEQUENCE: 85

Ala Gly Val Pro Gly Phe
1               5

<210> SEQ ID NO 86
<211> LENGTH: 9
<212> TYPE: PRT
<213> ORGANISM: Artificial Sequence
<220> FEATURE:
<223> OTHER INFORMATION: Segment of mouse stromelysin-3 precursor
      (matrix metalloproteinase-11) (MMP-11)

<400> SEQUENCE: 86

Pro Glu Ser His Arg His His Pro Val
1               5
```

```
<210> SEQ ID NO 87
<211> LENGTH: 12
<212> TYPE: PRT
<213> ORGANISM: Artificial Sequence
<220> FEATURE:
<223> OTHER INFORMATION: Segment of rat sucrase-isomaltase, intestinal

<400> SEQUENCE: 87

Asn Pro Tyr Thr Leu Thr Ser Ile Gln Pro Leu Pro
1               5                   10

<210> SEQ ID NO 88
<211> LENGTH: 8
<212> TYPE: PRT
<213> ORGANISM: Artificial Sequence
<220> FEATURE:
<223> OTHER INFORMATION: Segment of human placental-cadherin precursor
      (P-Cadherin)

<400> SEQUENCE: 88

His Phe Thr Ile Thr Thr His Pro
1               5

<210> SEQ ID NO 89
<211> LENGTH: 10
<212> TYPE: PRT
<213> ORGANISM: Artificial Sequence
<220> FEATURE:
<223> OTHER INFORMATION: Segment of CAPHI beta casein precursor

<400> SEQUENCE: 89

Ser Trp Met His Gln Pro Pro Gln Pro Leu
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Segment of ZO1 mouse tight junction protein
      ZO1 (tight junction protein 1)

<400> SEQUENCE: 90

Pro Arg Asp Leu Asp Ser Arg
1               5

<210> SEQ ID NO 91
<211> LENGTH: 11
<212> TYPE: PRT
<213> ORGANISM: Artificial Sequence
<220> FEATURE:
<223> OTHER INFORMATION: Segment of mouse versican core precursor

<400> SEQUENCE: 91

Thr Glu Leu Pro Lys Phe Pro Ser Thr Pro Ser
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Segment of mouse versican core precursor

<400> SEQUENCE: 92

Thr Gly Ile Pro Ser Thr Pro Gln Lys Pro Thr
1               5                   10
```

```
<210> SEQ ID NO 93
<211> LENGTH: 10
<212> TYPE: PRT
<213> ORGANISM: Artificial Sequence
<220> FEATURE:
<223> OTHER INFORMATION: Segment of PAPCY Metalloproteinase inhibitor
      1 precursor (TIMP-1)

<400> SEQUENCE: 93

Val Pro Pro His Pro Gln Thr Ala Phe Cys
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Segment of human versican core protein
      precursor

<400> SEQUENCE: 94

Ile Pro Arg Lys Ser Ala Thr Val Ile Pro Glu Ile
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Segment of human collagen alpha 1 (VII) chain
      precursor (long-chain collagen)

<400> SEQUENCE: 95

Val Pro Thr Gly Pro Glu Leu Pro Val Ser
1               5                   10

<210> SEQ ID NO 96
<211> LENGTH: 8
<212> TYPE: PRT
<213> ORGANISM: Artificial Sequence
<220> FEATURE:
<223> OTHER INFORMATION: Segment of rat insulin-like growth factor
      I receptor

<400> SEQUENCE: 96

Pro Tyr Ala His Met Asn Gly Gly
1               5

<210> SEQ ID NO 97
<211> LENGTH: 5
<212> TYPE: PRT
<213> ORGANISM: Artificial Sequence
<220> FEATURE:
<223> OTHER INFORMATION: polypeptide ligand

<400> SEQUENCE: 97

His Glu Ser Ser His
1               5

<210> SEQ ID NO 98
<211> LENGTH: 12
<212> TYPE: PRT
<213> ORGANISM: Artificial Sequence
<220> FEATURE:
<223> OTHER INFORMATION: polypeptide ligand
<220> FEATURE:
<221> NAME/KEY: MISC_FEATURE
<222> LOCATION: (5)..(5)
```

```
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: any amino acid
<220> FEATURE:
<221> NAME/KEY: MISC_FEATURE
<222> LOCATION: (11)..(11)
<223> OTHER INFORMATION: any amino acid

<400> SEQUENCE: 98

Asn Val Tyr Thr Xaa Xaa Xaa Xaa Ser Pro Xaa Pro
1               5                   10

<210> SEQ ID NO 99
<211> LENGTH: 4
<212> TYPE: PRT
<213> ORGANISM: Artificial Sequence
<220> FEATURE:
<223> OTHER INFORMATION: polypeptide ligand

<400> SEQUENCE: 99

Thr Pro Pro Pro
1

<210> SEQ ID NO 100
<211> LENGTH: 12
<212> TYPE: PRT
<213> ORGANISM: Artificial Sequence
<220> FEATURE:
<223> OTHER INFORMATION: sequence 9/12 homologous to SEQ ID NO:1

<400> SEQUENCE: 100

Leu Thr Pro Pro Pro Trp Leu Val Arg Thr Arg Pro
1               5                   10
```

PEYER'S PATCH AND/OR M-CELL TARGETING LIGANDS

CROSS REFERENCE TO RELATED APPLICATIONS

This application claims the benefit of U.S. provisional application No. 60/302,591 filed Jul. 2, 2001, which application is incorporated by reference herein in its entirety.

FIELD OF INVENTION

This invention relates to novel targeting ligands which permit or facilitate the transport of drugs, macromolecules, or particles, such as biodegradable nanoparticles and microparticles, or bacterial carriers or viral carriers through the intestinal epithelium, M-cells located in gut associated lymphoid tissue, and/or Peyer's Patch tissue of the intestinal epithelium.

BACKGROUND OF THE INVENTION

The epithelial cells lining the lumenal side of the gastrointestinal tract (GTT) are a major barrier to drug delivery following oral administration. However, there are four recognized transport pathways which can be exploited to facilitate drug delivery and transport: the transcellular, paracellular, carrier-mediated and transcytotic transport pathways. The ability of a conventional drug, peptide, protein, macromolecule, nanoparticulate system or microparticulate system to interact with one of these transport pathways may result in increased delivery of that drug or particle from the GIT to the underlying circulation.

M-cells are antigen sampling cells that are found in the epithelium of the gut-associated lymphoid tissue, or Peyer's Patch. The transcytotic capacity of M-cells and the downstream processing of the antigen sampled would suggest that targeting vaccines to M-cells would enhance oral immunization (Foster et al., 15 Vaccine 546-71 (1998)). However, to date, no human M-cell marker has been identified as a target for delivery of vaccines and/or other drugs through the M-cell route.

In U.S. Pat. No. 6,117,632 to O'Mahony, one of the present inventors disclosed a method of identifying peptides which permit or facilitate the transport of an active agent through human or animal epithelial tissue. This method uses in vivo phage display screening to identify ligands.

U.S. Pat. No. 6,060,082 to Chen et al. discloses modified polymerized liposomes that contain a molecule or ligand on their surfaces in order to target the liposomes to a specific site or cell type for oral/mucosal drug delivery. Also disclosed is an embodiment in which the liposomes are modified with carbohydrate moities or lectins that specifically target M-cells or Peyer's Patches in mice. However, this reference only teaches transport of liposomes.

Other approaches include: drug delivery through the epithelium by a carrier molecule selected from transferrin receptor ligands conjugated to an active agent and a transport enhancing agent (U.S. Pat. No. 5,254,342 to Shen et al.); and coupling the antigen to ligands that bind the FcRn receptor. (U.S. Pat. No. 6,030,613 to Blumberg et al.).

All references cited herein are incorporated herein by reference in their entireties.

Thus, there still exists a need for M-cell and/or Peyer's Patch specific ligands that are particularly effective in transporting drugs, including drug-loaded nanoparticles and microparticles, or bacterial or viral carries coding for vaccines into or across a human or animal intestinal epithelium.

BRIEF SUMMARY OF THE INVENTION

In an aspect directly related to specific 12-mer L-peptides, the invention is a purified synthetic polypeptide ligand comprising a 12-mer L-peptide, fragment or homologue thereof, said 12-mer L-peptide selected from the group consisting of SEQ ID NOs:1–34, SEQ ID NOs:38–39, and SEQ ID NO:42 wherein said fragment is at least five contiguous amino acids and wherein said homologue is at least 9/12 homologous to a 12-mer peptide selected from said group and wherein said 12-mer L-peptide, fragment or homologue thereof, when integrated as an N-terminal PIII fusion peptide of an M13 phage confers an ability to bind the phage to either Caco-2 cell, IEC-6 cell, rat, mouse, pig or dog homogenate membrane fractions, said ability being at least as great as that conferred by a similarly integrated 12-mer peptide of SEQ ID NO:67.

The above noted functional test is "wherein said 12-mer L-peptide, fragment or homologue thereof, when integrated as an N-terminal PIII fusion peptide of an M13 phage confers an ability to bind the phage either to Caco-2 cell, IEC-6 cell, rat, mouse, pig or dog homogenate membrane fractions, said ability being at least as great as that conferred by a similarly integrated 12-mer peptide of SEQ ID NO:67", and is also specified below for other aspects and embodiments of the invention. For all agents and embodiments, preferred ligands are those that satisfy the functional test when Caco-2 cell homogenate membrane fractions are used.

"9/12 homologous to a 12-mer peptide" means that if one aligns a homologue with the 12-mer peptide, 9 of 12 amino acids, contiguous or not, are identical to the 12-mer peptide. For example, if a peptide contained the sequence LTPPP-WLVRTRP (SEQ ID NO: 100), it would be 9/12 homologous to the 12-mer peptide of SEQ ID NO:1 (ATPPPWLLRTAP).

It follows that, in the above noted aspect of the invention a peptide can be 9/12 homologous to a specified 12-mer peptide, but not a fragment of at least five contiguous amino acids of that 12-mer peptide. Conversely, a peptide can be a fragment of at least five contiguous amino acids (e.g. 5–8 amino acids), but not at least 9/12 homologous to the 12-mer peptide. However, a peptide can also be both: a fragment of at least five amino acids of the 12-mer peptide and at least 9/12 homologous to the 12-mer peptide. A peptide that is 9/12 homologous to a 12-mer peptide is 75% homologous to that peptide.

In an aspect related to the D-forms of the specific 12-mer L-peptides, the invention is a purified synthetic polypeptide ligand comprising a 12-mer D-peptide, fragment or homologue thereof, said 12-mer D-peptide being the D-form of a 12-mer L-peptide selected from the group consisting of D-forms of 12-mer L-peptides of SEQ ID NOs:1–34, SEQ ID NOs:38–39 and SEQ ID NO:42, wherein said fragment is at least five contiguous amino acids and wherein said homologue is at least 9/12 homologous to a 12-mer D-peptide selected from said group and wherein said 12-mer D-peptide, fragment or homologue, when integrated as an N-terminal PIII fusion peptide of an M13 phage confers an ability to bind the phage to either Caco-2 cell, IEC-6 cell, rat, mouse, pig or dog homogenate membrane fractions, said ability being at least as great as that conferred by a similarly integrated 12-mer peptide of SEQ ID NO:67.

In an aspect related to the retro-inverted forms of the specific 12-mer L-peptides, the invention is a purified synthetic polypeptide ligand comprising a 12-mer retro-inverted peptide, fragment or homologue thereof, said 12-mer retro-inverted peptide being the retro-inverted form of a 12-mer L-peptide selected from the group consisting of retro-inverted forms of 12-mer L-peptides of SEQ ID NOs:1–34, SEQ ID NOs:38–39 and SEQ ID NO:42, wherein said fragment is at least five contiguous amino acids and wherein said homologue is at least 9/12 homologous to a 12-mer retro-inverted peptide selected from said group and wherein said 12-mer retro-inverted peptide, fragment or homologue, when integrated as an N-terminal PIII fusion peptide of an M13 phage confers an ability to bind the phage to either Caco-2 cell, IEC-6 cell, rat, mouse, pig or dog homogenate membrane fractions, said ability being at least as great as that conferred by a similarly integrated 12-mer peptide of SEQ ID NO:67.

In an aspect related to specific protein motifs, the invention is a purified synthetic polypeptide ligand, said ligand comprising a L-peptide motif, D-peptide version thereof, or retro-inverted version thereof, said L-peptide motif being selected from the group consisting of TPPP (SEO ID NO:99), PPY, PVT, LGT, NVY, HESSH (SEQ ID NO:97) and NVYTXXXXSPXP (SEQ ID NO:98), wherein said L-peptide motif, a D-peptide version thereof, or a retro-inverted version thereof when integrated as an N-terminal PIII fusion peptide of an M13 page confers an ability to bind the phage to either Caco-2 cell, IEC-6 cell, rat, mouse, pig or dog homogenate membrane fractions, said ability being at least as great as that conferred by a similarly integrated 12-mer peptide of SEQ ID NO:67.

In an aspect related to naturally occurring homologues of the specific L-peptides, the invention is a purified synthetic polypeptide ligand, not more than 200 amino acids in length, comprising an L-peptide, fragment or homologue thereof, said L-peptide being 6 to 12 amino acids in length, and said L-peptide being selected from the group consisting of SEQ ID NOs:74 through SEQ ID NO:96, wherein said fragment is at least five contiguous amino acids and wherein said homologue is at least 83% homologous to an L-peptide selected from said group wherein said L-peptide, fragment or homologue thereof when integrated as an N-terminal PIII fusion peptide of an M13 phage confers an ability to bind the phage to either Caco-2 cell, IEC-6 cell, rat, mouse, pig or dog homogenate membrane fractions, said ability being at least as great as that conferred by a similarly integrated 12-mer peptide of SEQ ID NO:67.

In an aspect related to the D-forms of naturally occurring homologues of the specific L-peptides, the invention is a purified synthetic polypeptide ligand, not more than 200 amino acids in length, comprising a D-peptide, fragment or homologue thereof, said D-peptide being 6 to 12 amino acids in length and said D-peptide being the D-form of a L-peptide selected from the group consisting of SEQ ID NOs:74 through SEQ ID NO:96, wherein said fragment is at least five contiguous amino acids and wherein said homologue is at least 83% homologous to a D-peptide selected from said group and wherein said D-peptide, fragment or homologue thereof when integrated as an N-terminal PIII fusion peptide of an M13 phage confers an ability to bind the phage to either Caco-2 cell, IEC-6 cell, rat, mouse, pig or dog homogenate membrane fractions, said ability being at least as great as that conferred by a similarly integrated 12-mer peptide of SEQ ID NO:67.

In an aspect related to the retro-inverted forms of the naturally occurring homologues of the specific L-peptides, the invention is a purified synthetic polypeptide ligand, not more than 200 amino acids in length, comprising a retro-inverted peptide, fragment or homologue thereof, said retro-inverted peptide being 6 to 12 amino acids in length and said retro-inverted peptide being the retro-inverted form of a L-peptide selected from the group consisting of SEQ ID NOs:74 through SEQ ID NO:96, wherein said fragment is at least five contiguous amino acids and wherein said homologue is at least 83% homologous to a retro-inverted peptide wherein said retro-inverted peptide, fragment or homologue thereof when integrated as an N-terminal PIII fusion peptide of an M13 phage confers an ability to bind the phage to either Caco-2 cell, IEC-6 cell, rat, mouse, pig or dog homogenate membrane fractions, said ability being at least as great as that conferred by a similarly integrated 12-mer peptide of SEQ ID NO:67.

In the above inventions, related to purified synthetic polypeptide ligands there are preferred and even highly preferred embodiments.

As regards the inventions related to the specific 12-mer L-peptides or the naturally occurring 12-mer homologues, their D-forms and their retro-inverted forms, it is preferred that the homologue is at least 10/12 homologous, more preferably 11/12 homologous. Similarly it is preferred that fragments of a 12-mer be at least 8 amino acids in length. Most preferred is the presence of the intact specific L-peptide, D-form, or retro-inverted form, rather than a homologue or fragment.

As to all of the aforementioned purified synthetic polypeptide ligands, it is preferred that their length be not more than 200 amino acids, more preferably not more than 100 amino acids, most preferably not more than 50 amino acids. Conversely, it is preferred that their length be at least 12 amino acids, more preferably at least 20 amino acids, most preferably at least 30 amino acids.

In particular embodiments of all of the aforementioned purified synthetic polypeptide ligands, the polypeptide comprises a zinc-binding domain.

Nucleic acid molecules that code for the aforementioned purified synthetic polypeptide ligands are also aspects of the invention. Preferred are those that are not more than 600 nucleotides in length. Highly preferred are those that code for a purified synthetic polypeptide that comprises one of the specific 12-mer peptides, motifs, or naturally occurring homologues.

In particular embodiments of the invention, one of the aforementioned purified synthetic polypeptides ligands is integrated into the protein of a phage.

In particular embodiments of the invention, one of the aforementioned purified synthetic polypeptide ligands is covalently or non-covalently bound to a carrier entity comprising a pharmaceutical agent. For example, the carrier entity is selected from the group consisting of a nanoparticle, microparticle, liposome, bacterium, phage (bacteriophage) and virus (preferably a mammalian virus, most preferably a human virus; especially non-pathogenic forms made by recombinant or other technologies). It is preferred that the nanoparticle, microparticle or liposome have a largest dimension that is in the range of 10 nm to 500 μm, as discussed in more detail elsewhere herein. In particular embodiments of the invention, the pharmaceutical agent is a drug or therapeutic agent. In other specific embodiments, the pharmaceutical agent is a pathogen antigen.

Certain aspects of the invention involve the use of the purified synthetic polypeptide ligands to target delivery of pharmaceutical agents.

In one aspect, the invention is a method of administering a pharmaceutical agent to an organism having intestinal epithelium, said method comprising contacting said intestinal epithelium with one of the aforementioned purified synthetic polypeptide ligands that is covalently, or non-covalently bound to, a carrier entity. In preferred the embodiments, the organism is a mammal. Most preferably, the mammal is a human.

In particular embodiments of the method, the carrier entity is selected from the group consisting of a nanoparticle, microparticle, liposome, bacterium, phage and virus. A preferred embodiment is where the polypeptide ligand is expressed on the surface of a phage or bacterium further comprising an antigen or a gene encoding the antigen also expressed on the surface.

Preferably, the microparticle, nanoparticle or liposome has its major dimension in the range of 10 nm to 500 μm. In preferred embodiments, the carrier entity is loaded with a pharmaceutical agent. The preferred route of administration for delivery of the ligand-carrier entity is the oral route. Other possible routes are the rectal, subcutaneous, intramuscular, nasal and intravenous routes. In particular embodiments the purified synthetic polypeptide ligand is a 12-mer integrated into a coat protein of a phage. In other particular embodiments, the purified synthetic polypeptide ligand comprises a zinc-binding motif, and said ligand is contacted with said epithelium in the presence of zinc.

BRIEF DESCRIPTION OF THE DRAWINGS

FIG. 1A is a graph of the binding of the phage from Rat 1 to rat Peyer's patch tissue as a function of absorbance at 405 nm;

FIG. 1B is a graph of the binding of the phage from Rat 1 to rat Peyer's patch tissue as a function of absorbance at 405 nm;

FIG. 2 is a graph of the binding of the phage from Rat 2 to rat Peyer's patch tissue as a function of absorbance at 405 nm;

FIG. 3 is a graph of the binding of the phage from Rat 3 to rat Peyer's patch tissue as a function of absorbance at 405 nm;

FIG. 4 is a graph of the binding of the phage from Rat 4 to rat Peyer's patch tissue as a function of absorbance at 405 nm;

FIG. 5 is a graph of the binding of the phage form Rat 5 to rat Peyer's patch tissue as a function of the absorbance at 405 nm;

FIG. 6 is a graph of the binding of the 55 high binding clones to rat small intestinal homogenates with and without Peyer's patch tissue present as a function of absorbance at 405 nm;

FIG. 7 is a graph of the binding of the remaining 55 high binding clones to rat small intestinal homogenates with and without Peyer's patch tissue present as a function of absorbance at 405 nm;

FIG. 8 is a graph of the binding of the clones to dog small intestinal homogenates with and without Peyer's patch tissue present as a function of absorbance at 405 nm;

FIG. 9 is a graph of the binding of the clones to pig small intestinal homogenates with and without Peyer's patch tissue present as a function of absorbance at 405 nm;

FIG. 10 is a graph of the binding of the clones to mouse small intestinal homogenates with and without Peyer's patch tissue present as a function of absorbance at 405 nm;

FIG. 11 is a graph of the binding of the phage clones to rat Peyer's patch, Caco-2 cells and IEC-6 cells as a function of absorbance at 405 nm;

FIG. 12 is a graph of the binding of the phage clones to differentiated and non-differentiated Caco-2 cells as a function of absorbance at 405 nm;

FIG. 13A is a graph of the binding of SEQ ID NO:3 with a biotin tag at the amino terminal end to Caco-2 homogenates and rat GI homogenates as a function of absorbance at 650 nm. Results were obtained using an ELISA-based assay with streptavidin-peroxidase detection.

FIG. 13B is a graph of the binding of SEQ ID NO:4 with a biotin tag at the amino terminal end to Caco-2 homogenates and rat GI homogenates as a function of absorbance at 650 nm. Results were obtained using an ELISA-based assay with streptavidin-peroxidase detection.

FIG. 13C is a graph of the binding of SEQ ID NO:7 with a biotin tag at the amino terminal end to Caco-2 homogenates and rat GI homogenates as a function of absorbance at 650 nm. Results were obtained using an ELISA-based assay with streptavidin-peroxidase detection.

FIG. 13D is a graph of the binding of SEQ ID NO:8 with a biotin tag at the amino and carboxyl terminal end to Caco-2 homogenates and rat GI homogenates as a function of absorbance at 650 nm. Results were obtained using an ELISA-based assay with streptavidin-peroxidase detection.

FIG. 13E is a graph of the binding of SEQ ID NO:5 with a biotin tag at the amino terminal end to Caco-2 homogenates and rat GI homogenates as a function of absorbance at 650 nm. Results were obtained using an ELISA-based assay with streptavidin-peroxidase detection.

FIG. 13F is a graph of the binding of SEQ ID NO:14 with a biotin tag at the amino and carboxyl terminal end to Caco-2 homogenates and rat GI homogenates as a function of absorbance at 650 nm. Results were obtained using an ELISA-based assay with streptavidin-peroxidase detection.

FIG. 13G is a graph of the binding of SEQ ID NO:9 with a biotin tag at the amino terminal end to Caco-2 homogenates and rat GI homogenates as a function of absorbance at 650 nm Results were obtained using an ELISA-based assay with streptavidin-peroxidase detection.

FIG. 13H is a graph of the binding of SEQ ID NO:20 with a biotin tag at the amino terminal end to Caco-2 homogenates and rat GI homogenates as a function of absorbance at 650 nm. Results were obtained using an ELISA-based assay with streptavidin-peroxidase detection.

FIG. 13I is a graph of the binding of SEQ ID NO:17 with a biotin tag at the amino terminal end to Caco-2 homogenates and rat GI homogenates as a function of absorbance at 650 nm. Results were obtained using an ELISA-based assay with streptavidin-peroxidase detection.

FIG. 13J is a graph of the binding of SEQ ID NO:28 with a biotin tag at the amino terminal end to Caco-2 homogenates and rat GI homogenates as a function of absorbance at 650 nm. Results were obtained using an ELISA-based assay with streptavidin-peroxidase detection.

FIG. 13K is a graph of the binding of SEQ ID NO:26 with a biotin tag at the amino terminal end to Caco-2 homogenates and rat GI homogenates as a function of absorbance at 650 nm. Results were obtained using an ELISA-based assay with streptavidin-peroxidase detection.

FIG. 13L is a graph of the binding of SEQ ID NO:11 with a biotin tag at the amino terminal end to Caco-2 homogenates and rat GI homogenates as a function of absorbance at 650 nm. Results were obtained using an ELISA-based assay with streptavidin-peroxidase detection.

FIG. 13M is a graph of the binding of SEQ ID NO:10 with a biotin tag at the amino terminal end to Caco-2 homogenates as a function of absorbance at 650 nm. Results were obtained using an ELISA-based assay with streptavidin-peroxidase detection.

FIG. 13N is a graph of the binding of SEQ ID NO:16 with a biotin tag at the amino terminal end to Caco-2 homogenates as a function of absorbance at 650 nm. Results were obtained using an ELISA-based assay with streptavidin-peroxidase detection.

FIG. 13O is a graph of the binding of SEQ ID NO:19 with a biotin tag at the amino terminal end to Caco-2 homogenates and rat GI homogenates as a function of absorbance at 650 nm. Results were obtained using an ELISA-based assay with streptavidin-peroxidase detection.

FIG. 13P is a graph of the binding of SEQ ID NO:29 with a biotin tag at the amino terminal end to Caco-2 homogenates and rat GI homogenates as a function of absorbance at 650 nm. Results were obtained using an ELISA-based assay with streptavidin-peroxidase detection.

FIG. 13Q is a graph of the binding of SEQ ID NO:30 with a biotin tag at the amino terminal end to Caco-2 homogenates as a function of absorbance at 650 nm. Results were obtained using an ELISA-based assay with streptavidin-peroxidase detection.

FIG. 13R is a graph of the binding of SEQ ID NO:15 with a biotin tag at the amino terminal end to Caco-2 homogenates as a function of absorbance at 650 nm. Results were obtained using an ELISA-based assay with streptavidin-peroxidase detection.

FIG. 14A is a graph of the binding of SEQ ID NOs: 8 and 14 with a biotin tag at both the amino and carboxyl terminal end to pig GI homogenate as a function of absorbance at 650 nm.

FIG. 14B is a graph of the binding of SEQ ID NOs: 8 and 14 with a biotin tag at both the amino and carboxyl terminal end to pig Peyer's Patch homogenate as a function of absorbance at 650 nm.

FIG. 14C is a graph of the binding of SEQ ID NOs: 8 and 14 with a biotin tag at both the amino and carboxyl terminal end to rat GI homogenate as a function of absorbance at 650 nm.

FIG. 14D is a graph of the binding of SEQ ID NOs: 8 and 14 with a biotin tag at both the amino and carboxyl terminal end to rat Peyer's patch homogenate as a function of absorbance at 650 nm.

FIG. 14E is a graph of the binding of SEQ ID NOs: 8 and 14 with a biotin tag at both the amino and carboxyl terminal end to dog GI homogenate as a function of absorbance at 650 nm.

FIG. 14F is a graph of the binding of SEQ ID NOs: 8 and 14 with a biotin tag at both the amino and carboxyl terminal end to dog Peyer's patch homogenate as a function of absorbance at 650 nm.

FIG. 14G is a graph of the binding of SEQ ID NOs: 8 and 14 with a biotin tag at both the amino and carboxyl terminal end to mouse GI homogenate as a function of absorbance at 650 nm.

FIG. 14H is a graph of the binding of SEQ ID NOs: 8 and 14 with a biotin tag at both the amino and carboxyl terminal end to mouse Peyer's patch homogenate as a function of absorbance at 650 nm.

FIG. 14I is a graph of the binding of SEQ ID NOs: 3, 7 and 9 with a biotin tag at the amino terminal end to dog GI homogenate as a function of absorbance at 650 nm.

FIG. 14J is a graph of the binding of SEQ ID NOs: 3, 7 and 9 with a biotin tag at the amino terminal end to dog Peyer's patch homogenate as a function of absorbance at 650 nm.

FIG. 14K is a graph of the binding of SEQ ID NOs: 3, 7 and 9 with a biotin tag at the amino terminal end to mouse GI homogenate as a function of absorbance at 650 nm.

FIG. 14L is a graph of the binding of SEQ ID NOs: 3, 7 and 9 with a biotin tag at the amino terminal end to mouse Peyer's patch homogenate as a function of absorbance at 650 nm.

FIG. 15A is a graph of the binding of SEQ ID NOs: 8 and 14 with a biotin tag at the amino and carboxyl terminal end to rat liver tissue homogenate as a function of absorbance at 650 nm.

FIG. 15B is a graph of the binding of SEQ ID NOs: 8 and 14 with a biotin tag at the amino and carboxyl terminal end to rat spleen tissue homogenate as a function of absorbance at 650 nm.

FIG. 15C is a graph of the binding of SEQ ID NOs: 8 and 14 with a biotin tag at the amino and carboxyl terminal end to rat lung tissue homogenate as a function of absorbance at 650 nm.

FIG. 15D is a graph of the binding of SEQ ID NOs: 8 and 14 with a biotin tag at the amino and carboxyl terminal end to rat kidney tissue homogenate as a function of absorbance at 650 nm.

FIG. 15E is a graph of the binding of SEQ ID NOs: 8 and 14 with a biotin tag at the amino and carboxyl terminal end to rat mesenteric lymph node tissue homogenate as a function of absorbance at 650 nm.

FIG. 16A is a graph of the binding of SEQ ID NO:8 at a concentration of 25 µg/ml to intestinal epithelial tissue in the presence of varying concentrations of free L-cysteine as a function of absorbance at 650 nm.

FIG. 16B is a graph of the binding of SEQ ID NO:8 at a concentration of 12.5 µg/ml to intestinal epithelial tissue in the presence of varying concentrations of free L-cysteine as a function of absorbance at 650 nm.

FIG. 16C is a graph of the binding of SEQ ID NO:8 at a concentration of 6.25 µg/ml to intestinal epithelial tissue in the presence of varying concentrations of free L-cysteine as a function of absorbance at 650 nm.

FIG. 16D is a graph of the binding of SEQ ID NO:25 at a concentration of 6.25 µg/ml to intestinal epithelial tissue in the presence of varying concentrations of free L-cysteine as a function of absorbance at 650 nm.

FIG. 17A is a graph of the binding of derivatives of SEQ ID NO:8, including SEQ ID NOs: 31, 32 and 33, to Caco-2 homogenates as a function of absorbance at 650 nm.

FIG. 17B is a graph of the binding of derivatives of SEQ ID:25, including SEQ ID NOs: 37, 38 and 40, to Caco-2 homogenates as a function of absorbance at 650 nm.

FIG. 18 is a graph of the binding of SEQ ID NO:3 with a zinc-binding motif, SEQ ID NO:43, to Caco-2 homogenates as a function of absorbance at 650 nm.

FIG. 19A is a graph of the binding of SEQ ID NOs: 25, 31, 32 and 33 that were adsorbed to streptavidin particles to Caco-2 cells as a function of absorbance at 650 nm.

FIG. 19B is a graph of the binding of SEQ ID NOs: 25 and 40 that were adsorbed to streptavidin particles to Caco-2 cells as a function of absorbance at 650 nm.

DETAILED DESCRIPTION OF THE INVENTION

The present invention relates to targeted polypeptide ligands for mucosal delivery of agents through the intestinal epithelium. In one embodiment of the invention, the polypeptide ligands are targeted to M-cells or Peyer's patch tissue of the intestinal epithelium.

As used herein, the term "purified synthetic polypeptide ligand" is intended to distinguish polypeptides of the invention from (1) those that consist of a naturally occurring amino acid sequence; and (2) those that naturally occur but have not been purified.

Examples of polypeptides that naturally occur but which have not been purified are fragments of polypeptides that exist as intermediates during the translational process that elongates fragments into complete polypeptides, and proteolytic breakdown products which occur from time to time.

The polypeptide component of a protein, such as mouse keratinocyte growth factor, identified in the Blast homology search below would be an example of a naturally occurring polypeptide.

A population of synthetic polypeptide ligands in solution, wherein most or all of the polypeptides in solution are a particular synthetic polypeptide ligand, is one example of a purified synthetic polypeptide ligand.

A polypeptide ligand that may naturally occur in a eukaryotic cell is a purified synthetic polypeptide ligand if it occurs (but does not naturally occur) on a phage surface or a bacterial surface, or if it occurs on the surface of a nanoparticle, microparticle or liposome, or bacterial or viral carrier, or if it occurs as a result of genetic recombination technologies in a cell, virus or phage where it does not naturally occur.

As used herein, the terms "polypeptide" and "peptide" do not have an intrinsic difference as to biochemical meaning. As indicated herein, a 12-mer peptide can qualify as a polypeptide. In a purified synthetic polypeptide ligand where one or more amino acids have been derivatized (e.g. glycosylation, acetylation, amidation, biotinylation, dansylation) the term purified synthetic polypeptide ligand is intended to apply to the polypeptide component of the ligand. In the case where dansylation comprises the addition of a dansyl-lysine group the polypeptide absent the lysine of the dansyl-lysine group is the purified synthetic polypeptide ligand.

The test for functionality of a 12-mer, fragment or homologue is exemplified by "wherein said 12-mer L-peptide, fragment or homologue thereof, when integrated as an N-terminal PIII fusion peptide of an M13 phage confers an ability to bind the phage to a Caco-2 cell homogenate membrane fraction, said ability being at least as great as that conferred by a similarly integrated 12-mer peptide of SEQ ID NO:67." A cloning vector useful for accomplishing the binding test is M13KE, which is available from New England Labs Inc., as are the details for integrating the peptide {See Technical Bulletin #8101(Apr. 1, 2000), which is incorporated by reference herein in its entirety}. Peptides larger than 20–30 amino acids, if so integrated have deleterious effect on the infectivity of the M13 virus. If it is desired to test the binding functionality of peptides too large to be tested in the phage binding test, such larger peptides in biotinylated form can be tested in the Caco-2 membrane binding assay described herein, in order to see if that larger peptide retains detectable binding activity.

The terms "a Caco-2 cell homogenate membrane fraction" and simply "Caco-2 cell homogenate" are used interchangeably herein unless otherwise indicated. In vivo phage display library screening was used to determine polypeptide ligands that bind to intestinal Peyer's Patch and non-Peyer's Patch tissue homogenates of several species. DNA from one-hundred phage clones with the highest binding affinities (O.D.>0.75) was sequenced to identify the sequence of the peptide insert. Thirty unique sequences were identified, of which there were several common tripeptide motifs. More than one copy of several clones was isolated and several clones were isolated from different rats (See Table 1 below).

The 12-mer peptides and related peptides, a total of 43 in all (See Tables 1 and 2) were synthesized and used as ligands in binding studies. The related peptides included selected homologues, D-forms and retro-inverted forms of the 12-mers, as well as a zinc-binding chimeric peptide (SEQ ID NO:43).

By employing the foregoing techniques, the inventors have identified several polypeptide ligands, which mediate binding to intestinal epithelium of several species, including rat, dog, mouse, pig and/or human intestinal epithelium tissue. Thus, the invention encompasses the following ligands (Tables 1 & 2):

Table 1: Amino Acid Sequences for Ligands

TABLE 1

Amino Acid Sequences for Ligands

| SEQ ID | Sequence | No. of copies of each clone isolated |
|---|---|---|
| SEQ ID NO:1 | ATPPPWLLRTAP | 1 |
| SEQ ID NO:2 | DGSIHKRNIMPL | 1 |
| SEQ ID NO:3 | DYDSLSWRSTLH | 1 |
| SEQ ID NO:4 | GEPTTDMRWRNP | 1 |
| SEQ ID NO:5 | GLWPWNPVTVLP | 5 |
| SEQ ID NO:6 | HMLNDPTPPPYW | 2 |
| SEQ ID NO:7 | KPAYTHEYRWLA | 3 |
| SEQ ID NO:8 | LETTCASLCYPS | 1 |
| SEQ ID NO:9 | LGTDWHSVSYTL | 1 |
| SEQ ID NO:10 | LGTLNAGVPGFP | 1 |
| SEQ ID NO:11 | LTHSKNPVFLST | 1 |
| SEQ ID NO:12 | LVPTTHRHWPVT | 1 |
| SEQ ID NO:13 | LVSNARGFNNLS | 1 |
| SEQ ID NO:14 | NTRIPEPIRFYM | 1 |
| SEQ ID NO:15 | NVYTFHSMSPMP | 1 |
| SEQ ID NO:16 | QHTTLTSHPRQY | 1 |
| SEQ ID NO:17 | SDFSDTMPHRPS | 2 |
| SEQ ID NO:18 | SIDTIQILSLRS | 3 |
| SEQ ID NO:19 | SISWASQPPYSL | 1 |
| SEQ ID NO:20 | SMVKFPRPLDSR | 2 |
| SEQ ID NO:21 | LRRWVRVWLRL | 1 |
| SEQ ID NO:22 | TMSPNVYYTAFG | 1 |
| SEQ ID NO:23 | TQIPSRPQTPSQ | 1 |
| SEQ ID NO:24 | VCSNMYFSCRLS | 1 |
| SEQ ID NO:25 | VPPHPMTYSCQY | 1 |
| SEQ ID NO:26 | VPRLEATMVPDI | 1 |
| SEQ ID NO:27 | VPTKPELPVNFT | 1 |
| SEQ ID NO:28 | WSSDLPQPASTY | 1 |
| SEQ ID NO:29 | YITPYAHLRGGN | 5 |
| SEQ ID NO:30 | NVYTDNTLSPTP | 1 |

TABLE 2

Stabilized versions (D-form, retro-D form) and homologues of these sequences were also synthesized. (L-form amino acid residues are given as capital letters while D-form amino acids are given as lower case letters.)

| SEQ ID | Sequence |
|---|---|
| SEQ ID NO:31 | LETTAASLCYPS |
| SEQ ID NO:32 | LETTCASLAYPS |
| SEQ ID NO:33 | LETTAASLAYPS |
| SEQ ID NO:34 | LETTSASLSYPS |
| SEQ ID NO:35 | spyclsacttel |
| SEQ ID NO:36 | lettcaslcyps |
| SEQ ID NO:37 | vpphpmtyscqy |
| SEQ ID NO:38 | VPPHPMTYSAQY |
| SEQ ID NO:39 | VPPHPMTYSSQY |
| SEQ ID NO:40 | yqcsytmphppv |
| SEQ ID NO:41 | vcsnmyfscrls |
| SEQ ID NO:42 | VSSNMYFSSRLS |
| SEQ ID NO:43 | DYDSLSWRSTLHGGHESSH |

Analysis of the 12-mer peptide sequences revealed that several peptides contain common motifs. Thus, the invention also encompasses these motifs and polypeptide ligands containing the motifs, wherein the polypeptide ligands facilitate transport of a pharmaceutical agent into or across the intestinal epithelium, M-cells or Peyer's patch tissue.

The motifs PPY, PVT, LGT and NVY have no previously defined receptor. The motif TPPP has been described as a low affinity omega-opioid peptide antagonist. Certain opioid receptors have been observed on intestinal epithelium. An additional motif of the invention is NVYTXXXXSPXP (SEQ ID NO:98) wherein X is any amino acid.

There are several groups of preferred synthetic polypeptide ligands of the invention, wherein the members of each group contain related amino acid sequences. A first such group contains ligands comprising an amino acid sequence selected from the group consisting of: LETTCASLCYPS (SEQ ID NO:8), LETTAASLCYPS (SEQ ID NO:31), LETTCASLAYPS (SEQ ID NO:32), LETTAASLAYPS (SEQ ID NO:33), LETTSASLSYPS (SEQ ID NO:34), spyclsacttel (SEQ ID NO:35) and lettsaslsyps (SEQ ID NO:36). A second such group contains ligands selected from the group consisting of: VPPHPMTYSCQY (SEQ ID NO:25), yqcsytmphppv (SEQ ID NO:40), VPPHPMTYSSQY (SEQ ID NO:39) and VPPHPMTYSAQY (SEQ ID NO:38). A third such group contains ligands comprising an amino acid sequence selected from the group consisting of: VCSNMYFSCRLS (SEQ ID NO:24), vcsnmyfscrls (SEQ ID NO:41) and VSSNMYFSSRLS (SEQ ID NO:42).

Ligands of the invention are useful for transporting a carrier entity or pharmaceutical agent into or across the intestinal epithelium, M-cells or Peyer's patch tissue. Thus, the invention not only provides novel ligands, but also provides a method to transport a carrier entity or pharmaceutical agent into or across the intestinal epithelium, or M-cells or Peyer's patch tissue, as well as novel ligand-entity complexes.

As used herein, the term "carrier entity" is defined as a particle, droplet, bacterium, phage or virus that can carry a pharmaceutical agent. As used herein, the term "carrier entity" is also defined as a bacterium, phage or virus that can code for a pharmaceutical agent A microparticle is defined as a particle whose "major dimension" is in the range 1 to 5 μm, most preferably in the range 1 to 3 μm. A nanoparticle is defined as a particle whose major dimension is less than 1 μ, preferably in the range 1 nm to 500 nm, most preferably in the range 10 nm to 500 nm.

As used herein, the major dimension of a spherical particle is its diameter, and that of a rod-shaped particle, its length. For other particles, it is the longest dimension possible for the particle.

Nano- and microparticles that are loaded with, or encapsulate, pharmaceutical agents, can be coated with the polypeptide ligands, such as those of the present invention, that target intestinal epithelium tissue, such as M-cell or Peyer's patch tissue. The coating can be effected by covalent or non-covalent bonding. The covalent bonding can be achieved by adsorption or any other coating process. In either case, the bonding can be made to completed particles or to particle components that subsequently form part of the particles.

Biodegradable particles are preferred.

Pharmaceutical agents can, in the alternative, be directly linked to polypeptide ligands. If the agent is itself a polypeptide or peptide, the product is a chimeric polypeptide comprising both an agent and a targeting portion. Bacterial vectors can express a targeting ligand on their surface and also express an antigen on their surface or carry a gene coding for the antigen. Viral vectors can express a targeting ligand on their surface and also express an antigen on their surface or carry a gene coding for the antigen.

A "pharmaceutical agent" is a therapeutic or diagnostic agent. Therapeutic agents are those that are administered either to treat an existing disease or prophylactically to protect against a potential future disease. Diagnostic agents are any agents that are administered as part of a diagnostic procedure.

Examples of therapeutic agents are drugs, genes, gene-delivery vectors, DNA vaccines, antigens and recombinant viruses.

Drugs include, for example, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins and antidiuretic agents, antisense oligonucleotides, gene-correcting hybrid oligonucleotides, ribozymes, RNA interference (RNA$_i$) oligonucleotides, silencing RNA (siRNA) oligonucleotides, aptameric oligonucleotides and triple-helix forming oligonucleotides.

Examples of gene-delivery vectors are DNA molecules, viral vectors (E.g. adenovirus, adeno-associated virus, retroviruses, herpes simplex virus, and sindbus virus), and cationic lipid-coated DNA and DNA-dendrimers.

Examples of drugs are as insulin, calcitonin, calcitonin gene regulating protein, atrial natriuretic protein, colony stimulating factor, betaseron, erythropoietin (EPO), interferons (E.g. α, β or γ interferon), somatropin, somatotropin, somatostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VITT and interleukins (E.g. interleukin-2). Representative drugs also include: analgesics (E.g. fentanyl, sufentanil, butorphanol, buprenorphine, levorphanol, morphine, hydromorphone, hydrocodone, oxymorphone, methadone, lidocaine, bupivacaine, diclofenac, naproxen and paverin); anti-migraine agents (E.g. sumatriptan and ergot alkaloids); anti-coagulant agents (E.g. heparin and hirudin); anti-emetic agents (E.g. scopolamine, ondansetron, domperidone and metoclopramide); cardiovascular agents, anti-hypertensive agents and vasodilators (E.g. diltizem, clonidine, nifedipine, verapamil, isosorbide-5-mononitrate, organic nitrates and agents used in treatment of heart disorders); sedatives (E.g. benzodiazepines and phenothiozines); narcotic antagonists (E.g. naltrexone and naloxone); chelating agents (E.g. deferoxamine); anti-diuretic agents (E.g. desmopressin and vasopressin); anti-anginal agents (E.g. nitroglycerine); anti-neoplastics (E.g. 5-fluorouracil and bleomycin); prostaglandins; and chemotherapy agents (E.g. vincristine).

Examples of antigens that are therapeutic agents are tumor antigens, pathogen antigens and allergen antigens. A vaccine preparation will contain at least one antigen. "Pathogen antigens" are those characteristic of pathogens, such as antigens derived from viruses, bacteria, parasites or fungi.

Examples of important pathogens include vibrio choleras, enterotoxigenic *E. Coli*, rotavirus, *Clostridium difficile, Shigella* species, *Salmonella typhi*, parainfluenza virus, influenza virus, *Streptococcus mutans, Plasmodium falciparun, Staphylococcus aureus*, rabies virus and Epstein-Barr virus.

Viruses in general include the following families: picronaviridae; caliciviridae, togaviridae; flaviviridae; coronaviridae; rhabodviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae and poxyviridae.

These viruses, especially attenuated versions or otherwise modified versions that are not pathogenic, can also be modified to express targeting ligands on their surface and thus allow for enhanced vaccination.

Bacteria in general include but are not limited to: *P. aeruginosa; E. coli; Klebsiella* sp.; *Serratia* sp; *Pseudomanas* sp.; *P. cepacia; Acinetobacter* sp.; *S. epidermis; E. faecalis; S. pneumonias; S. aureus; Haemophilus* sp.; *Neisseria* sp.; *N. meningitidis; Bacterodies* sp.; *Citrobacter* sp.; *Branhamella* sp.; *Salmonelia* sp.; *Shigella* sp.; *S. Lesteria* sp., *Pasteurella multocida; Streptobacillus* sp.; *S. pyogenes; Proteus* sp.; *Clostridium* sp.; *Erysipelothrix* sp.; *Spirillum* sp.; *Fusospirocheta* sp.; *Treponema pallidum; Borrelia* sp.; *Actinomycetes; Mycoplasma* sp.; *Chlamydia* sp.; *Rickettsia* sp., *Spirchaeta; Legionella* sp.; *Mycobacteria* sp.; *Urealplasma* sp.; *Streptomyces* sp.; *Trichomoras* sp.; and *P. mirabilis*

Parasites include but are not limited to: *Plasmodium falciparum, P. vivax, P. ovale, P. malaria; Toxoplasma gondii; Leishmania mexicana, L. tropica, L.major, L. aethiopica, L. donovani, Trypanosoma cruzi, T. brucei, Schistosoma mansoni, S. haematobium, S. japoniurn; Trichinella spiralis; Wuchereria bancrofti; Brugia malayli; Entamoeba histolytica; Enterobus vermiculoarus; Taenia solium, T. saginata, Trichomonas vaginitis, T. hominis, T. tenax; Giardia lamblia; CrypLosporidium parvum; Pneumocytis carinii, Babesia bovis, B. divergens, B. microti, Isospore belli, L. hominis; Dientamoeba fragiles; Onchocerca volvulus; Ascaris lumbricoides; Necator americanis; Ancylostorna duodenale; Strongyloides stercoralis; Capillaria philippinensis; Angiostrongylys cantonensis; Hymenolepis nan; Diphyllobothrium latum; Echinococcus granulosus, E.multilocularis; Paragonimus westermani, P. caliensis; Chlonorchis sinensis; Opisthorchis felineas, G. Viverini, Fasciola hepatica, Sarcoptes scabiei, Pediculus humanus; Phtirius pubis*; and *Dermatobia hominis.*

Fungi in general include but are not limited to: *Crytpococcus neoformans; Blastomyces dematitidis; Aiellomyces dermatitidis Histoplasfrai capsulatum; Coccidiodes immitis; Candids* species, including *C. albicans, C. tropicalis, C. parapsilosis, C. guilliermondii* and *C. krusei, Aspergillus* species, including *A. fumigatus, A. flavus* and *A. niger*, Rhizopus species; *Rhizomucor* species; *Cunnighammella* species; *Apophysomyces* species, including *A. saksenaea, A. mucor* and *A. absidia; Sporothrix schenckii, Paracoccidioides brasiliensis; Pseudallescheria boydii, Torulopsis glabrata*; and *Dermatophyres* species.

Antigens that are allergens can be haptens, or antigens derived from pollens, dust, molds, spores, dander, insects and foods. Specific examples include the urusiols of *Toxicodendron* species and the sesquiterpenoid lactones.

Adjuvants can, if desired, be delivered by the carrier entity or with a carrier entity. Examples of adjuvants are Freund's Complete Adjuvant, Freund's Incomplete Adjuvant, Hunter's Titermax, Gerbu Adjuvant, Ribi's Adjuvant, Montanide ISA Adjuvant, Aluminum Salt Adjuvants and Nitrocellulose adsorbed protein.

Diagnostic agents include antibodies, nucleic acids and imaging agents, as well as molecules that are needed to make such antibodies, nucleic acids or imaging agents detectable.

A preferred method of the invention for administering a carrier entity to an organism having intestinal epithelium comprises contacting the intestinal epithelium with a polypeptide ligand of the invention in the presence of the carrier entity, such that the carrier entity is transported into or across the intestinal epithelium or into or across a preferred region of the intestine such as M-cells or Peyer's patches.

The carrier entity and the polypeptide ligand can be administered together (E.g., as part of an entity-ligand complex or discretely) or separately. Oral administration is most preferred, but other modes of administration requiring transepithelial transport to reach the target tissue are also acceptable (E.g., rectal administration).

Of course, the ability of the ligands of the invention to target certain cells of the intestinal epithelium also makes the ligands suitable for targeting pharmaceutical agents to the cells themselves for therapy or prophylaxis.

In addition to the aforementioned ligands and methods, the invention also encompasses nucleic acid sequences encoding the ligands of the invention. As stated herein, the term "encodes" includes the actual coding sequence or a complementary strand. Preferred nucleic acid sequences of the invention are shown in the following table:

TABLE 3

| Nucleic Acid Sequences of the Targeting Ligands | |
|---|---|
| ATACTGCCTAGGATGAGAAGTCAACGTAGTATGCTG | SEQ ID NO:44 |
| ATTAGTCTAAGCCACACTCGCACCCAACGTCGGAGA | SEQ ID NO:45 |
| CCTCGAATCAAGCGGACGAGGAAACTTCACCATAGA | SEQ ID NO:46 |
| AGGATTCCGCCACCTCATATCCGTAGTCGGCTCACC | SEQ ID NO:47 |
| AAGCGGCATAATATTCCGCTTATGAATCGAACCATC | SEQ ID NO:48 |
| ATGAAGAGTAGAACGCCAAGAAAGCGAATCATAATC | SEQ ID NO:49 |
| ATACGTCGAAGCCGGCTGCGGCAGATCAGACGACCA | SEQ ID NO:50 |
| AGTAGAAAGAAACACAGGATTCTTAGAATGCGTAAG | SEQ ID NO:51 |
| AGACAGACGACAAGAAAAATACATATTCGAACAAAC | SEQ ID NO:52 |
| CTGAGAAGGAGTCTGCGGCCTAGACGGAATCTGAGT | SEQ ID NO:53 |
| ATTCCCCCCACGCAAATGAGCATAAGGAGTAATATA | SEQ ID NO:54 |
| CATATAAAACCTAATCGGCTCAGGAATCCTCGTATT | SEQ ID NO:55 |
| AGAACGAAGCGAAAGAATCTAAATCGTATCAATACT | SEQ ID NO:56 |
| AGCAAGCCAACGATACTCATGCGTATACGCCGGCTT | SEQ ID NO:57 |
| CGGCATAGGAGACATAGAATGAAACGTATACACATT | SEQ ID NO:58 |
| CGTAAAATTAACCGGAAGCTCCGGCTTAGTCGGCAC | SEQ ID NO:59 |
| AGGAAGAACCGTAACAGGATTCCAAGGCCACAGACC | SEQ ID NO:60 |
| CCAATAAGGAGGAGGCGTAGGATCATTCAGCATATG | SEQ ID NO:61 |
| CGACGGATAACACAAACTAGCACAAGTCGTCTCAAG | SEQ ID NO:62 |
| CGACAGATTATTAAACCCACGAGCATTAGAAACAAG | SEQ ID NO:63 |
| CGAAGGCCGATGAGGCATAGTATCCGAAAAATCAGA | SEQ ID NO:64 |
| CATATCAGCAAGAATACGTCATAGGATGAGGAGGCAC | SEQ ID NO:65 |
| CGGCGTAGGAGACAGAGTATTATCCGTATACACATT | SEQ ID NO:66 |
| AGGCGCAGTCCGCAGAAGCCAAGGCGGAGGAGTAGC | SEQ ID NO:67 |
| ACCAAAAGCCGTATAATACACATTCGGAGACATAGT | SEQ ID NO:68 |
| AAGAGTATACGACACAGAATGCCAATCCGTCCCCAA | SEQ ID NO:69 |
| AATATCCGGAACCATCGTCGCCTCAAGACGAGGCAC | SEQ ID NO:70 |
| CGGAAAACCCGGCACACCACCATTCAACGTCCCAAG | SEQ ID NO:71 |
| CGTCACAGGCCAATGACGATGAGTCGTCGGCACAAG | SEQ ID NO:72 |
| CAAAGAATAAGGAGGCTGCGACGCCCAAGAAATAGA | SEQ ID NO:73 |

In addition, arising from the degeneracy of the genetic code all variations of these DNA sequences resulting in identical amino acid sequences are included in this invention.

The invention will be illustrated in more detail with reference to the following Examples, but it should be understood that the present invention is not deemed to be limited thereto.

EXAMPLES

Example 1

The Screening Process: Biopanning in vivo

A Phage Display Peptide Library (12-mer at $1.5 \times 10^{11}$ pfu) was inoculated intraduodenally into a rat loop model (n=5). Blood samples were taken from the rat loop at time periods of 0, 30, 60, 90 and 120 minutes. The animals were then sacrificed and the loops excised. From these loops, Peyer's patch and non-Peyer's patch tissues were isolated, washed and homogenized. The bacteriophage present in the tissue samples were amplified in E.Coli and isolated by polyethylene glycol (PEG) precipitation. Peyer's patch specific phage were titred and selected for use in subsequent screening cycles.

Four screening cycles were completed and phage titres (in pfu/ml) were obtained at cycle 4.

TABLE 4

Phage titres (pfu/ml) in crude tissue homogenates (rat loop model; cycle 4)

| Rat No. | Peyer's Patch |
| --- | --- |
| 1 | $1.0 \times 10^6$ |
| 2 | $5.6 \times 10^5$ |
| 3 | $4.0 \times 10^3$ |
| 4 | $2.6 \times 10^6$ |
| 5 | $4.6 \times 10^4$ |

Example 2

Phage Binding Studies

The phage pools obtained in Example 1 were plated out on LB agar plates with top agar and phage clones were selected for evaluation by an ELISA analysis of binding to Peyer's patch tissue from various species, along with Caco-2 and IEC-6 cell models.

The ELISA was run with 5 μg/ml of phage homogenates, Blocking buffer: 1% BSA-TBS, wash buffer:TBS-Tween (0.05%), anti-M13 biotin conjugate (Research Diagnostics RDI-PRO61597) at a 1:5000 dilution, ExtrAvidin Alkaline Phosphatase (Sigma E-2636) at a 1:5000 dilution and pNPP substrate.

Five hundred clones (Rats 1–5 from Cycle 4) were subsequently assayed using the above method. (See FIGS. 1A–5 for binding profiles). The clones exhibited a broad range of activity with concentration-dependent binding clearly detectable for all high-binding clones.

TABLE 5

Table of phage clone numbers & SEQ ID NOs.

| SEQ ID NO: | Amino Acid Sequence | No. of copies of each clone isolated | Clone No. | SEQ ID of corresponding DNA sequence: |
| --- | --- | --- | --- | --- |
| SEQ ID NO:1 | ATPPPWLLRTAP | 1 | 3.030 | SEQ ID NO:67 |
| SEQ ID NO:2 | DGSIHKRNIMPL | 1 | 1.010 | SEQ ID NO:48 |
| SEQ ID NO:3 | DYDSLSWRSTLH | 1 | 1.016 | SEQ ID NO:49 |
| SEQ ID NO:4 | GEPTTDMRWRNP | 1 | 1.008 | SEQ ID NO:47 |
| SEQ ID NO:5 | GLWPWNPVTVLP | 5 | 2.054, 3.003, 3.056, 5.006, 5.074 | SEQ ID NO:60 |
| SEQ ID NO:6 | HMLNDPTPPPYW | 2 | 2.061, 4.075 | SEQ ID NO:61 |
| SEQ ID NO:7 | KPAYTHEYRWLA | 3 | 2.025, 2.068, 3.083 | SEQ ID NO:57 |
| SEQ ID NO:8 | LETTCASLCYPS | 1 | 2.078 | SEQ ID NO:62 |
| SEQ ID NO:9 | LGTDWHSVSYTL | 1 | 4.009 | SEQ ID NO:69 |
| SEQ ID NO:10 | LGTLNAGVPGFP | 1 | 5.039 | SEQ ID NO:71 |
| SEQ ID NO:11 | LTHSKNPVFLST | 1 | 1.049 | SEQ ID NO:51 |
| SEQ ID NO:12 | LVPTTHRHWPVT | 1 | 5.049 | SEQ ID NO:72 |
| SEQ ID NO:13 | LVSNARGFNNLS | 1 | 2.081 | SEQ ID NO:63 |
| SEQ ID NO:14 | NTRIPEPIRFYM | 1 | 2.014 | SEQ ID NO:55 |
| SEQ ID NO:15 | NVYTFHSMSPMP | 1 | 2.045 | SEQ ID NO:58 |
| SEQ ID NO:16 | QHTTLTSHPRQY | 1 | 1.002 | SEQ ID NO:44 |
| SEQ ID NO:17 | SDFSDTMPHRPS | 2 | 3.006, 3.090 | SEQ ID NO:64 |
| SEQ ID NO:18 | SIDTIQILSLRS | 3 | 2.016, 3.014, 3.031 | SEQ ID NO:56 |
| SEQ ID NO:19 | SISWASQPPYSL | 1 | 5.078 | SEQ ID NO:73 |
| SEQ ID NO:20 | SMVKFPRPLDSR | 2 | 1.005, 1.076 | SEQ ID NO:46 |
| SEQ ID NO:21 | LRRWVRVWLRL | 1 | 1.004 | SEQ ID NO:45 |
| SEQ ID NO:22 | TMSPNVYYTAFG | 1 | 3.062 | SEQ ID NO:68 |
| SEQ ID NO:23 | TQIPSRPQTPSQ | 1 | 1.099 | SEQ ID NO:53 |
| SEQ ID NO:24 | VCSNMYFSCRLS | 1 | 1.083 | SEQ ID NO:52 |
| SEQ ID NO:25 | VPPHPMTYSCQY | 1 | 3.020 | SEQ ID NO:65 |
| SEQ ID NO:26 | VPRLEATMVPDI | 1 | 4.098 | SEQ ID NO:70 |
| SEQ ID NO:27 | VPTKPELPVNFT | 1 | 2.049 | SEQ ID NO:59 |
| SEQ ID NO:28 | WSSDLPQPASTY | 1 | 1.038 | SEQ ID NO:50 |
| SEQ ID NO:29 | YITPYAHLRGGN | 5 | 2.012, 3.005, 3.013, 3.035, 5.033 | SEQ ID NO:54 |
| SEQ ID NO:30 | NVYTDNTLSPTP | 1 | 1.009 | SEQ ID NO:66 |

Example 3

1. Specificity Determination: analysis of phage binding to rat small intestine and/or Peyer's patch A Biotin-ExtrAvidin Alkaline Phosphatase assay was established for high throughput screening of the phage clones. The initial screens identified 55 out of the 500 clones as high-binding clones (an absorbency reading of>0.75).

The rat tissue homogenates were prepared by harvesting rat GI and Peyer's patch and storing them on ice until needed, or 1–2 hours. The tissue was then put into homogenization buffer (250 mM Sucrose, 12 mM Tris, 16 mM EDTA) with protease inhibitor cocktail. A hand-held homogenizer was used to break up the tissue for 3–4 minutes. The contents of the homogenizer were then transferred to microfuge tubes and spun at 1500 rpm for 1 minute. The supernatant was taken off and measured for protein content using the Bio-Rad Assay. Specificity studies were then run to allow differentiation between Peyer's patch specific and non-specific binding properties. The 55 high-binding clones were assayed for binding to rat small intestinal homogenates (i.e., homogenate membrane fractions) with and without Peyer's Patch tissue (i.e., tissue homogenate membrane fractions) present. (See FIGS. 6 and 7). The negative control was M13 mp18 with no peptide insert. This negative control consistently showed absorbance readings of <0.200. All of the clones exhibited significantly higher binding to both tissue types as compared to the control. However, there was a negligible difference between binding to Peyer's patch and non-Peyer's Patch tissue, which suggests that the clones are binding to factors common to both tissue types.

These results were reproducible when using a further 50 clones with an absorbance reading between 0.5–0.75.

2. Species Specificity: analysis of phage binding to pig, dog and mouse small intestine and/or Peyer's patch One hundred high-binding clones were assayed for their binding properties to pig, dog and mouse small intestinal homogenates that were with and without Peyer's patch tissue homogenates. (See FIGS. 8, 9 and 10). These homogenates were prepared in the same way as the method for obtaining rat homogenates described above. As was observed with the rat tissues, all the clones exhibited a negligible difference between binding to Peyer's patch and non-Peyer's patch tissue suggesting that the clones were binding to sites specific to both tissue types. Several of the clones that had exhibited the highest binding in the rat model also were categorized as high-binding clones in the dog and pig model systems. These clones, numbered 1.002, 1.009, 1.016, 1.038, 1.083, 2.078, 2.080, 3.084, 3.087 and 5.074, along with 100 clones representing high, medium and low binders were selected for sequencing to determine the nature of the peptide inserts that may be implicated in their binding function.

3. Phage Binding assays to IEC-6 and Caco-2 homogenates

Seventy clones were assayed for binding to cell homogenates (IEC-6 and Caco-2 homogenates). IEC-6 cells are a rat normal small intestinal epithelial cell line and Caco-2 cells are a human colon epithelial adenocarcinoma cell line believed to display properties of human small intestinal epithelial cells.

In order to prepare the Caco-2 cell membrane and cytosolic fractions, confluent Caco-2 cell monolayers (grown in 75 cm$^2$ flasks for up to 1 week at 37° C. and 5% CO$_2$) were washed twice in Dulbecco's PBS (DPBS). The cell monolayers were then treated with 10 mM EDTA-DPBS for 5–10 minutes at 37° C. and the cells were harvested by centrifugation at 1000 rpm for 5 minutes. The cells were then washed 3×in DPBS. The cell pellet was resuspended in 3 volumes of ice-cold HED buffer (20 mM HEPES (pH 7.67), 1 mM EGTA, 0,5 mM dithiothreitol, 1 mM phenylmethylsuphonyl fluoride (PMSF)) and the cells were allowed to swell for 5 minutes on ice. The cells were then homogenized for 30 seconds. The cell homogenates were then centrifuged in hard walled tubes at 40,000 rpm for 45 minutes at 4° C. (ultracentrifuge Ti90 rotor). The supernatant was removed and the pellet resuspended in HEDG buffer (20 mM HEPES (pH 7.67), 1 mM EGTA, 0.5 mM dithiothreithol, 100 mM NaCl, 10% glycerol, 1 mM PMSF). Three volumes of buffer were then added and the pellet was resuspended and centrifuged again at 1000 rpm for 2 minutes. The supernatant was removed and stored on ice. The procedure was repeated adding the second supernatant to the first and then the procedure was repeated 2–3 more times. The protein concentration was determined using the Bio-Rad protein assay. All fractions were stored at −80° C.

The IE-6 cell homogenates were prepared in the same way as the Caco-2 homogenates as described above.

Analysis of binding of phage clones to Caco-2 cell membrane fractions by ELISA was done as follows: 96-well ELISA plates were coated overnight at 4° C. with Caco-2 cell membrane fractions (10 μg/ml in 0.05M carbonate buffer (pH 9.6); 100 μl/well). The plates were then blocked in 1.5% BSA-TBS for 1 hour at room temperature (100 μl/well) prior to washing 3×in TBS/Tween 20 (0.05%). Phage clones (1:2 dilution in 1.5% BSATBS) were serially diluted down the plate and incubated for one-two hours at room temperature. After 3 washes in TBS/Tween 20 the phage were incubated with biotinylated mouse anti-M13 MAb (1:5000 dilution in 1.5% BSA-TBS; RDI; 100 μl/well) for one hour at room temperature. The plates were washed three times prior to incubation with extravidin AP (1:5000 dilution in 1.5% BSA-TBS; Sigma; 100 μl/well) at room temperature for one hour. The plates were again washed 3 times in TBS/Tween 20. Alkaline phosphatase activity was detected using the substrate p-NPP (p-nitrophenyl phosphate). After 30 minutes, development of the enzymatic reaction was stopped by addition of 3M NaOH (100 μl/well). The plates were read at 405 nm using an ELISA plate reader.

The clones showed a broad range of activity with high binders exhibiting concentration-dependent binding. The binding profiles showed non-differentiated and differentiated Caco-2 cell fractions giving similar results. The absorbance readings varied between the different tissues and cell types, however, the overall binding profile remained unchanged. (See FIGS. 11 and 12).

Example 4

Sequencing of Selected Phage Clone Inserts

The 100 phage clones from Example 3 including all high-binding clones and a selection of medium- and low-binding clones were sequenced to determine the nature of the peptide inserts.

The phage DNA was isolated using Qiagen's Quiaprep M13 spin kits. The isolated DNA was precipitated and subsequently sequenced with a 96 gIII sequencing primer situated 117 base pairs 3' of the peptide insert.

Of the 100 inserts sequenced, 53% did not contain a detectable insert in gene III and all of these clones represented the low binding clones with an absorbance of <0.4. This appeared to correspond with the library phage (MP13KE) and may have represented loss of the insert during final amplification of selected clones or may have been selected by their ability to be taken up as particulate matter in either Peyer's patch M-cells or enterocytes or alternatively these clones may have a mutation elsewhere in gene III, gene VII or another gene of M13 which was selected during the screening program for binding to/uptake into intestinal epithelium or Peyer's patch tissue in vivo.

A BLAST search using the Swissprot database was performed on thirty of the unique sequences in order to compare the predicted peptide sequence to the protein/peptide sequence database. A summary of BLAST alignments is as follows:

TABLE 6

Alignment of most relevant Blast homologues.

| SEQ ID | Sequence | Homologue of interest | Alignment |
|---|---|---|---|
| SEQ ID NO:4 | GEPTTDMRWRNP | MOUSE KERATINOCYTE GROWTH FACTOR RECEPTOR | Query: 1    GEPTTDMRW 9<br>            G PT+ MRW<br>Sbjct: 183   GNPTSTMRW 191<br>(SEQ ID NO:74) |
| SEQ ID NO:5 | GLWPWNPVTVLP | HUMAN UROKINASE-TYPE PLASMINOGEN ACTIVATOR PRECURSOR (u-PA) | Query: 4    PWNPVTVL 11<br>            PWN   TVL<br>Sbjct: 93    PWNSATVL 100<br>(SEQ 10 NO:75) |
| SEQ ID NO:6 | HMLNDPTPPPY | XENLA EPITHELIAL-CADHERIN PRECURSOR E-CADHERIN) | Query: 4    NDPTPPPY 11<br>            NDPT PPY<br>Sbjct: 811   NDPTAPPY 818<br>(SEQ ID NO:76) |
| SEQ ID NO:7 | KPAYTHEYRWLA | PRECURSOR (FCεRI) (IGE FC RECEPTOR, ALPHA-SUBUNIT) (FC-EPSILON RI-ALPHA) | Query: 4    YTHEYRWL 11<br>            YT EYRWL<br>Sbjct: 196   YTIEYRWL 203<br>(SEQ ID NO:77) |
| SEQ ID NO:8 | LETTCASLCYPS | CLALU LECTIN-RELATED PROTEIN PRECURSOR (CLLRP) (LRPCL) | Query: 2    ETTCASLCYPS 12<br>            ET   ASL YPS<br>Sbjct: 210   ETLIASLTYPS 220<br>(SEQ ID NO:78) |
| | | CAVPO CASEIN A PRECURSOR | Query: 2    ETTCASLC 9<br>            ET CASLC<br>Sbjct: 48    ETICASLC 55<br>(SEQ ID NO:79) |
| SEQ ID NO:9 | LGTDWHSVSYTL | PIG ZONADHESIN PRECURSOR | Query: 1    LGTDWHSVSYT 11<br>            LGTDW S + T<br>Sbjct: 750   LGTDWFSPNCT 760<br>(SEQ ID NO:80) |
| SEQ ID NO:10 | LGTLNAGVPGFP | MOUSE ELASTIN PRECURSOR (TROPOELASTIN) | Query: 4    LNAGVPGF 11<br>            L AGVPGF<br>Sbjct: 612   LGAGVPGF 619<br>(SEQ ID NO:81)<br>Query: 6    AGVPGF 11<br>            AGVPGF<br>Sbjct: 623   AGVPGF 628<br>(SEQ ID NO:82)<br>Query: 6    AGVPGF 11<br>            AGVPGF<br>Sbjct: 632   AGVPGF 637<br>(SEQ ID NO:83)<br>Query: 6    AGVPGF 11<br>            AGVPGF<br>Sbjct: 641   AGVPGF 646<br>(SEQ ID NO:84)<br>Query: 6    AGVPGF 11<br>            AGVPGF<br>Sbjct: 650   AGVPGF 655<br>(SEQ ID NO:85) |
| SEQ ID NO:12 | LVPTTHRHWPVT | MOUSE STROMELYSIN-3 PRECURSOR (MATRIX METALLOPROTEINASE-11) (MMP-11) | Query: 3    PTTHRHWPV 11<br>            P +HRH PV<br>Sbjct: 40    PESHRHHPV 48<br>(SEQ ID NO:86) |
| SEQ ID NO:15 | NVYTFHSMSPMP | RAT SUCRASE-ISOMALTASE, INTESTINAL | Query: 1    NVYTFHSMSPMP 12<br>            N YT   S+ P+P<br>Sbjct: 987   NPYTLTSIQPLP 99<br>(SEQ ID NO:87) |
| SEQ ID NO:16 | QHTTLTSHPRQY | HUMAN PLACENTAL-CADHERIN PRECURSOR (P-CADHERIN) | Query: 2    HTTLTSHP 9<br>            H T+T+HP<br>Sbjct: 376   HFTITTHP 383<br>(SEQ ID NO:88) |
| SEQ ID NO:19 | SISWASQPPYSL | CAPHI BETA CASEIN PRECURSOR | Query: 3    SWASQPPYSL 12<br>            SW   QPP   L<br>Sbjct: 157   SWMHQPPQPL 166<br>(SEQ ID NO:89) |
| SEQ ID NO:20 | SMVKFPRPLDSR | ZO1 MOUSE TIGHT JUNCTION PROTEIN ZO-1 (TIGHT JUNCTION PROTEIN 1) | Query: 6    PRPLDSR 12<br>            PR LDSR<br>Sbjct: 1110   PRDLDSR<br>(SEQ ID NO:90) |

TABLE 6-continued

Alignment of most relevant Blast homologues.

| SEQ ID | Sequence | Homologue of interest | Alignment | |
|---|---|---|---|---|
| SEQ ID NO:23 | TQIPSRPQTPSQ | MOUSE VERSICAN CORE PROTEIN PRECURSOR (LARGE FIBROBLAST PROTEOGLYCAN) (CHONDROITIN SULFATE PROTEOGLYCAN CORE PROTEIN 2) (PG-M) | Query: 1<br>Sbjct:1173<br>(SEQ ID NO:91)<br>Query: 1<br>Sbjct: 307<br>(SEQ ID NO:92) | TQIPSRPQTPS 11<br>T++P  P TPS<br>TELPKFPSTPS1183<br>TQIPSRPQTPS 11<br>T IPS PQ P+<br>TGIPSTPQKPT 317 |
| SEQ ID NO:25 | VPPHPMTYSCQY | PAPCY METALLOPROTEINASE INHIBITOR 1 PRECURSOR (TIMP-1) | Query: 1<br>Sbjct: 27<br>(SEQ ID NO:93) | VPPHPMTYSC 10<br>VPPHP T   C<br>VPPHPQTAFC 36 |
| SEQ ID NO:26 | VPRLEATMVPDI | HUMAN VERSICAN CORE PROTEIN PRECURSOR (LARGE FIBROBLAST PROTEOGLYCAN) (CHONDROITIN SULFATE PROTEOGLYCAN CORE PROTEIN 2) (GLIAL HYALURONATE-BINDING PROTEIN) (GHAP) | Query: 1<br>Sbjct: 2695<br>(SEQ ID NO:94) | VPRLEATMVPDI12<br>+PR   AT++P+I<br>IPRKSATVIPEI 2706 |
| SEQ ID NO:27 | VPTKPELPVNFT | HUMAN COLLAGEN ALPHA 1 (VII) CHAIN PRECURSOR (LONG-CHAIN COLLAGEN) | Query: 1<br>Sbjct: 500<br>(SEQ ID NO:95) | VPTKPELPVN 10<br>VPT PELPV+<br>VPTGPELPVS 509 |
| SEQ ID NO:29 | YITPYAHLRGNN | RAT INSULIN-LIKE GROWTH FACTOR I RECEPTOR | Query: 4<br>Sbjct: 1348<br>(SEQ ID NO:96) | PYAHLRGG 11<br>PYAH+ GG<br>PYAHMNGG 1355 |

The homologue for SEQ ID NO:4 was found to be keratinocyte growth factor receptor (KGFR) which is expressed by intestinal as well as other epithelial cells. It interacts with KGF, a member of the fibroblast growth factor (FGF) family of mitogens which is produced by stromal cells and results in epithelial cell proliferation. The KGF-KGFR interaction is thought to play a role in the epithelial repair processes. See Werner, *Cytokine Growth Factor Rev*, 2:153–65, 1998; Bajaj-Elliott M. et al., *J Clin Invest* 102:1473–80, 1998.

The homologue for SEQ ID NO:5 is urokinase plasminogen activator (u-PA) which is one of the mediators of the plasminogen activator system, that also includes tissue-type plasminogen activator (t-PA) and plasminogen activator inhibitor type-1 (PAI-1). u-PA cleaves plasminogen to the active plasmin which can degrade components of the extracellular matrix (ECM). The u-PA receptor (u-PAR) has been shown to be expressed on different types of epithelial cells including intestinal epithelium. See Gibson P. et al., *Gut* 7:969–75, 1994. Targeting of the u-PAR has also been shown to enhance gene delivery. See Drapkin P. T. et al., *J Clin Invest* 105:589–96, 2000.

SEQ ID NO:6 was found to be homologous to cadherin precursors. Cadherins are epithelial adhesion molecules which allow an intact, selectively permeable, epithelial layer to be formed. They are transmembrane glycoproteins that form a complex with cytoplasmic proteins, termed catenins because they link cadherin to the actin cytoskeleton. The E-cadherin/catenin interaction is important in intestinal epithelial cells and tight junction integrity. See Jawhari A. et al., *Gut* 5:581–4, 1997.

The homologue of SEQ ID NO:7 is a high affinity FcεRI alpha subunit which is a type I transmembrane protein that binds to the Fc region of IgE. In humans, FcεRI plays a role in the activation of mast cells and basophils, and participates in IgE-mediated antigen presentation. FcεRI is therefore central to the induction and maintenance of an allergic response and may confer physiological protection in parasitic infections. See Turner H. and Kinet J. P., *Nature* 402:B24–30, 1999. This protein is expressed on mast cells, eosinophils, Langerhans cells, dendritic cells and monocytes.

SEQ ID NO: 8 shows a strong homology with a lectin-related protein however, unlike true lectins previously shown to bind glycocalyx on enterocytes, this protein is devoid of carbohydrate binding activity. See Van Damme E. J. et al., *Plant Mol Biol* 3:579–98, 1995.

The homologue of SEQ ID NO:9 is a zonadhesion precursor which promotes adhesion of spermatozoa to egg extracellular matrix. Hardy D. M. et al., *J Biol Chem.* 44:26025–8, 1995. It contains adhesive glycoprotein von Willebrand's factor domains which share similarity to intestinal mucin, muc2. It is within one of these domains that homology to the selected peptide is observed.

The homologue of SEQ ID NO:10 is elastin, a major structural protein of extracellular matrix. In mouse, the matrix metalloproteinase matrilysin, for which elastin is a substrate, is found in epithelial cells of the uterus, small intestine and extra-testicular ducts. See Wilson C. L. and Matrisian L. M., *Int J Biochem Cell Biol* 2:123–36, 1996. Interestingly, the 6-residue peptide motif that shares homology with mouse elastin is repeated five times within the protein while a 4-residue motif within this sequence is repeated thirteen times.

SEQ ID NO:12 shows homology to stromelysin, or MMP-3, which is responsible for the breakdown of ECM collagen as well as the cleavage of u-PA. See Ugwu F. et al., *Biochemistry* 2:7231–6, 1998. It plays an important role together with other members of the MMP family in intestinal tissue remodeling and repair. See Pender S. L. et al., *Ann NY Acad Sci* 878:581–2, 1999. Peptide SEQ ID NO:25 showed homology to TIMP-1 (tissue inhibitor of MMPs). This protein forms irreversible complexes with MMPs thus inactivating them. It is present in the intestine where, together with MMPs, it is important in the ongoing repair and renewal that takes place in the intestine.

The homologue of SEQ ID NO:15 was intestinal sucrase-isomaltase which is a brush border hydrolase expressed in epithelial cells located on villi. The greatest amount of the hydrolase is located at the crypt-villus junction and in the lower to mid-villus region. See Traber P. G., *Biochem Biophys Res Commun* 173:765–73, 1990. It has been shown to be down regulated on M-cells in an in vitro co-culture model. See Kerneis S. et al., *Science* 277:949–52, 1997.

Two different peptides, SEQ ID NO:8 and SEQ ID NO:19, show homology with casein A and casein B, respectively. Casein is a milk protein and has been shown to bind to small intestinal brush border membranes. See Bolte G. et al., *J Biochem Biophys Methods* 34:189–203, 1997.

One of the selected peptides, SEQ ID NO:20, shares homology with mouse tight junction protein, ZO-1. See Itoh M. et al., *J Cell Biol* 3:491–502, 1993. The N-terminus may be involved in transducing a signal required for tight junction assembly, while the C-terminus may have specific properties of tight junctions. ZO-1 has been shown in vitro to interact with cadherins.

Several peptides, SEQ ID NOS:23, 26 and 27, show regions of homology with ECM proteins including versican and collagen. These proteins and proteoglycans are important in tissue integrity acting not only as the glue connecting cells together but also acting in cell motility, growth and differentiation.

SEQ ID NO:29 shows homology to high affinity insulin-like growth factor I receptor (IGF IR) from several species. IGF IR has wide tissue expression including epithelial cells of the intestine where it acts as an epithelial cell growth factor. See Wolpert S. I. et al., *J Surg Res* 63:345–8, 1996. IGF is a candidate for total parenteral nutrition.

Example 5

Peptide sequences (SEQ ID NOs: 3, 4, 5, 7, 8, 9, 10, 11, 14, 15, 16, 17, 19, 20, 26, 28, 29, 30) were synthesized with biotin tags at the amino terminal for all peptides and additionally at the carboxyl terminal for SEQ ID NOs:8 and 14. Binding of these peptides to Caco-2 homogenates and/or to rat intestinal tissue homogenates was tested in an ELISA-based assay with streptavidin-peroxidase detection. High binding to both tissue types was observed with the following peptides: SEQ ID NOs:3, 8, 25 and 24. (See FIGS. 13A–13N).

Example 6

Peptide sequences (SEQ ID NOs:3, 7, 8, 9 and 14) were synthesized with biotin tags at the amino terminal for all peptides and additionally at the carboxyl terminal for SEQ ID NOs:8 and 14. Binding of these peptides to intestinal tissue of different species namely dog, mouse, pig, and rat was performed. No major differences in binding profiles to tissue of different species were observed. (See FIGS. 14A–14H). Binding of peptides (SEQ ID NOs:8 and 14) to rat tissue from different organs, namely liver, lung, mesenteric lymph nodes, spleen and kidney, was performed. No major differences in binding profiles to these tissues were observed. (See FIGS. 15A–15E).

Example 7

Three synthetic peptides (SEQ ID NO:8, 25 and 14) derived from isolated clones were biotinylated and tested for binding to human Peyer's patch tissue sections. In addition, a known negative binding peptide was included as a negative control. Paraffin sections of human Peyer's patch were deparaffinized and dehydrated. The sections were rinsed in PBS. The antigenic determinants on the tissue were unmasked by microwaving in 2.1 g/L acetic acid for 5 minutes and allowed to cool at room temperature for 20 minutes while covered in plastic wrap. After 20 minutes, the sections were washed in PBS and then blocked in endogenous peroxidase in 1% hydrogen peroxide in methanol for 10 minutes. The rinse was repeated and the sections were blocked with 2% BSA in PBS for 20 minutes at room temperature. The sections were incubated with peptide at 50 µg/ml in 2° BSA in PBS for 1 hour at room temperature. Control tissue was treated with BSA alone. The sections were rinsed with 0.05% Tween in PBS. Streptavidin-HRP at 1/500 in 2% BSA was added for 30–60 minutes at room temperature. Again, the sections were rinsed with PBS/Tween. DAB substrate was added for up to 5 minutes, and the reaction was stopped by immersing the slides in water. The sections were counterstained using Haematoxlin for 50 seconds and then rinsed in water. The slides were differentiated in 1% acid alcohol for 5–10 seconds and then rinsed in water. The slides were mounted using aqueous mounting medium and a cover slip. The negative control peptide showed no binding. SEQ ID NO:14 (a low to medium binder as determined by ELISA) was also negative for binding in this study. Positive binding to human Peyer's patch was observed with SEQ ID NO: 8 and 25. Both peptides gave positive staining on the apical side of human enterocytes.

Example 8

Cysteine Binding Studies

Peptide SEQ ID NO:8, at a concentration of 6.25 µg/ml, 12.5 µg/ml and 25 µg/ml, was co-incubated with L-cysteine over the concentration range of 100 mM to 0.003 mM. Peptide SEQ ID NO:25, at a concentration of 6.25 µg/ml was co-incubated with L-cysteine over the concentration range of 100 mM to 0.003 mM. The presence of free L-cysteine prevented binding therefore demonstrating that the cysteine groups are also involved in the binding of these peptides (See FIGS. 16A–16D).

Discussion of Examples

SEQ ID NO:8 is a medium binder to intestinal epithelial tissue. When either of the two cysteine residues are substituted with an alanine residue (SEQ ID NOs: 31 and 32), binding is still retained. When both cysteines are substituted with an alanine residue (SEQ ID NO:33), binding to the epithelium is abrogated. When a biotin tag is added to either the amino or carboxyl end, no difference in the binding affinities is observed (See FIG. 17A).

SEQ ID NO:25 is the highest binder of the phage-derived peptides. When the cysteine residue is substituted with an alanine residue (SEQ ID NO:38), binding to the epithelium is abrogated. The stabilized D-form (SEQ ID NO:37) and retro-inverted D-form (SEQ ID NO:40) retained high binding (See FIG. 17B).

SEQ ID NO:24 is a medium binder. When the cysteine residue is substituted with an alanine residue, the binding to the epithelium is abrogated.

Example 9

A derivative of SEQ ID NO:3 with an added Zinc-binding motif (HESSH) at the carboxyl terminal (SEQ ID NO:43)

was tested for binding to Caco-2 homogenates. Enhanced binding was observed with this additional motif (See FIG. 18)

Example 10

Several phage-derived peptides (SEQ ID NOs: 25, 31, 32, 33, and 40) were adsorbed to streptavidin particles (0.289 µm). Peptide coated particles were tested in an ELISA-based assay for binding to Caco-2 homogenates. Binding was retained in all the cases that were examined. In addition, when one double-mutant peptide ligand (SEQ ID NO:33), is adsorbed to polystyrene particles binding that is approximately 60% of that of the parent peptide is observed (See FIGS. 19A–19B).

Example 11

Biotinylated SEQ ID NO:40 was adsorbed to the surface of fluorescent polystyrene particles (0.289 µm) using routine methodologies at room temperature. Mouse intestinal loops containing one or more polystyrene suspensions (typically 300 µl containing $5.0 \times 10^{10}$ particles per ml) were incubated for 30 minutes. The Peyer's patches were excised, fixed in methanol and the M cells were counter-stained with UEA1-rhodamine for subsequent analysis by confocal microscopy. Stained tissues were examined on a BioRad MRC 600 confocal laser-scanning microscope.

Fluorescent particles coated with peptide SEQ ID NO:40 exhibited binding and uptake into M-cells. No binding or uptake was visible using the control streptavidin particles.

Example 12

Titration of Blood Samples for Investigation of Phage Translocation from Gut into Blood High-binding phage clones numbers 1.009, 5.074, 2.078 and 4.009 were injected into rat intestinal loops as described earlier. There were 3 mice per group. Blood samples were taken at 0, 30, 60, 90 and 120 minutes. The animals were then sacrificed and the loops excised. 100 µl of each blood sample was serially diluted in LB and plated out in top agar plates containing IPTG/Xgal. Blue plaques were counted after incubation at 37° C. overnight. There was a PBS control and an m13 mp19 control.

TABLE 8

Titration of blood samples for translocation of phage from the gut into the blood

| Phage Clone No. | Corresponding SEQ ID No. | Blood Dilution | No. of plaques | Total phage per 100 µl of blood |
|---|---|---|---|---|
| 1.009 | SEQ ID NO:30 | Neat | 19 | 19 |
| 5.074 | SEQ ID NO:5 | Neat | 0 | 0 |
| 2.078 | SEQ ID NO:8 | $10^{-6}$ | 45 | $4.5 \times 10^7$ |
| 4.009 | SEQ ID NO:9 | Neat | 34 | 34 |
| M13mp18 | — | $10^{-1}$ | 18 | 180 |
| PBS control | — | Neat | 1 | 1 |

Example 13

SEQ ID NO:8 is one of the preferred phage-derived peptides. It is a medium binder. When either of the two cysteine residues are substituted, binding is abrogated. However, when this double-mutant peptide ligand is adsorbed to polystyrene particles binding to approximately 60% of that of the parent peptide is observed. This may indicate that conformation of the peptides is important. This 12-mer has been synthesized with a biotin tag at either the amino or carboxy end. No differences in binding affinities were observed with the addition of the biotin tag. The stabilized D-form and retro-inverted D form retained high-binding.

TABLE 9

Results of further studies with SEQ ID NO:8

| SEQ ID NO: | Comment | Sequence | Binding Assay results (Caco-2) |
|---|---|---|---|
| 8 | dansyl-lysine derivative | LETTCASLCYPS | High binder (Kd~1 µg/ml) |
| 8 | biotinylated derivative | LETTCASLCYPS | Medium binder (Kd~8 µg/ml) |
| 8 | | LETTCASLCYPS | Medium binder |
| 31 | biotinylated derivative | LETTAASLCYPS | Medium binder (Kd~9 µg/ml) |
| 32 | biotinylated derivative | LETTCASLAYPS | Medium binder (Kd~8 µg/ml) |
| 33 | biotinylated derivative | LETTAASLAYPS | No binding |
| 35 | inverted D-form; biotinylated derivative | spyclsacttel | Medium binder (Kd~13.91 µg/ml) |
| 36 | D-form; biotinylated derivative | lettcaslcyps | (Kd~30.53 µg/ml) |
| 34 | biotinylated derivative | LETTSASLSYPS | No binding |

Example 14

SEQ ID NO:25 is the highest binder of the phage derived peptides. When the cysteine residue is substituted with an alanine residue binding is abrogated. The stabilized D-form and retro-inverted D-form of SEQ ID NO:25 retained high binding.

TABLE 10

Results of further studies with SEQ ID NO:25

| SEQ ID NO: | Comment | Sequence | Binding Assay results (Caco-2 |
|---|---|---|---|
| 25 | Dansyl-lysine derivative | VPPHPMTYSCQY | High binder (Kd < 1 µg/ml) |
| 25 | biotinylated derivative | VPPHPMTYSCQY | High binder (Kd < 5 µg/ml) |
| 38 | biotinylated derivative | VPPHPMTYSAQY | No binding |
| 37 | D-form; biotinylated derivative | vpphpmtyscqy | (Kd~10 µg/ml) |
| 40 | retro D-form of SEQ ID NO:25; biotinylated derivative | yqcsytmphppv | (Kd~10 µg/ml) |
| 39 | biotinylated derivative | VPPHPMTYSSQY | No binding |

While the invention has been described in detail and with reference to specific examples thereof, it will be apparent to one skilled in the art that various changes and modifications can be made therein without departing from the spirit and scope thereof.

What is claimed is:

1. A purified synthetic polypeptide ligand comprising a 12-mer L-peptide or a homologue thereof, said 12-mer L-peptide consisting of SEQ ID NO:1 wherein said homologue is at least $10/12$ homologous to said 12-mer peptide and wherein said 12-mer L-peptide or homologue thereof, when integrated as an N-terminal PIII fusion peptide of an M13 phage confers an ability to bind the phage to either Caco-2 cell, IEC-6 cell, rat, mouse, pig or dog homogenate membrane fractions, said ability to bind being at least as great as that conferred by a similarly integrated 12-mer peptide of SEQ ID NO:67.

2. A purified synthetic polypeptide ligand of claim 1, wherein said ligand comprises a zinc-binding domain.

3. A purified synthetic polypeptide ligand of claim 1, wherein the homologue is at least $11/12$ homologous to a 12-mer peptide.

4. A purified synthetic polypeptide ligand of claim 1, wherein said ligand comprises a 12-mer L-peptide consisting of SEQ ID NO:1.

5. A purified synthetic polypeptide ligand of claim 1, wherein said ligand consists of an amino acid sequence consisting of SEQ ID NO:1 or homologue thereof.

6. A purified synthetic polypeptide ligand of claim 1, wherein said ligand consists of a 12-mer L-peptide consisting of SEQ ID NO:1.

7. A purified synthetic polypeptide ligand of claim 1, wherein said ligand is at most 200 amino acids in length.

8. A purified synthetic polypeptide ligand of claim 1, wherein said polypeptide ligand is at least 30 amino acids in length.

9. A purified synthetic polypeptide ligand comprising a 12-mer D-peptide or a homologue thereof, said 12-mer D-peptide being the D-form of a 12-mer L-peptide consisting of SEQ ID NO:1, wherein said homologue is at least $9/12$ homologous to said 12-mer D-peptide and wherein said 12-mer D-peptide homologue, when integrated as an N-terminal PIII fusion peptide of an M13 phage confers an ability to bind the phage to either Caco-2 cell, IEC-6 cell, rat, mouse, pig or dog homogenate membrane fractions, said ability to bind being at least as great as that conferred by a similarly integrated 12-mer peptide of SEQ ID NO:67.

10. A purified synthetic polypeptide ligand of claim 9, wherein said ligand comprises a zinc-binding domain.

11. A purified synthetic polypeptide ligand of claim 9, wherein the homologue is at least $10/12$ homologous to a 12-mer D-peptide.

12. A purified synthetic polypeptide ligand of claim 9, wherein the homologue is at least $11/12$ homologous to a 12-mer D-peptide.

13. A purified synthetic polypeptide ligand of claim 9, wherein said ligand comprises a 12-mer D-peptide being the D-form of a 12-mer consisting of SEQ ID NO:1.

14. The purified synthetic polypeptide ligand of claim 9, wherein said ligand consists of the D-form of a 12-mer L-peptide consisting of SEQ ID NO:1.

15. A purified synthetic polypeptide ligand of claim 9, wherein said ligand is at most 200 amino acids in length.

16. A purified synthetic polypeptide ligand of claim 9, wherein said polypeptide ligand is at least 30 amino acids in length.

17. A purified synthetic polypeptide ligand comprising a 12-mer retro-inverted peptide or a homologue thereof, said 12-mer retro-inverted peptide being the retro-inverted form of a 12-mer L-peptide consisting of SEQ ID NO:1, wherein said homologue is at least 9/12 homologous to said 12-mer retro-inverted and wherein said 12-mer retro-inverted peptide or homologue, when integrated as an N-terminal PIII fusion peptide of an M13 phage confers an ability to bind the phage to either Caco-2 cell, IEC-6 cell, rat, mouse, pig or dog homogenate membrane fractions, said ability to bind being at least as great as that conferred by a similarly integrated 12-mer peptide of SEQ ID NO:67.

18. A purified synthetic polypeptide ligand of claim 17, wherein said ligand comprises a zinc-binding domain.

19. A purified synthetic polypeptide ligand of claim 17, wherein the homologue is at least 10/12 homologous to a 12-mer retro-inverted peptide.

20. A purified synthetic polypeptide ligand of claim 17, wherein the homologue is at least 11/12 homologous to a 12-mer retro-inverted peptide.

21. A purified synthetic polypeptide ligand of claim 17, wherein said ligand comprises a 12-mer retro-inverted peptide being the retro-inverted form of a 12-mer L-peptide consisting of SEQ ID NO:1.

22. A purified synthetic polypeptide ligand of claim 17, wherein said ligand consists of an amino acid sequence selected from the group consisting of the retro-inverted form of a 12-mer L-peptide of SEQ ID NO:1 or a homologue thereof.

23. A purified synthetic polypeptide ligand of claim 17, wherein said ligand consists of the retro-inverted form of a 12-mer L-peptide consisting of SEQ ID NO:1.

24. A purified synthetic polypeptide ligand of claim 17, wherein said ligand is at most 200 amino acids in length.

25. The purified synthetic polypeptide ligand of claim 17, wherein said polypeptide ligand is at least 30 amino acids in length.

26. A purified synthetic polypeptide ligand of claim 1, 9, or 17, wherein said polypeptide ligand is integrated into the protein of a phage.

27. The ligand of claim 26, wherein said polypeptide ligand is expressed on the surface of a phage further comprising an antigen and/or a gene encoding the antigen also expressed on the surface.

28. The ligand of claim 26, wherein said polypeptide ligand is expressed on the surface of a bacterium further comprising an antigen and/or a gene encoding the antigen also expressed on the surface.

29. A purified synthetic polypeptide ligand of claim 1, 9, or 17, wherein said polypeptide ligand is covalently or non-covalently bound to a carrier entity comprising a pharmaceutical agent.

30. The purified synthetic polypeptide ligand of claim 29, wherein said carrier entity is selected from the group consisting of a nanoparticle, a microparticle, a liposome, a bacterium, a phage and a virus.

31. The purified synthetic polypeptide ligand of claim 30, wherein said carrier entity is selected from the group consisting of a nanoparticle, microparticle and a liposome.

32. The purified synthetic polypeptide ligand of claim 31, wherein said carrier entity has a largest dimension that is in the range of 10 nm to 500 µm.

33. The ligand of claim 29, wherein said pharmaceutical agent is a drug or therapeutic agent.

34. The ligand of claim 29, wherein said pharmaceutical agent is a pathogen antigen.

35. The ligand of claim 29, wherein said pharmaceutical agent is an adjuvant.

36. The purified synthetic polypeptide ligand of claim 29, wherein said carrier entity is selected from the group consisting of a phage and a virus.

37. A method of administering a pharmaceutical agent to an organism having intestinal epithelium, said method comprising contacting said intestinal epithelium with a purified synthetic polypeptide ligand, said ligand being covalently, or non-covalently bound to, a carrier entity, wherein said ligand is selected from the group consisting of:

(a) a ligand comprising a 12-mer L-peptide, fragment or a homologue thereof, said 12-mer L-peptide consisting of SEQ ID NO:1 wherein said fragment is at least five contiguous amino acids and wherein said homologue is at least 9/12 homologous to said 12-mer peptide and wherein said 12-mer L-peptide, fragment or homologue thereof, when integrated as an N-terminal PIII fusion peptide of an M13 phage confers an ability to bind the phage to either Caco-2 cell, IEC-6 cell, rat, mouse, pig or dog homogenate membrane fractions, said ability to bind being at least as great as that conferred by a similarly integrated 12-mer peptide of SEQ ID NO:67;

(b) a ligand comprising a 12-mer D-peptide, fragment or a homologue thereof, said 12-mer D-peptide being the D-form of a 12-mer L-peptide consisting of SEQ ID NO:1, wherein said fragment is at least five contiguous amino acids and wherein said homologue is at least 9/12 homologous to said 12-mer D-peptide and wherein said 12-mer D-peptide, fragment or homologue, when integrated as an N-terminal PIII fusion peptide of an M13 phage confers an ability to bind the phage to either Caco-2 cell, IEC-6 cell, rat, mouse, pig or dog homogenate membrane fractions, said ability to bind being at least as great as that conferred by a similarly integrated 12-mer peptide of SEQ ID NO:67; and (c) a ligand comprising a 12-mer retro-inverted peptide, fragment or a homologue thereof, said 12-mer retro-inverted peptide being the retro-inverted form of a 12-mer L-peptide consisting of SEQ ID NO:1, wherein said fragment is at least five contiguous amino acids and wherein said homologue is at least 9/12 homologous to said 12-mer retro-inverted peptide arid wherein said 12-mer retro-inverted peptide, fragment or homologue, when integrated as an N-terminal PIII fusion peptide of an M13 phage confers an ability to bind the phage to either Caco-2 cell, IEC-6 cell, rat, mouse, pig or dog homogenate membrane fractions, said ability to bind being at least as great as that conferred by a similarly integrated 12-mer peptide of SEQ ID NO:67.

38. The method of claim 37, wherein said organism is a mammal.

39. The method of claim 38, wherein said mammal is a human.

40. The method of claim 37, wherein said carrier entity is selected from the group consisting of a nanoparticle, microparticle, liposome, bacterium, phage and a viral carrier.

41. The method of claim 37, wherein said carrier entity is selected from the group consisting of a nanoparticle, microparticle and liposome.

42. The method of claim 41, wherein said carrier entity has its major dimension in the range of 10 nm to 500 μm.

43. The method of claim 41, wherein said nanoparticle, microparticle, or liposome is loaded with a pharmaceutical agent or encapsulated with a pharmaceutical agent.

44. The method of claim 37, wherein said administration is done via the oral route.

45. The method of claim 37, wherein said administration is done via either a rectal, subcutaneous, intramuscular, nasal or intravenous route.

46. The method of claim 37, wherein said pharmaceutical agent is a vaccine.

47. The method of claim 37, wherein said purified synthetic polypeptide ligand is a peptide integrated into the protein of a phage which is coated, adsorbed or covalently bonded to a surface of a carrier that is either a nanoparticle or microparticle.

48. The method of claim 47, wherein said phage is modified to contain DNA encoding an antigen.

49. The method of claim 47, wherein said nanoparticle or microparticle is loaded with a pharmaceutical agent or encapsulated with a pharmaceutical agent.

50. A method of claim 37, wherein the purified synthetic polypeptide ligand comprises a zinc-binding motif, and said ligand is contacted with said epithelium in the presence of zinc.

51. A method of claim 37, wherein said carrier entity is selected from the group consisting of a phage and a viral carrier.

52. The method of claim 51, wherein said phage comprises a targeting ligand on its surface.

53. A purified synthetic polypeptide ligand comprising a fragment selected from the group consisting of (a) a fragment of a 12-mer L-peptide consisting of SEQ ID NO:1 wherein said fragment is at least eight contiguous amino acids and wherein said fragment, when integrated as an N-terminal PIII fusion peptide of an M13 phage confers an ability to bind the phage to either Caco-2 cell, IEC-6 cell, rat, mouse, pig or dog homogenate membrane fractions, said ability to bind being at least as great as that conferred by a similarly integrated 12-mer peptide of SEQ ID NO:67;

(b) a fragment of a 12-mer D-peptide, said 12-mer D-peptide being the D-form of a 12-mer L-peptide consisting of SEQ ID NO:1, wherein said fragment is at least eight contiguous amino acids and wherein said fragment, when integrated as an N-terminal PIII fusion peptide of an M13 phage confers an ability to bind the phage to either Caco-2 cell, IEC-6 cell, rat, mouse, pig or dog homogenate membrane fractions, said ability to bind being at least as great as that conferred by a similarly integrated 12-mer peptide of SEQ ID NO:67; and (c) a fragment of a 12-mer retro-inverted peptide, said 12-mer retro-inverted peptide being the retro-inverted form of a 12-mer L-peptide consisting of SEQ ID NO:1, wherein said fragment is at least eight contiguous amino acids and wherein said fragment, when integrated as an N-terminal PIII fusion peptide of an M13 phage confers an ability to bind the phage to either Caco-2 cell, IEC-6 cell, rat, mouse, pig or dog homogenate membrane fractions, said ability to bind being at least as great as that conferred by a similarly integrated 12-mer peptide of SEQ ID NO:67.

54. A purified synthetic polypeptide ligand of claim 53, wherein said ligand comprises a zinc-binding domain.

55. A purified synthetic polypeptide ligand of claim 53, wherein said ligand consists of a fragment of a 12-mer L-peptide consisting of SEQ ID NO:1.

56. A purified synthetic polypeptide ligand of claim 53, wherein said ligand is at most 200 amino acids in length.

57. A purified synthetic polypeptide ligand of claim 53, wherein said ligand is at least 12 amino acids in length.

58. A purified synthetic polypeptide ligand of claim 53, wherein said polypeptide ligand is at least 30 amino acids in length.

* * * * *